US011583579B2

(12) United States Patent
Lipkin et al.

(10) Patent No.: US 11,583,579 B2
(45) Date of Patent: *Feb. 21, 2023

(54) TILAPIA VIRUS AND USES THEREOF

(71) Applicants: The Trustees of Columbia University in the City of New York, New York, NY (US); Ramot at Tel-Aviv University Ltd., Tel Aviv (IL); Kimron Veterinary Institute, Bet Dagan (IL)

(72) Inventors: W. Ian Lipkin, New York, NY (US); Thomas Briese, White Plains, NY (US); Nischay Mishra, New York, NY (US); Eran Bacharach, Tel Aviv (IL); Avi Eldar, Bet Dagan (IL)

(73) Assignees: THE TRUSTEES OF COLUMBIA UNIVERSITY IN THE CITY OF NEW YORK, New York, NY (US); RAMOT AT TEL-AVIV UNIVERSITY LTD., Tel Aviv (IL); KIMRON VETERINARY INSTITUTE, Bet Dagan (IL)

( * ) Notice: Subject to any disclaimer, the term of this patent is extended or adjusted under 35 U.S.C. 154(b) by 0 days.

This patent is subject to a terminal disclaimer.

(21) Appl. No.: 17/193,583

(22) Filed: Mar. 5, 2021

(65) Prior Publication Data
US 2021/0205437 A1    Jul. 8, 2021

Related U.S. Application Data

(63) Continuation of application No. 16/783,597, filed on Feb. 6, 2020, now Pat. No. 10,973,902, which is a continuation of application No. 16/110,432, filed on Aug. 23, 2018, now Pat. No. 10,596,249, which is a continuation of application No. 15/536,325, filed as application No. PCT/US2015/065795 on Dec. 15, 2015, now Pat. No. 10,183,072.

(60) Provisional application No. 62/091,824, filed on Dec. 15, 2014.

(51) Int. Cl.
*A61K 39/12* (2006.01)
*C07K 14/005* (2006.01)
*C12Q 1/70* (2006.01)

(52) U.S. Cl.
CPC ............ *A61K 39/12* (2013.01); *C07K 14/005* (2013.01); *C12Q 1/701* (2013.01); *C12N 2720/00034* (2013.01); *C12N 2760/00021* (2013.01); *C12N 2760/00022* (2013.01); *C12N 2760/00034* (2013.01)

(58) Field of Classification Search
CPC ............ A61K 39/12; A61K 2039/53; A61K 2039/525; C12N 7/00; C12N 2310/11; C12N 15/01; C12N 2760/00043; C12N 2760/00051; C12N 2760/00021; C12N 2760/00022; C12N 2760/00034; C07K 14/005
See application file for complete search history.

(56) References Cited

U.S. PATENT DOCUMENTS

| | | | |
|---|---|---|---|
| 9,730,998 | B2 | 8/2017 | Bacharach et al. |
| 2004/0081638 | A1 | 4/2004 | Kyle |
| 2009/0149641 | A1 | 6/2009 | Jorgensen et al. |
| 2013/0058968 | A1 | 3/2013 | Lipkin et al. |
| 2013/0211063 | A1 | 8/2013 | Manoharan et al. |
| 2015/0343043 | A1 | 12/2015 | Crump et al. |

FOREIGN PATENT DOCUMENTS

| | | |
|---|---|---|
| CN | 106456737 A | 2/2017 |
| WO | WO 97/06243 | 2/1997 |
| WO | WO 03/050142 | 6/2003 |

OTHER PUBLICATIONS

Bacharach E. Tilapia lake virus clone 7450 hypothetical protein gene, partial eds GenBank: KJ605629.1. Dep. Mar. 20, 2014.
Bacharach, E. Tilapia lake virus isolate Til-4-2011 segment 2, complete sequence. Gen Bank: KU751815.1. Dep. Apr. 6, 2016.
Bacharach, E. Tilapia lake virus isolate Til-4-2011 segment 5, complete sequence. Gen Bank: KU751818.1. Dep. Apr. 6, 2016.
Bacharach, E. Tilapia lake virus isolate Til-4-2011 segment 6, complete sequence. Gen Bank: KU751819.1. Dep. Apr. 6, 2016.
Bacharach, E. Tilapia lake virus isolate Til-4-2011 segment 7, complete sequence. Gen Bank: KU751820.1. Dep. Apr. 6, 2016.
Bacharach, E. Tilapia lake virus isolate Til-4-2011 segment 4, complete sequence. Gen Bank: KU751817.1. Dep. Apr. 6, 2016.
Bacharach, E. Tilapia lake virus isolate Til-4-2011 segment 1, complete sequence. Gen Bank: KU751814.1. Dep. Apr. 6, 2016.
Bacharach, E. Tilapia lake virus isolate Til-4-2011 segment 10, complete sequence. Gen Bank: KU751823.1. Dep. Apr

(56) References Cited

OTHER PUBLICATIONS

Bacharach et al., "Hypothetical protein, partial Tilapia lake virus]". GenBank: AIR74928.1, Pub. Oct. 1, 2014; hereafter "AIR74928").

Eyongor et al. "Identifiaction of a Novel RNA Virus Lethal to Tilapia", Journal of Clinical Microbiology, epub. Sep. 17, 2014 (Sep. 17, 2014), vol. 52, pp. 4137-4146, entire document.

Agius C, Roberts RJ. Apr. 8, 2003. Melano-macrophage centres and their role in fish pathology. J. Fish Dis. 26:499-509.

Altschul SF, Madden TL, Schäffer AA, Zhang J, Zhang Z, Miller W, Lipman PJ. Jul. 16, 1997. Gapped BLAST and PSI-BLAST: a new generation of protein database search programs. Nucleic Acids Res. 25:3389-3402.

Bacharach E, Gonsky J, Alin K, Orlova M, Goff SP. Dec. 2000. The carboxyterminal fragment of nucleolin interacts with the nucleocapsid domain of retroviral gag proteins and inhibits virion assembly. J. Virol. 74:11027-11039.

Bigarré L, Cabon J, Baud M, Heimann M, Body A, Lieffrig F, Castric J. Nov. 25, 2009. Outbreak of betanodavirus infection in tilapia, Oreochromis niloticus (L.), in fresh water. J. Fish Dis. 32:667-673.

Brawand et al. The genomic substrate for adaptive radiation in African cichlid fish. Sep. 18, 2014. Nature 513:375-81.

Camacho et al. BLAST+: architecture and applications. Dec. 15, 2009. BMC Bioinformatics 10:421.

Crandell RA, Melloh AJ, Sorlie PJ. Dec. 1975. Sensitivity of infectious bovine rhinotracheitis virus to ether. J. Clin. Microbiol. 2:465-468.

Food and Agriculture Organization of the United Nations (FAO). 2010. Cultured aquatic species information programme, Oreochromis niloticus (Linnaeus, 1758). Food and Agriculture Organization of the United Nations, Rome, Italy.

Food and Agriculture Organization of the United Nations (FAO). 2010. Fisheries and Aquaculture Department. Species fact sheets: Oreochromis niloticus (Linnaeus, 1758). Food and Agriculture Organization of the United Nations, Rome, Italy.

Food and Agriculture Organization of the United Nations (FAO). 2004. The state of world fisheries and aquaculture. Food and Agriculture Organization of the United Nations, Rome, Italy.

Hasegawa S, Somamoto T, Nakayasu C, Nakanishi T, Okamoto N. 1997. A cell line (CFK) from fin of isogeneic ginbunga crucian carp. Fish Pathol. 32:127-128.

Hedrick RP, Gilad O, Yun S, Spangenberg JV, Marty GD, Nordhausen RW, Kebus MJ, Bercovier H, Eldar A. 2000. A herpesvirus associated with mass mortality of juvenile and adult koi, a strain of common carp. J. Aquat. Anim. Health 12:44-57. Accepted Dec. 1, 1999.

Hutoran M, Ronen A, Perelberg A, Ilouze M, Dishon A, Bejerano I, Chen N, Kotler M. 2005. Description of an as yet unclassified DNA virus from diseased Cyprinus carpio species. J. Virol. 79:1983-1991. Feb. 2005.

Johnson M, Zaretskaya I, Raytselis Y, Merezhuk Y, McGinnis S, Madden TL. Apr. 24, 2008. NCBI BLAST: a better web interface. Nucleic Acids Res. 36(Suppl 2):W5-W9.

Laham-Karam N, Bacharach E. Oct. 2007. Transduction of human immunodeficiency virus type 1 (HIV-1) vectors lacking encapsidation and dimerization signals. J. Virol. 81:10687-10698.

Li, Heng. Mar. 2013. Aligning sequence reads, clone sequences and assembly contigs with BWA-MEM. arXiv:1303.3997.

Martin, Marcel. Cutadapt removes adapter sequences from high-throughput sequencing reads. May 2011 EMBnet.journal 17:10-12.

Melamed D, Mark-Danieli M, Kenan-Eichler M, Kraus LO, Castiel A, Laham N, Pupko T, Glaser F, Ben-Tai N, Bacharach E. Sep. 2004. The conserved carboxy terminus of the capsid domain of human immunodeficiency virus type 1 gag protein is important for virion assembly and release. J. Virol. 78:9675-9688.

Nehls M, Boehm T. Feb. 1995. A rapid and efficient alternative to sonication in shot-gun sequencing projects. Trends Genet. 11:39.

Oberpichler I, Rosen R, Rasouly A, Vugman M, Ron EZ, Lamparter T. Feb. 21, 2008. Light affects motility and infectivity of Agrobacterium tumefaciens. Environ. Microbiol. 10:2020-2029.

Pruitt et al. NCBI Reference Sequences (RefSeq): current status, new features and genome annotation policy. Nov. 24, 2012. Nucleic Acids Res. 40:D130-D135.

Reynolds ES. 1963. The use of lead citrate at high pH as an electronopaque stain in electron microscopy. J. Cell. Biol. 17:208-212. Nov. 19, 1962.

Scotto-Lavino E, Du G, Frohman MA. 2006. 3' end cDNA amplification using classic RACE. Nat. Protoc. 1:2742-2745. Published Online Jan. 11, 2007.

Scotto-Lavino E, Du G, Frohman MA. Dec. 29, 2006. 5' end cDNA amplification using classic RACE. Nat. Protoc. 1:2555-2562.

Shlapobersky M, Sinyakov MS, Katzenellenbogen M, Sarid R, Don J, Avtalion RR. Feb. 1, 2010. Viral encephalitis of tilapia larvae: primary characterization of a novel herpes-like virus. Virology 399:239-247.

Yang et al. De novo assembly of highly diverse viral populations. Sep. 13, 2012. BMC Genomics 13:475.

Amend DF. Oct. 1975. Detection and transmission of infectious hematopoietic necrosis virus in rainbow trout. J. Wildl. Dis. 11:471-478.

Biacchesi S, Le Berre M, Le Guillou S, Benmansour A, Brémont M, Quillet E, Budinot P. Apr. 18, 2007. Fish genotype significantly influences susceptibility of juvenile rainbow trout, Oncorhynchus mykiss (Walbaum), to waterborne infection with infectious salmon anaemia virus. J. Fish Dis. 30:631-636.

Binesh CP. 2014. Elevation of temperature and crowding trigger acute viral nervous necrosis in zebra fish, Brachydanio rerio (Hamilton-Buchanan), subclinically infected with betanodavirus. J. Fish Dis. 37:279-282. Accepted Nov. 27, 2012.

Iwamoto T, Nakai T, Mori K, Arimoto M, Furusawa I. Nov. 14, 2000. Cloning of the fish cell line SSN-1 for piscine nodaviruses. Dis. Aquat. Organ. 14:81-89.

Frantisi C, Savan M. Oct. 1971. Infectious pancreatic necrosis virus-temperature and age factors in mortality. J. Wildl. Dis. 7:249-255.

Gilad O, Yun Y, Adkinson MA, Way K, Willirts NH, Bercovier H, Hedrick RP. Jun. 6, 2003. Molecular comparison of isolates of an emerging fish pathogen, koi herpesvirus, and the effect of water temperature on mortality of experimentally infected koi. J. Gen. Virol. 84:2661-2668.

Karvonen A, Kristjánsson BK, Skúlason S, Lanki M, Rellstab C, Jokela J. Mar. 19, 2013. Water temperature, not fish morph, determines parasite infections of sympatric Icelandic threespine sticklebacks (Gasterosteus aculeatus). Ecol. Evol. 3:1507-1517.

Marcogliese DJ. Apr. 19, 2001. Implications of climate change for parasitism of animals in the aquatic environment. Can. J. Zool. 79:1331-1352.

Sugahara K, Eguchi M. 2012. The use of warmed water treatment to induce protective immunity against the bacterial cold-water disease pathogen Flavobacterium psychrophilum in ayu (Plecoglossus altivelis). Fish Shellfish Immunol. 32:489-493 Available online Dec. 13, 2011.

Hershberger PK, Gregg JL, Grady CA, Taylor L, Winton JR. Dec. 7, 2010. Chronic and persistent viral hemorrhagic septicemia virus infections in Pacific herring. Dis. Aquat. Organ. 93:43-49.

LaPatra SE, Lauda KA, Jones GR, Walker SC, Shewmaker BS, Morton AW. Jan. 1, 1995. Characterization of IHNV isolates associated with neurotropism. Vet. Res. 26:433-437.

St Hilaire S, Ribble C, Traxler G, Davies T, Kent ML. Oct. 8, 2001. Evidence for a carrier state of infectious hematopoietic necrosis virus in Chinook salmon Oncorhynchus tshawytscha. Dis. Aquat. Organ. 46:173-179.

VHSV Expert Panel and Working Group. 2010. Viral hemorrhagic septicemia virus (VHSV IVb) risk factors and association measures derived by expert panel. Prev. Vet. Med. 94:128-139. Accepted Nov. 25, 2009.

Faisal M, Shavalier M, Kim RK, Millard EV, Gunn MR, Winters AD, Schulz CA, Eissa A, Thomas MV, Wolgamood M, Whelan GE, Winton J. May 3, 2012. Spread of the emerging viral hemorrhagic septicemia virus strain, genotype IVb, in Michigan, USA. Viruses 4:734-760.

Gagné N, Johnson SC, Cook-Versloot M, MacKinnon AM, Olivier G. Dec. 13, 2004. Molecular detection and characterization of

(56) References Cited

OTHER PUBLICATIONS nodavirus in several marine fish species from the northeastern Atlantic. Dis. Aquat. Organ. 62:181-189.

Dorson M, Quillet E, Hollebecq MG, Torhy C, Chevassus B. Jan. 1, 1995. Selection of rainbow trout resistant to viral haemorrhagic septicaemia virus and transmission of resistance by gynogenesis. Vet. Res. 26:361-368.

Verrier ER, Langevin C, Tohry C, Houel AV, Ducrocq V, Benmansour A, Quillet E, Boudinot P. Apr. 13, 2012. Genetic resistance to rhabdovirus infection in teleost fish is paralleled to the derived cell resistance status. PLoS One 7:4e33935.

Kjøglum S, Larsen S, Bakke HG, Grimholt U. Apr. 17, 2006. How specific MHC class I and class II combinations affect disease resistance against infectious salmon anaemia in Atlantic salmon (*Salmo salar*). Fish Shellfish Immunol 21:431-441.

Midtlyng PJ, Lillehaug A. Mar. 5, 1998. Growth of Atlantic salmon *Salmo salar* after intraperitoneal administration of vaccines containing adjuvants. Dis. Aquat. Organ. 32:91-97.

Norris A, Foyle L, Ratcliff J. Dec. 2008. Heritability of mortality in response to a natural pancreas disease (SPDV) challenge in Atlantic salmon, *Salmo salar* L., post-smolts on a West of Ireland sea site. J. Fish Dis. 31:913-920.

Purcell MK, Lapatra SE, Woodson JC, Kurath G, Winton JR. 2010. Early viral replication and induced or constitutive immunity in rainbow trout families with differential resistance to infectious hematopoietic necrosis virus (IHNV). Fish Shellfish Immunol. 28:98-105. Available online Oct. 9, 2009.

Quillet E, Dorson M, Le Guillou S, Benmansour A, Boudinot P. 2007. Wide range of susceptibility to rhabdoviruses in homozygous clones of rainbow trout. Fish Shellfish Immunol. 22:510-519. Available online Jul. 31, 2006.

Slierendrecht WJ, Olesen NJ, Juul-Madsen HR, Lorenzen N, Henryon M, Berg P, Søndergaard J, Koch C. 2001. Rainbow trout offspring with different resistance to viral haemorrhagic septicaemia. Fish Shellfish Immunol. 11:155-167. Accepted Aug. 17, 2000.

øvergård AC, Nerland AH, Patel S. May 11, 2010. Evaluation of potential reference genes for real time RT-PCR studies in Atlantic halibut (*Hippoglossus hippoglossus* L.) during development, in tissues of healthy and NNVinjected fish, and in anterior kidney leucocytes.BMCMol. 11:36.

Purcell MK, Laing KJ, Winton JR. Jan. 18, 2012. Immunity to fish rhabdoviruses. Viruses 4:140-166.

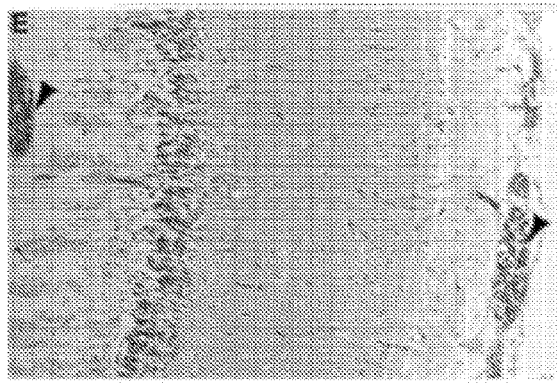
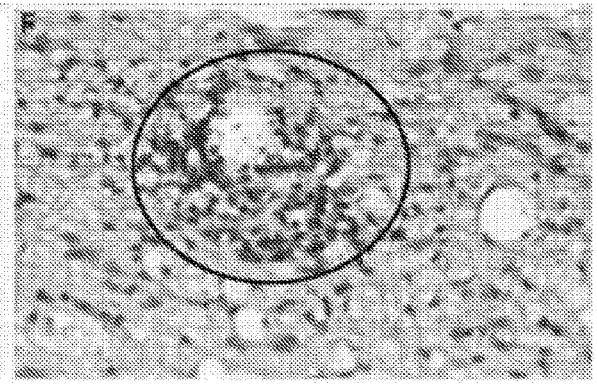
Fig. 1E        Fig. 1F
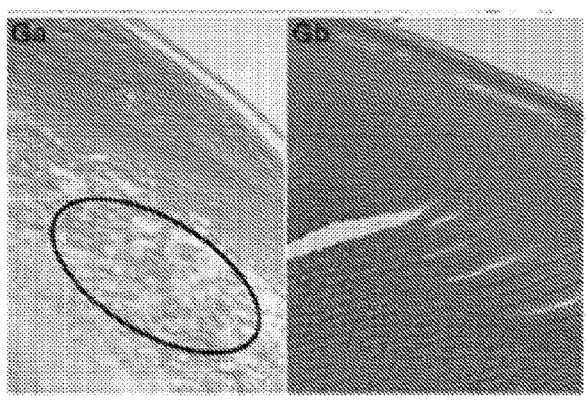
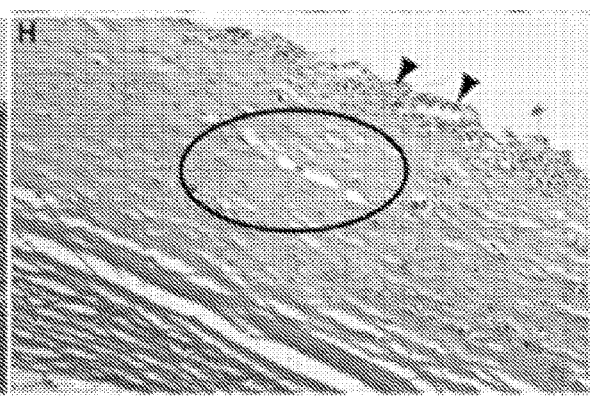
Fig. 1Ga    Fig. 1Gb        Fig. 1H

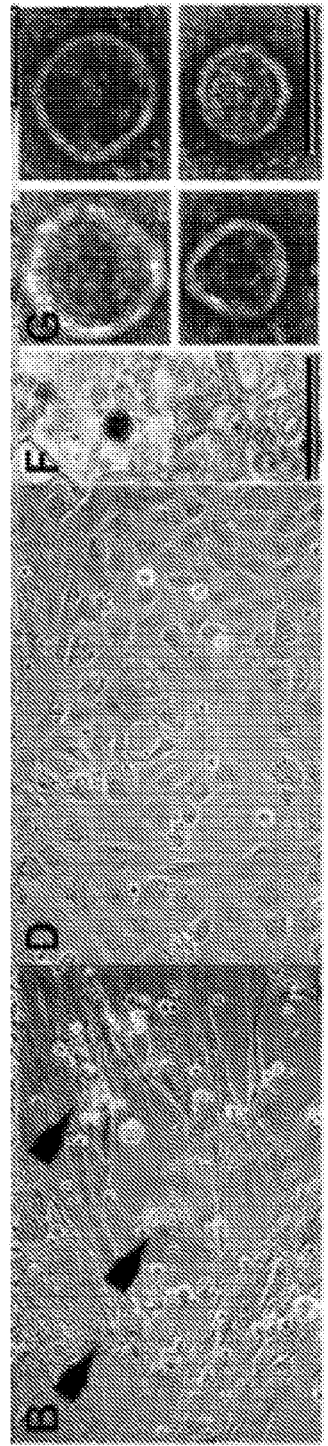
Fig. 2A  Fig. 2C  Fig. 2E
Fig. 2B  Fig. 2D  Fig. 2F  Fig. 2G

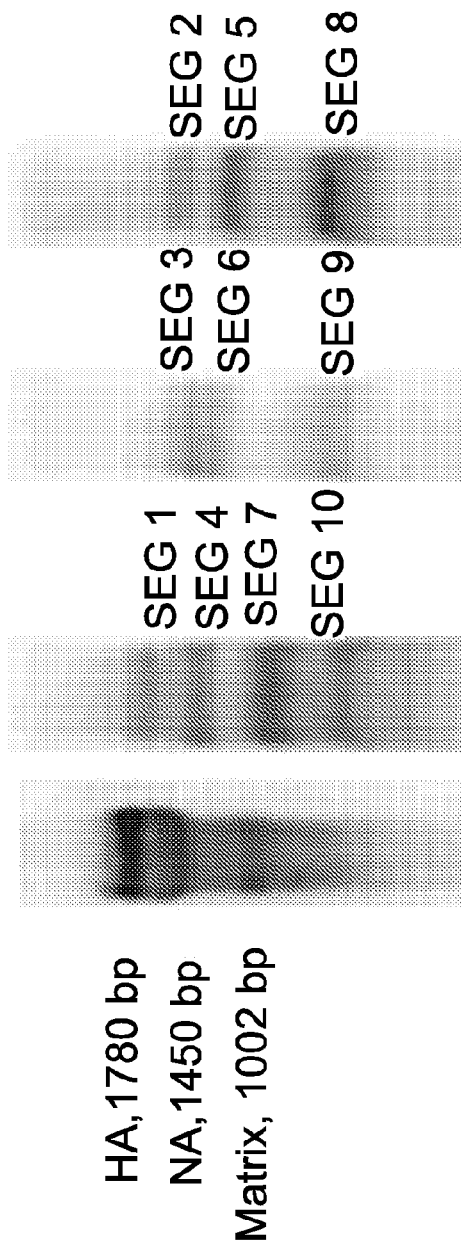
Fig. 5A Influenza A (Ladder) Infected Tilapia Liver RNA (Ecuador)
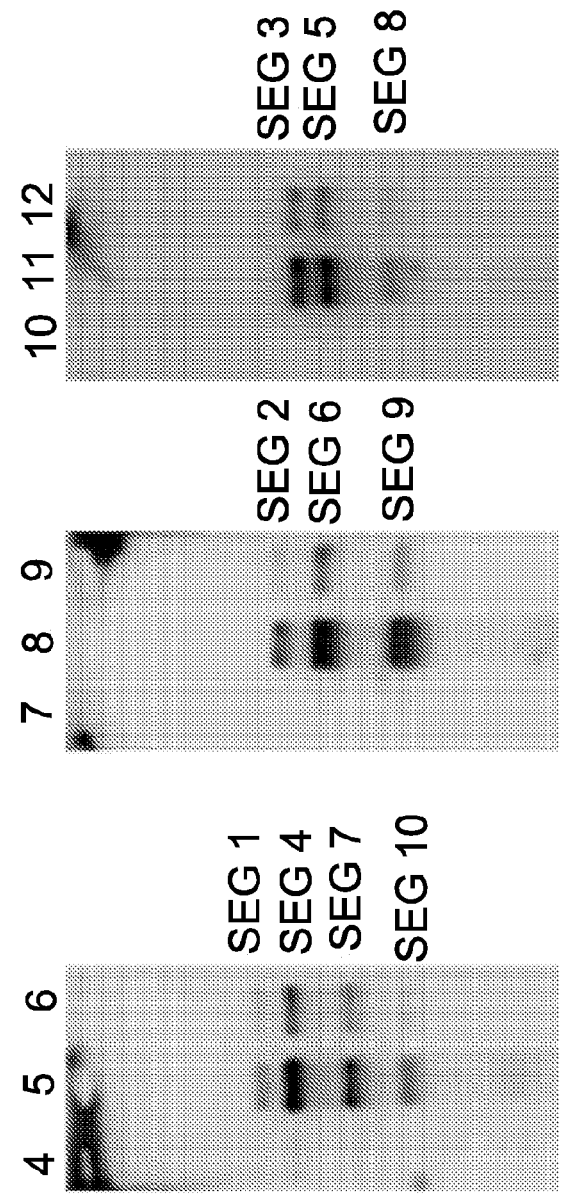
Fig. 5B T

TILAPIA VIRUS AND USES THEREOF

CROSS-REFERENCE TO RELATED APPLICATIONS

The present application is a continuation of U.S. application Ser. No. 16/783,597, filed Feb. 6, 2020, which is a continuation of U.S. application Ser. No. 16/110,432, filed Aug. 23, 2018, now U.S. Pat. No. 10,596,249, issued Mar. 24, 2020. Furthermore, U.S. application Ser. No. 16/110,432 is a continuation of U.S. application Ser. No. 15/536,325, filed Jun. 15, 2017, now U.S. Pat. No. 10,183,072, issued Jan. 22, 20219, which is a U.S. National Phase Application under 35 U.S.C. § 371 of International Patent Application No. PCT/US2015/065795, filed Dec. 15, 2015, which claims priority of U.S. Provisional Application Ser. No. 62/091,824, filed Dec. 15, 2014, each of which is hereby incorporated by reference as if expressly set forth in their respective entirety herein. The International Application was published in English on Jun. 23, 2016 as WO 2016/100328.

FIELD OF THE INVENTION

The invention is in the field of viruses and is related to a new virus found in tilapia, denoted Tilapia Lake Virus (TiLV). The invention includes isolated TiLV, and isolated nucleic acids sequences and polypeptides thereof. The invention also relates to primers and probes. The invention also relates to antibodies against antigens from TiLV. The invention is related to methods for detecting the presence or absence of TiLV in an animal using primers, probes, and antibodies. The invention also relates to iRNAs which target nucleic acid sequences of TiLV. The invention is also related to immunogenic compositions for inducing an immune response against TiLV in an animal.

BACKGROUND OF THE INVENTION

Tilapines are the second most important group of farmed fish worldwide, with production of 2.5 million tons annually (Food and Agriculture Organization 2010), and they serve as a primary protein source in the developing world. The Sea of Galilee (Kinneret Lake) in Israel is one major source of commercial fishing. In recent years, the catch fish quantities have been subjected to a persistent decline.

Although the lake hosts some 27 species of fish, encompassing members of the families Cichlidae, Cyprinidae, Mugillidae, and Claridae, only a decrease in the catch of tilapines (Cichlidae) was noticeable. The main edible fish of the lake, *Sarotherodon* (Tilapia) *galilaeus* (St. Peter's fish), saw annual yields decreased from 316 tons in 2005 to 51, 8, and 45 tons in 2007, 2009, and 2010, respectively.

*S. galilaeus* contributes to the maintenance of the ecological balance of this lake. Hence, beyond its economic impact, the significant decline of St. Peter's fish populations, as well as the other lake tilapines (such as *Tilapia zilli* [common tilapia], *Oreochromis aureus* [Jordan tilapia], and *Tristamella simonis intermedia*) represents a definite threat to the entire ecosystem.

This decrease in the lake tilapine in the Sea of Galilee was due to a serious emerging disease in wild populations of tilapine species, including *S. galilaeus, T. zilli, O. aureus*, and *T. simonis intermedia*, and as well as in the pond-raised hybrid tilapia *O. niloticus* x *O. aureus* in Israel. The association of disease outbreaks with seasonality (May to October, when the water has relatively high temperatures) further indicated the involvement of an infectious agent, since water temperature affects the emergence of a wide range of parasitic, bacterial, and viral diseases of fish. Routine monitoring of known parasites, bacterial, viral pathogens or toxins did not reveal any abnormalities, and no causal agent was identified.

A similar outbreak of disease in tilapia was also found in Ecuador.

Thus, there was a need to identify the causal agent of this decline in tilapia populations in the two different geographical locations, as well as a need for tools and methods for detecting the presence of the causal agent within fish populations and protecting fish populations from the causal agent of this decline. This invention addresses these needs.

SUMMARY OF THE INVENTION

In certain aspects, the invention relates to the finding that the causal agent of the tilapines disease is a novel Tilapia Lake Virus (TiLV) RNA virus. The wide distribution of the virus and the existence of different clinical features of its associated disease make the results described herein of significance to fish farming and wild-life preservation.

In certain aspects, the invention relates to diagnostic tools useful for screening a sample for TiLV.

In certain aspects, the invention described herein relates to vaccines for the protection of fish from viral diseases. In certain aspects, the invention relates to vaccine compositions for the prevention of Tilapia Lake Virus (TiLV)-induced disease in fish, particularly tilapines. In certain aspects invention relates to methods for using the vaccines to protect tilapines from TiLV-induced disease.

The particular aspects, invention is related to isolated TiLV nucleic acid sequences (including cDNA sequences corresponding to sense or anti-sense TiLV RNA sequences) and peptides thereof. The invention is also related to antibodies against antigens derived from TiLV. The invention is also related to iRNAs which target nucleic acid sequences of TiLV. The invention is related to methods for detecting the presence or absence of TiLV in an animal (e.g. in a fish). The invention is also related to immunogenic compositions for inducing an immune response against TiLV in an animal (e.g. in a fish).

In certain aspects, the invention relates to an isolated nucleic acid sequence having the sequence of any of SEQ ID NOs: 1-11, sequences complementary to any of SEQ ID NOs: 1-11, and fragments and variants thereof. In certain embodiments, the nucleic acid is a DNA sequence, including cDNA. In certain embodiments, the nucleic acid is an RNA sequence.

In certain aspects, the invention relates to a synthetic nucleic acid comprising an isolated (or non-isolated) nucleic acid having the sequence of SEQ ID NOs: 1-10, sequences complementary to any of SEQ ID NOs: 1-11, and variants thereof. These synthetic nucleic acids include primers and probes.

In certain aspects, the invention relates to a primer set for determining the presence or absence of TiLV in a biological sample, wherein the primer set comprises at least one synthetic nucleic acid sequence selected from the group consisting of the synthetic nucleic acids described herein.

In certain aspects, the invention relates to a method for determining the presence or absence of TiLV in a biological sample, the method comprising: a) contacting nucleic acid from a biological sample with at least one primer which is a synthetic nucleic acid described herein, b) subjecting the nucleic acid and the primer to amplification conditions, and, c) determining the presence or absence of amplification product, wherein the presence of amplification product indicates the presence of RNA associated with of TiLV the sample.

In certain aspects, the invention relates to oligonucleotide probes for determining the presence or absence of TiLV in a biological sample.

In certain aspects, the invention is directed to iRNA molecules which target nucleic acids from TiLV, for example but not limited to any of SEQ ID NOs: 1-11, and variants thereof, and silence a target gene.

In certain aspects, the invention relates to a method for reducing the levels of a TiLV protein in an animal, viral mRNA in an animal or viral titer in a cell of an animal, the method comprising administering to the animal an iRNA described herein.

In certain aspects, the invention relates to an isolated polypeptide encoded by the nucleic acid of any of SEQ ID NOs: 1-11, nucleic acids with sequences complementary to any of SEQ ID NOs: 1-11, and fragments and variants thereof.

In certain aspects, the invention relates to an isolated polypeptide of SEQ ID NO: 12, and fragments and variants thereof.

In a further aspect, the invention provides a computer readable medium having stored thereon: (i) a nucleic acid sequence selected from the group consisting of: a nucleic acid sequence of any of SEQ ID NOs: 1-11, a sequence substantially identical to a nucleic acid sequence of any of SEQ ID NOs: 1-11, and a sequence variant of a nucleic acid sequence of any of SEQ ID NOs; 1-11; or (ii) an amino acid sequence encoded by a nucleic acid sequence selected from the group consisting of: a nucleic acid sequence of any of SEQ ID NOs: 1-11, a sequence substantially identical to a nucleic acid sequence of any of SEQ ID NOs: 1-11, and a sequence variant of a nucleic acid sequence of any of SEQ ID NOs; 1-11.

In certain aspects, the invention relates to an isolated antibody that specifically binds to a polypeptide of the invention (e.g. a polypeptide of SEQ ID NO: 12 or a polypeptide encoded by any or SEQ ID NOs: 1-11 or sequences complementary thereto or fragments or variants thereof).

In certain aspects, the invention relates to a method for determining whether or not a sample contains TiLV, the method comprising: a) contacting a biological sample with an antibody that specifically binds to a polypeptide of any of an isolated (or non-isolated) polypeptide of SEQ ID NO: 12 or fragments or variants thereof, or a polypeptide encoded by any of SEQ ID NOs: 1-11 or sequences complementary thereto or fragments or variants thereof, and b) determining whether or not the antibody binds to an antigen in the biological sample, wherein binding indicates that the biological sample contains TiLV. In certain embodiments, the determining comprises use of a lateral flow assay or ELISA.

In certain aspects, the invention relates to a method for determining whether or not a biological sample has been infected by TiLV, the method comprising: a) determining whether or not a biological sample contains antibodies that specifically bind to a polypeptide of any of an isolated (or non-isolated) polypeptide of SEQ ID NO: 12 or fragments or variants thereof, or a polypeptide encoded by any or SEQ ID NOs: 1-11 or sequences complementary thereto or fragments or variants thereof.

In certain aspects, the present invention provides immunogenic compositions capable of inducing an immune response against TiLV including TiLV of the invention comprising a nucleic acid of any of SEQ ID NOs: 1-11 or fragments or variants thereof, or comprising a cDNA sequence complementary to the sense or an anti-sense strand of any of SEQ ID NOs: 1-11 or fragments or variants thereof, or comprising a polypeptide encoded by any of SEQ ID NOs: 1-11, or a cDNA sequence complementary to the sense or an anti-sense strand of any of SEQ ID NOs: 1-11, or comprising a polypeptide comprising SEQ ID NO: 12 or fragments or variants thereof, or comprising a killed or attenuated TiLV.

In certain aspects, the invention relates to a method of inducing an immune response in an animal, the method comprising administering an immunogenic composition described herein.

In another aspect, the invention provides a method for preventing or reducing TiLV infection in an animal, the method comprising administering a TiLV immunogenic composition described herein.

In another aspect, the invention provides a method for preventing or reducing TiLV infection in an animal, the method comprising administering a TiLV antibody described herein.

In one embodiment, the method of administration is oral, immersion or injection.

In another aspect, the invention provides for use of any of the immunogenic compositions described herein in the manufacture of a vaccine for the treatment or prevention of TiLV infection in an animal.

In certain aspects, the invention relates to an isolated virus comprising at least 24 consecutive nucleotides from an isolated (or non-isolated) nucleic acid having the sequence of any of SEQ ID NOs: 1-11; an isolated (or non-isolated) nucleic acid complementary to the sequence of any of SEQ ID NOs: 1-11; an isolated (or non-isolated) nucleic acid having at least about 60% sequence identity to any of SEQ ID NOs: 1-11; or an isolated (or non-isolated) nucleic acid having at least about 60% sequence identity to a nucleic acid complementary to the sequence of any of SEQ ID NOs: 1-11.

In certain aspects, the invention relates to an isolated virus comprising at least 8 consecutive amino acids from the polypeptide encoded by an isolated (or non-isolated) nucleic acid having the sequence of any of SEQ ID NOs: 1-11; an isolated (or non-isolated) nucleic acid complementary to the sequence of any of SEQ ID NOs: 1-11; an isolated (or non-isolated) nucleic acid having at least about 60% sequence identity to any of SEQ ID NOs: 1-11; or an isolated (or non-isolated) nucleic acid having at least about 60% sequence identity to a nucleic acid complementary to the sequence of any of SEQ ID NOs: 1-11.

In certain aspects, the invention relates to an isolated cell comprising an isolated (or non-isolated) nucleic acid having the sequence of any of SEQ ID NOs: 1-11, sequences complementary to SEQ ID NOs: 1-11 and fragments and variant thereof described herein.

In certain aspects, the invention relates to a method for culturing cells comprising: a) infecting a cell with TiLV, or an isolated (or non-isolated) nucleic acid having the sequence of any of SEQ ID NOs: 1-11, sequences complementary to SEQ ID NOs: 1-11 and fragments and variant thereof described herein, and b) culturing the cells.

In certain aspects, the invention relates to a method of testing a TiLV vaccine, comprising: a) contacting cells with a TiLV vaccine; b) contacting cells with TiLV; and c) measuring the number of cells infected with TiLV.

In certain aspects, the invention relates to a method of testing a TiLV drug, comprising: a) contacting cells with a TiLV drug; b) contacting cells with TiLV; and c) measuring the number of cells infected with TiLV.

In certain aspects, the invention relates to a method of testing a TiLV drug, comprising: a) contacting cells with TiLV; b) contacting cells with a TiLV drug; and c) measuring the replication of TiLV.

In other aspects, the invention provides methods for identifying and/or generating anti-viral drugs. For example, in one aspect the invention provides methods for identifying drugs that bind to and/or inhibit the function of TiLV-encoded proteins of the invention, or that inhibit the replication or pathogenicity of TiLV of the invention. Methods of identifying drugs that affect or inhibit a particular drug target, such as high throughput drug screening methods, are well known in the art and can readily be applied to the proteins and viruses of the present invention.

The present invention also provides for methods and tools for drug design, testing of agents, and tools for basic research into the causes and etiology of TiLV.

BRIEF DESCRIPTION OF THE FIGURES

For the purpose of illustrating the invention, there are depicted in drawings certain embodiments of the invention. However, the invention is not limited to the precise arrangements and instrumentalities of the embodiments depicted in the drawings.

FIG. 1 shows characteristics of tilapia disease and pathological findings in commercial hybrid tilapia (*O. niloticus* x *O. aureus* hybrid) (FIG. 1A and FIG. 1C to FIG. 1E) and in wild tilapia (*S. galilaeus*) from the Sea of Galilee (FIG. 1B and FIG. 1F to FIG. 1H). FIG. 1E shows hematoxylin and eosin stain of brain and cortex. The arrows mark dilated blood vessels packed with large numbers of red blood cells within the leptomeninges and gray and white matter. H&E stain×10 was used. FIG. 1F shows hematoxylin and eosin stain of brain and cortex. Perivascular cuffs of lymphocytes are encircled. H&E stain×40 was used. FIG. 1Ga shows shows hematoxylin and eosin stain of lens. Cataractous changes are characterized by formation of eosinophilic spherical structures (morgagnian globules) accompanied by degeneration of crystalline fibers (encircled). H&E stain×10 was used. FIG. 1Gb show shows hematoxylin and eosin stain of control lens from healthy fish. H&E stain×10 was used. FIG. 1H shows shows hematoxylin and eosin stain of eye and cornea. Loss of integrity of the overlying squamous epithelium with inflammatory infiltrate (arrowheads) and multiple capillaries within the stroma (neovascularization; encircled). The collagen fibers within the superficial stroma are smudged and are stained pale eosinophilic (corneal edema). H&E stain×10 was used.

FIG. 2 shows cytopathogenic effect or CPE induction in infected cultures and electron microscopy (EM) analyses. FIG. 2A shows images of E-11 infected cells with CPE at day 5 postinoculation. Plaque formation and vacuolated cells are shown at the rims of the plaques. The centers of two plaques are marked with asterisks. FIG. 2B shows images of infected primary tilapia brain cells with CPE at day 10 postinoculation. Conversion of the typical elongated cells into swollen, rounded, and granulated cells is marked with arrows. FIG. 2C and FIG. 2D are images of controls, mock-infected E-11 or primary tilapia brain, respectively. FIG. 2E and FIG. 2F are transmission EM of thin sections of infected E-11 cells with electron-dense particles (diameter, 55 to 60 nm) aggregated and enclosed in the intracytoplasmic membrane (FIG. 2E, marked with an arrow) or within the cytoplasm (FIG. 2F). Scale bars, 200 and 500 nm for FIG. 2E and FIG. 2F, respectively. FIG. 2G is an EM image of negatively stained virions, pelleted from infected E11 culture supernatants. Scale bar, 100 nm.

FIG. 3 shows PCR detection of TiLV.

FIG. 5 shows Northern Blot analysis of nucleic acids from diseased tilapia in Israel and Ecuador. FIG. 5A shows Northern Blot analysis of total RNA extracted from diseased Ecuadorian tilapia liver and analyzed with three mixes of probes representing segments 1, 4, 7, and 10 (Combo 1); 3, 6, and 9 (Combo 2); or 2, 5, and 8 (Combo 3) to prevent signal overlap from similar sized segments (three right-hand panels). Influenza A virus RNA hybridized with three probes representing HA, NA, and matrix proteins served as size references (left panel). FIG. 5B shows Northern Blot analysis of total RNA extracted from culture cells infected with brain derived TiLV from Israeli tilapia or from culture supernatant and analyzed with the three mixes of probes. Lanes 5, 8, and 11 show results from extracts from infected culture cells (6 dpi); lanes 6, 9, and 12 show results from extracts from infected culture supernatant; lanes 4, 7, and 10 show results from extracts from non-infected culture cells.

FIG. 7 shows the results of real-time PCR.

DETAILED DESCRIPTION OF THE INVENTION

Figure 1A:
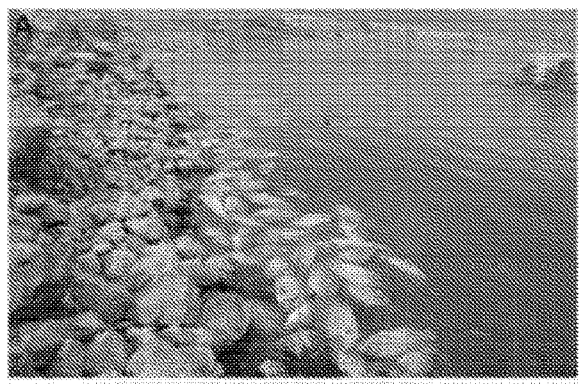
FIG. 1A is a photograph showing tilapia disease outbreak in a commercial pond resulting in massive mortality (August 2013).

Tilapines are important for the sustainability of ecological systems and serve as the second most important group of farmed fish worldwide. The invention described herein relates to the observation of significant mortality of wild and cultured tilapia both in Israel and Ecuador.

Reported herein is the isolation of a previously undescribed virus, designated Tilapia Lake Virus or TiLV, from spontaneously diseased fish and the induction of disease in tilapia by this agent. The incubation of extracts from diseased, but not healthy, tilapines with cultures of fish cells (E-11 and primary tilapia brain cells) resulted in the appearance of cytopathogenic effect or CPE in infected cultures. Moreover, the inoculation of supernatants, harvested from these cultures, into naive tilapines resulted in the appearance of disease. TiLV was reisolated in cell cultures from experimentally infected fish, and the agent induced a similar disease upon inoculation of new naive fish. Furthermore, an experimentally induced disease was achieved with a purified TiLV obtained by endpoint dilutions. Of note, the signs of the naturally occurring disease (discoloration, skin patches, ocular alterations, and lethargy) were observed in the experimentally induced disease. The TiLV sequences were amplified from diseased fish and TiLV-infected cell cultures but not from naive fish, mock-infected cultures, or cultures infected by another agent (VNN).

Several lines of evidence indicated that this infectious agent is a virus. First, the agent went through 0.2 □m filters while retaining its infectivity, ruling out the possibility of infection by microorganisms larger than this filter size (such as bacteria and fungi). Second, the appearance of CPE after serial passages of the agent in cell cultures excludes the possibility of a filterable toxin-induced CPE. Third, virion-like structures were visualized by EM in infected cells and in the supernatants of cultures of these cells. Fourth, CPE activity was demonstrated for relatively dense fractions of sucrose gradients, similar to known assembled virions. Fifth, the encapsidated TiLV genome is made of RNA, as evidenced by the fact that it was amplified by RT-PCR only (and not by PCR) from samples of sick fish and from cell cultures that were inoculated with extracts of such fish, as well as by the fact that this amplification was sensitive to initial digestion with RNase I. RNA genomes are only known to occur for viruses. EM analyses and the sensitivity of TiLV to organic solvents (ether or chloroform) further indicate that TiLV is an enveloped virus.

TiLV-induced disease in tilapines was achieved either by intraperitoneal (i.p.) injections or by cohabitation. The cohabitation mode of transmission demonstrates the ability of TiLV to spread by the waterborne route. It should be noted that in these experiments, relatively high mortality rates were observed for both the i.p. and waterborne routes.

The existence of fish that survived the TiLV-induced disease strongly indicated that an effective immune response against this pathogen can be mounted. This has important applications for future disease containment strategies. Besides the possibility of vaccine development, the determination of the susceptibility of different tilapia species to TiLV should be considered a measure of disease containment. This notion is based on the well-documented differences in disease resistance among species of the same genus.

This work also provides molecular characterization of TiLV isolated from diseased fish in both Israel and Ecuador. Ten segments of the TiLV genome were identified from virus in fish from both venues, resulting in SEQ ID NOs: 1-11. (SEQ ID NO: 1 is a shorter version of SEQ ID NO: 9—both are segment 3 of the TiLV genome). Homology searches in the NCBI database yielded a single hit for segment 1 of the genome (SEQ ID NO: 7) that indicated a very distant homology to orthomyxoviral RNA-dependent RNA polymerase. This further indicates that TiLV is a new emerging pathogen for tilapia. In light of the extensive commercial production of tilapia and the fact that tilapia serves as a primary protein source in the developing world, it is highly important to diagnose this new pathogen. The amplification of TiLV sequences from diseased fish and TiLV-infected cultures, described in this work, provides the basis for a PCR-based diagnosis, allowing prompt screening, surveillance, epidemiological studies, and disease containment. Additionally, the TiLV sequences can be used for vaccines, i.e., immunological compositions, for inducing immune responses against TiLV in tilapia populations.

The TiLV identified herein is a novel RNA virus. Thus, cDNA nucleic acid sequences do not exist in nature. In other words, the nucleic acid sequences of SEQ ID NO: 1-11 are non-naturally occurring compositions that are markedly different in structure than naturally occurring TiLV RNA sequences. Additionally any embodiments of the invention such as primers, probes, antibodies, immunogenic compositions and cells and cell lines, comprising the nucleic acids of SEQ ID NOs: 1-11 would also not naturally occur.

In certain aspects, the invention relates to the finding that the etiological agent of this disease is a novel RNA virus. In certain aspects, the invention also relates to the methods useful for isolating and detecting the virus. As is described further herein, the virus, denominated Tilapia Lake Virus (TiLV), can be propagated in primary tilapia brain cells or in an E-11 cell line. In certain aspects, the invention relates to the finding that the virus can induce a cytopathic effect at 5 to 10 days postinfection. In certain aspects, the invention relates to electron microscopy findings showing the presence of enveloped icosahedral particles of 55 to 75 nm. In certain aspects, the invention relates to the finding that low-passage TiLV, injected intraperitoneally in tilapia, induced a disease resembling the natural disease, which typically presents with lethargy, ocular alterations, and skin erosions, with greater than 80% mortality.

In certain aspects, the invention relates to the finding that histological changes included congestion of the internal organs (kidneys and brain) with foci of gliosis and perivascular cuffing of lymphocytes in the brain cortex; ocular inflammation included endophthalmitis and cataractous changes of the lens. In certain aspects, the invention relates to the finding that the cohabitation of healthy and diseased fish demonstrated that the disease is contagious and that mortalities (80 to 100%) occur within a few days. In certain aspects, the invention relates to the finding that fish surviving the initial mortality were immune to further TiLV infections, indicating the mounting of a protective immune response.

In certain aspects, the invention relates to the finding that screening cDNA libraries identified a TiLV-specific sequence, allowing the design of a PCR-based diagnostic test. In certain aspects, the invention relates to testing enabling the specific identification of TiLV in tilapines. Such testing is helpful for controlling the spread of this virus worldwide.

Definitions

The terms used in this specification generally have their ordinary meanings in the art, within the context of this invention and the specific context where each term is used. Certain terms are discussed below, or elsewhere in the specification, to provide additional guidance to the practitioner in describing the methods of the invention and how to use them. Moreover, it will be appreciated that the same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of the other synonyms. The use of examples anywhere in the specification, including examples of any terms discussed herein, is illustrative only, and in no way limits the scope and meaning of the invention or any exemplified term. Likewise, the invention is not limited to its preferred embodiments.

In accordance with the present invention, there may be numerous tools and techniques within the skill of the art, such as those commonly used in molecular immunology, cellular immunology, pharmacology, and microbiology. See, e.g., Sambrook et al. (2001) *Molecular Cloning: A Laboratory Manual.* 3rd ed. Cold Spring Harbor Laboratory Press: Cold Spring Harbor, N.Y.; Ausubel et al. eds. (2005) *Current Protocols in Molecular Biology*, John Wiley and Sons, Inc.: Hoboken, N.J.; Bonifacino et al. eds. (2005) *Current Protocols in Cell Biology*, John Wiley and Sons, Inc.: Hoboken, N.J.; Coligan et al. eds. (2005) *Current Protocols in Immunology*, John Wiley and Sons, Inc.: Hoboken, N.J.; Coico et al. eds. (2005) *Current Protocols in Microbiology*, John Wiley and Sons, Inc.: Hoboken, N.J.; Coligan et al. eds. (2005) *Current Protocols in Protein Science*, John Wiley and Sons, Inc.: Hoboken, N.J.; and Enna et al. eds. (2005) *Current Protocols in Pharmacology*, John Wiley and Sons, Inc.: Hoboken, N.J.

The singular forms "a," "an," and "the" include plural reference unless the context clearly dictates otherwise.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

As used herein, "TiLV" refers to isolates of the Tilapia Lake Virus described herein.

As used herein, a "TiLV gene" refers to any one of the genes or gene segments as described in SEQ ID Nos: 1-11, identified in the TiLV genome.

As used herein, the term "animal" refers to a vertebrate, including, but not limited to, fish, (e.g. tilapia).

"Substantially identical," in the context of two nucleic acids or polypeptides, refers to two or more sequences or subsequences that have at least 98%, at least 99% or higher nucleotide or amino acid residue identity, when compared and aligned for maximum correspondence, as measured using one of the following sequence comparison algorithms or by visual inspection.

"Percent identity" in the context of two or more nucleic acids or polypeptide sequences, refers to the percentage of nucleotides or amino acids that two or more sequences or subsequences contain which are the same. A specified percentage of nucleotides can be referred to such as: 60% identity, 65%, 70%, 75%, 80%, 85%, 90%, 91%, 92%, 93%, 94%, 95%, 96%, 97%, 98%, or 99% or more identity over a specified region, when compared and aligned for maximum correspondence over a comparison window, or designated region as measured using one of the following sequence comparison algorithms or by manual alignment and visual inspection.

A "comparison window", as used herein, includes reference to a segment of any one of the number of contiguous positions selected from the group consisting of from 20 to 600, usually about 50 to about 200, more usually about 100 to about 150 in which a sequence can be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith and Waterman (1981) *Adv. Appl. Math.* 2: 482, by the homology alignment algorithm of Needleman and Wunsch (1970) *J. Mol. Biol.* 48: 443, by the search for similarity method of Pearson and Lipman (1988) *Proc. Natl. Acad. Sci. U.S.A.* 85: 2444, by computerized implementations of these algorithms (FASTDB (Intelligenetics), BLAST (National Center for Biomedical Information), GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel).

In the context of nucleic acids base symbols can be used to represent a position on a nucleic acid sequence that can have multiple possible alternative. For example, "W" represents A or T; "S" represents C or G; "M" represents A or C; "K" represents G or T; "R" represents A or G; "Y" represents C or T; "B" represents C, G, or T; "D" represents A, G, or T; "H" represents A, C, or T; "V" represents A, C, or G.

It will be understood that, for the particular TiLV polypeptides described here, natural variations can exist between individual TiLV strains. These variations may be demonstrated by (an) amino acid difference(s) in the overall sequence or by deletions, substitutions, insertions, inversions or additions of (an) amino acid(s) in said sequence Amino acid substitutions which do not essentially alter biological and immunological activities, have been described, e.g. by Neurath et al in "The Proteins" Academic Press New York (1979). Amino acid replacements between related amino 15 acids or replacements which have occurred frequently in evolution are, inter alia, Ser/Ala, Ser/Gly, Asp/Gly, Asp/Asn, Ile/Val (see Dayhof, M. D., Atlas of protein sequence and structure, *Nat. Biomed. Res. Found.*, Washington D.C., 1978, vol. 5, suppl. 3). Other amino acid substitutions include Asp/Glu, Thr/Ser, Ala/Gly, Ala/Thr, Ser/Asn, Ala/Val, Thr/Phe, Ala/Pro, Lys/Arg, Leu/Ile, Leu/Val and Ala/Glu. Based on this information, Lipman and Pearson developed a method for rapid and sensitive protein comparison (*Science* (1985) 227:1435) and determining the functional similarity between homologous proteins. Such amino acid substitutions of the exemplary embodiments of this invention, as well as variations having deletions and/or insertions are within the scope of the invention as long as the resulting proteins retain their immune reactivity. It is know that polypeptide sequences having one or more amino acid sequence variations as compared to a reference polypeptide may still be useful for generating antibodies that bind the reference polypeptide.

Nucleic Acids and Uses Thereof

The present invention provides TiLV nucleic acid sequences. These nucleic acid sequences may be useful for, inter alia, expression of TiLV-encoded proteins or fragments, variants, or derivatives thereof, generation of antibodies against TiLV proteins, generation of primers and probes for detecting TiLV and/or for diagnosing TiLV infection, generating immunogenic compositions against TiLV, and screening for drugs effective against TiLV as described herein.

In certain aspects, the TiLV nucleic acid sequences are provided in SEQ ID NOs: 1-11, corresponding to TiLV genome segments (see Table 2).

In certain aspects, the invention is directed to a TiLV isolated nucleic acid sequence as provided in any of SEQ ID NOs: 1-11

In certain aspects, the invention is directed to an isolated nucleic acid complementary to any of SEQ ID NOs: 1-11.

In certain aspects, the invention relates to variants of TiLV nucleic acid sequence having greater that 60% similarity to the sequence of any of SEQ ID NOs: 1-11.

In certain aspects, the invention is directed to isolated nucleic acid sequence variants of any of SEQ ID NOs: 1-11 and fragments thereof. Variants of any of SEQ ID NOs: 1-11 include, but are not limited to, nucleic acid sequences having at least from about 50% to about 55% identity to that of any of SEQ ID NOs: 1-11. Variants of any of SEQ ID NOs: 1-11 include, but are not limited to, nucleic acid sequences having at least from about 55.1% to about 60% identity to that of any of SEQ ID NOs: 1-11. Variants of any of SEQ ID NOs: 1-11 include, but are not limited to, nucleic acid sequences having at least from about 60.1% to about 65% identity to that of any of SEQ ID NOs: 1-11. Variants of any of SEQ ID NOs: 1-11 include, but are not limited to, nucleic acid sequences having at least from about 65.1% to about 70% identity to that of any of SEQ ID NOs: 1-11. Variants of any of SEQ ID NOs: 1-11 include, but are not limited to, nucleic acid sequences having at least from about 70.1% to about 75% identity to that of any of SEQ ID NOs: 1-11. Variants of any of SEQ ID NOs: 1-11 include, but are not limited to, nucleic acid sequences having at least from about 75.1% to about 80% identity to that of any of SEQ ID NOs: 1-11. Variants of any of SEQ ID NOs: 1-11 include, but are not limited to, nucleic acid sequences having at least from about 80.1% to about 85% identity to that of any of SEQ ID NOs: 1-11. Variants of any of SEQ ID NOs: 1-11 include, but are not limited to, nucleic acid sequences having at least from about 85.1% to about 90% identity to that of any of SEQ ID NOs: 1-11. Variants of any of SEQ ID NOs: 1-11 include, but are not limited to, nucleic acid sequences having at least from about 90.1% to about 95% identity to that of any of SEQ ID NOs: 1-11. Variants of any of SEQ ID NOs: 1-11 include, but are not limited to, nucleic acid sequences having about 95.1%, about 95.5%, about 96%, about 96.5%, about 97%, about 97.5%, about 98%, about 98.5%, about 99%, about 99.5% or about 99.9% identity to that of any of SEQ ID NOs: 1-11. Programs and algorithms for sequence alignment and comparison of % identity and/or homology between nucleic acid sequences are well known in the art, and include BLAST, SIM alignment tool, and so forth.

In a further embodiment, the invention provides an isolated nucleic acid having a sequence substantially identical to a nucleic acid of any of SEQ ID NOs: 1-11, or a fragment thereof. In a further embodiment, the invention provides an isolated nucleic acid having a sequence substantially identical to a nucleic acid complementary to any of SEQ ID NOs: 1-11, or a fragment thereof.

In one embodiment, the invention is directed to an isolated nucleic acid sequence comprising from about 10 to about 50 consecutive nucleotides from any one or SEQ ID NOs: 1-11 or a sequence complementary to any one of SEQ ID NOs: 1-11 or a variant thereof. In one embodiment, the invention is directed to an isolated nucleic acid sequence comprising from about 10 to about 100 consecutive nucleotides from any one or SEQ ID NOs: 1-11 or a sequence complementary to any one of SEQ ID NOs: 1-11 or a variant thereof. In one embodiment, the invention is directed to an isolated nucleic acid sequence comprising from about 10 to about 200 consecutive nucleotides from any one or SEQ ID NOs: 1-11 or a sequence complementary to any one of SEQ ID NOs: 1-11 or a variant thereof. In one embodiment, the invention is directed to an isolated nucleic acid sequence comprising from about 10 to about 300 consecutive nucleotides from any one or SEQ ID NOs: 1-11 or a sequence complementary to any one of SEQ ID NOs: 1-11 or a variant thereof. In one embodiment, the invention is directed to an isolated nucleic acid sequence comprising from about 10 to about 400 consecutive nucleotides from any one or SEQ ID NOs: 1-11 or a sequence complementary to any one of SEQ ID NOs: 1-11 or a variant thereof. In one embodiment, the invention is directed to an isolated nucleic acid sequence comprising from about 10 to about 500 consecutive nucleotides from any one or SEQ ID NOs: 1-11 or a sequence complementary to any one of SEQ ID NOs: 1-11 or a variant thereof. In one embodiment, the invention is directed to an isolated nucleic acid sequence comprising from about 10 to about 600 consecutive nucleotides from any one or SEQ ID NOs: 1-11 or a sequence complementary to any one of SEQ ID NOs: 1-11 or a variant thereof. In one embodiment, the invention is directed to an isolated nucleic acid sequence comprising from about 10 to about 700 consecutive nucleotides from any one or SEQ ID NOs: 1-11 or a sequence complementary to any one of SEQ ID NOs: 1-11 or a variant thereof. In one embodiment, the invention is directed to an isolated nucleic acid sequence comprising from about 10 to about 800 consecutive nucleotides from any one or SEQ ID NOs: 1-11 or a sequence complementary to any one of SEQ ID NOs: 1-11 or a variant thereof. In one embodiment, the invention is directed to an isolated nucleic acid sequence comprising from about 10 to about 900 or more consecutive nucleotides from any one or SEQ ID NOs: 1-11 or a sequence complementary to any one of SEQ ID NOs: 1-11 or a variant thereof. In one embodiment, the invention is directed to an isolated nucleic acid sequence comprising from about 10 to about 1000 or more consecutive nucleotides from any one or SEQ ID NOs: 1-11 or a sequence complementary to any one of SEQ ID NOs: 1-11 or a variant thereof. In one embodiment, the invention is directed to an isolated nucleic acid sequence comprising from about 10 to about 1200 or more consecutive nucleotides from any one or SEQ ID NOs: 1-11 or a sequence complementary to any one of SEQ ID NOs: 1-11 or a variant thereof. In one embodiment, the invention is directed to an isolated nucleic acid sequence comprising from about 10 to about 1400 or more consecutive nucleotides from any one or SEQ ID NOs: 1-11 or a sequence complementary to any one of SEQ ID NOs: 1-11 or a variant thereof. In one embodiment, the invention is directed to an isolated nucleic acid sequence comprising from about 10 to about 1640 or more consecutive nucleotides from any one or SEQ ID NOs: 1-11 or a sequence complementary to any one of SEQ ID NOs: 1-11 or a variant thereof.

Encompassed by the invention are polynucleotide sequences that are capable of hybridizing to the claimed polynucleotide sequences, including any of the nucleic acid sequences disclosed herein, and fragments thereof under various conditions of stringency Polynucleotides homologous to the sequences illustrated in SEQ ID NOs: 1-11, can be identified, e.g., by hybridization to each other under stringent or under highly stringent conditions. The term "nucleic acid hybridization" refers to anti-parallel hydrogen bonding between two single-stranded nucleic acids, in which A pairs with T (or U if an RNA nucleic acid) and C pairs with G. Nucleic acid molecules are "hybridizable" to each other when at least one strand of one nucleic acid molecule can form hydrogen bonds with the complementary bases of another nucleic acid molecule under defined stringency conditions. The stringency of a hybridization reflects the degree of sequence identity of the nucleic acids involved, such that the higher the stringency, the more similar are the two polynucleotide strands. Stringency of hybridization is determined, e.g., by (i) the temperature at which hybridization and/or washing is performed, and (ii) the ionic strength and (iii) concentration of denaturants such as formamide of the hybridization and washing solutions, as well as other parameters. Hybridization requires that the two strands contain substantially complementary sequences. Depending on the stringency of hybridization, however, some degree of mismatches may be tolerated. Under "low stringency" conditions, a greater percentage of mismatches are tolerable (i.e., will not prevent formation of an anti-parallel hybrid). Hybridization conditions for various stringencies are known in the art and are disclosed in detail in at least Sambrook et al.

In certain aspects, the invention relates to a synthetic nucleic acid comprising the nucleotides of an isolated (or non-isolated) nucleic acid having the sequence of any of SEQ ID NOs: 1-11; an isolated (or non-isolated) nucleic acid complementary to the sequence of any of SEQ ID NOs: 1-11; an isolated (or non-isolated) nucleic acid having at least about 60% sequence identity to any of SEQ ID NOs: 1-11; an isolated (or non-isolated) nucleic acid having at least about 60% sequence identity to a nucleic acid complementary to the sequence of any of SEQ ID NOs: 1-11; an isolated (or non-isolated) nucleic acid which comprises at least 10 consecutive nucleotides of any of SEQ ID NOs: 1-11; an isolated (or non-isolated) nucleic acid which comprises at least 10 consecutive nucleotides of a nucleic acid complementary to the sequence of any of SEQ ID NOs: 1-11; an isolated (or non-isolated) nucleic acid which comprises at least 10 consecutive nucleotides of a sequence having at least about 60% identity to any of SEQ ID NOs: 1-11; or an isolated (or non-isolated) nucleic acid which comprises at least 10 consecutive nucleotides of a sequence having at least about 60% identity to a nucleic acid complementary to the sequence of any of SEQ ID NOs: 1-11.

In yet another aspect, the invention provides a synthetic nucleic acid which has a sequence consisting of from about 10 to about 30 consecutive nucleotides from a nucleic acid sequence selected from the group of sequence consisting of SEQ ID NOs: 1-11.

In yet another aspect, the invention provides a synthetic nucleic acid which has a sequence consisting of from about 10 to about 30 consecutive nucleotides consisting of consecutive nucleotides having a sequence which is a variant of any of SEQ ID NOs: 1-11 having at least about 95.1%, about 95.5%, about 96%, about 96.5%, about 97%, about 97.5%, about 98%, about 98.5%, about 99%, about 99.5% or about 99.9% identity to that of any of SEQ ID NOs: 1-11.

In yet another aspect, the invention provides a composition comprising one or more nucleic acids which has a sequence consisting of from about 10 to about 30 consecutive nucleotides from a nucleic acid sequence selected from the group of sequence consisting of SEQ ID NOs: 1-11.

In yet another aspect, the invention provides a composition comprising one or more nucleic acids which has a sequence consisting of from about 10 to about 30 consecutive nucleotides consisting of consecutive nucleotides having a sequence which is a variant of any of SEQ ID NOs: 1-11 having at least about 95.1%, about 95.5%, about 96%, about 96.5%, about 97%, about 97.5%, about 98%, about 98.5%, about 99%, about 99.5% or about 99.9% identity to that of any of SEQ ID NOs: 1-11.

In yet another aspect, the invention provides a synthetic nucleic acid which has a sequence consisting of from about 10 to about 30 consecutive nucleotides from a nucleic acid sequence which is complementary to a nucleic acid sequence selected from the group of sequence consisting of SEQ ID NOs: 1-11.

In yet another aspect, the invention provides a synthetic nucleic acid which has a sequence consisting of from about 10 to about 30 consecutive nucleotides which is complementary to a nucleic acid consisting of consecutive nucleotides having a sequence which is a variant of any of SEQ ID NOs: 1-11 having at least about 95.1%, about 95.5%, about 96%, about 96.5%, about 97%, about 97.5%, about 98%, about 98.5%, about 99%, about 99.5% or about 99.9% identity to that of any of SEQ ID NOs: 1-11.

In yet another aspect, the invention provides a composition comprising one or more nucleic acids which has a sequence consisting of from about 10 to about 30 consecutive nucleotides from a nucleic acid sequence which is complementary to a nucleic acid sequence selected from the group of sequence consisting of SEQ ID NOs: 1-11.

In yet another aspect, the invention provides a composition comprising one or more nucleic acids which has a sequence consisting of from about 10 to about 30 consecutive nucleotides which is complementary to a nucleic acid consisting of consecutive nucleotides having a sequence which is a variant of any of SEQ ID NOs: 1-11 having at least about 95.1%, about 95.5%, about 96%, about 96.5%, about 97%, about 97.5%, about 98%, about 98.5%, about 99%, about 99.5% or about 99.9% identity to that of any of SEQ ID NOs: 1-11.

In other aspects the invention is directed to isolated nucleic acid sequences such as primers and probes, comprising nucleic acid sequences of any of SEQ ID NOs: 1-11. Such primers and/or probes may be useful for detecting the presence of TiLV of the invention, for example in samples of bodily fluids such as blood, saliva, or urine from an animal, and thus may be useful in the diagnosis of TiLV infection. Such probes can detect polynucleotides of any of SEQ ID NOs: 1-11 in samples which comprise TiLV represented by any of SEQ ID NOs: 1-11. The isolated nucleic acids which can be used as primer and probes are of sufficient length to allow hybridization with, i.e. formation of duplex with a corresponding target nucleic acid sequence, a nucleic acid sequences of any of SEQ ID NOs: 1-11, or a fragment or variant thereof.

The isolated nucleic acid of the invention which can be used as primers and/or probes can comprise from about 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 40, 45, 50, 55, 60, 65, 70, 75, 80, 85, 90, 95 and 100 consecutive nucleotides from any of SEQ ID NOs: 1-11, or sequences complementary to any of SEQ ID NOs: 1-11 or variants thereof. The invention is also directed to primer and/or probes which can be labeled by any suitable molecule and/or label known in the art, for example but not limited to fluorescent tags suitable for use in Real Time PCR amplification, for example TaqMan, cybergreen, TAMRA and/or FAM probes; radiolabels, and so forth. In certain embodiments, the oligonucleotide primers and/or probe further comprises a detectable non-isotopic label selected from the group consisting of: a fluorescent molecule, a chemiluminescent molecule, an enzyme, a cofactor, an enzyme substrate, and a hapten.

In another aspect, the invention provides an oligonucleotide probe which comprises from about 10 to about 50 nucleotides, wherein at least about 10 contiguous nucleotides are at least 95% complementary to a nucleic acid target region within a TiLV nucleic acid sequence in any of SEQ ID NOs: 1-11, wherein the oligonucleotide probe hybridizes to the nucleic acid target region under moderate to highly stringent conditions to form a detectable nucleic acid target: oligonucleotide probe duplex. In one embodiment, the oligonucleotide probe is at least about 95.5%, about 96%, about 96.5%, about 97%, about 97.5%, about 98%, about 98.5%, about 99%, about 99.5% or about 99.9% complementary to SEQ ID NOs: 1-11. In another embodiment the oligonucleotide probe consists essentially of from about 10 to about 50 nucleotides.

In certain aspects, the invention is directed to primer sets comprising isolated nucleic acids as described herein, which primer sets are suitable for amplification of nucleic acids from samples which comprises TiLV represented by any one of SEQ ID NOs: 1-11, or variants thereof. Primer sets can comprise any suitable combination of primers which would allow amplification of a target nucleic acid sequences in a sample which comprises TiLV represented any of SEQ ID NOs: 1-11, or variants thereof. Amplification can be performed by any suitable method known in the art, for example but not limited to PCR, RT-PCR, transcription mediated amplification (TMA).

In certain aspects, the invention relates to a primer set for determining the presence or absence of TiLV in a biological sample, wherein the primer set comprises at least one synthetic nucleic acid sequence selected from the group consisting of the synthetic nucleic acid described herein.

In certain aspects, the invention provides a primer set for determining the presence or absence of TiLV in a biological sample, wherein the primer set comprises at least one synthetic nucleic acid sequence selected from the group consisting of: a synthetic nucleic acid which has a sequence consisting of from about 10 to about 30 consecutive nucleotides from a nucleic acid sequence selected from the group of sequence consisting of SEQ ID NOs: 1-11 or variants thereof as described herein; or a synthetic nucleic acid which has a sequence consisting of from about 10 to about 30 consecutive nucleotides from a nucleic acid sequence which is complementary to a nucleic acid sequence selected from the group of sequence consisting of SEQ ID NOs: 1-11 or variants thereof as described herein.

Primer sets can be designed by those of skill in the art using the sequences of SEQ ID NOs: 1-11. Examples of primer pairs useful for the detection methods using PCR are:

ME1 (SEQ ID NO: 23) and clone 7450/150R (SEQ ID NO: 16);
Nested ext-1 (SEQ ID NO: 24) and nested ext-2 (SEQ ID NO: 25);
NM-CLU7-SF1 (SEQ ID NO: 28) and NM-CLU7-SRI (SEQ ID NO: 29);
TiLV-CLU5-cF1 (SEQ ID NO: 30) and TiLV-CLU5-cR1 (SEQ ID NO: 31); and
CLU5-mRNA-qF1 (SEQ ID NO: 34) and CLU5-mRNA-qR1 (SEQ ID NO: 35),
with optional probe, CLU5-mRNA-Probe (SEQ ID NO: 36).

In certain aspects, the invention relates to a method for determining the presence or absence of TiLV in a biological sample, the method comprising: a) contacting nucleic acid from a biological sample with at least one primer which is a synthetic nucleic acid of an isolated (or non-isolated) nucleic acid having the sequence of any of SEQ ID NOs: 1-11; an isolated (or non-isolated) nucleic acid complementary to the sequence of any of SEQ ID NOs: 1-11; an isolated (or non-isolated) nucleic acid having at least about 60% sequence identity to any of SEQ ID NOs: 1-11; an isolated (or non-isolated) nucleic acid having at least about 60% sequence identity to a nucleic acid complementary to the sequence of any of SEQ ID NOs: 1-11; an isolated (or non-isolated) nucleic acid which comprises at least 10 consecutive nucleotides of any of SEQ ID NOs: 1-11; an isolated (or non-isolated) nucleic acid which comprises at least 10 consecutive nucleotides of a nucleic acid complementary to the sequence of any of SEQ ID NOs: 1-11; an isolated (or non-isolated) nucleic acid which comprises at least 10 consecutive nucleotides of a sequence having at least about 60% identity to any of SEQ ID NOs: 1-11; or an isolated (or non-isolated) nucleic acid which comprises at least 10 consecutive nucleotides of a sequence having at least about 60% identity to a nucleic acid complementary to the sequence of any of SEQ ID NOs: 1-11, b) subjecting the nucleic acid and the primer to amplification conditions, and, c) determining the presence or absence of amplification product, wherein the presence of amplification product indicates the presence of RNA associated with of TiLV the sample.

The invention also relates to a method for determining the presence or absence of TiLV in a biological sample, the method comprising: a) contacting nucleic acid from a biological sample with a primer pair chosen from the group consisting of: ME1 (SEQ ID NO: 23) and clone 7450/150R (SEQ ID NO: 16); Nested ext-1 (SEQ ID NO: 24) and nested ext-2 (SEQ ID NO: 25); NM-CLU7-SF1 (SEQ ID NO: 28) and NM-CLU7-SRI (SEQ ID NO: 29); TiLV-CLU5-cF1 (SEQ ID NO: 30) and TiLV-CLU5-cR1 (SEQ ID NO: 31); and CLU5-mRNA-qF1 (SEQ ID NO: 34) and CLU5-mRNA-qR1 (SEQ ID NO: 35), b) subjecting the nucleic acid and the primer pair to amplification conditions, and, c) determining the presence or absence of amplification product, wherein the presence of amplification product indicates the presence of RNA associated with of TiLV the sample.

In other aspects, the invention is directed to expression constructs, for example but not limited, to plasmids and vectors which comprise the nucleic acid sequence of any of SEQ ID NOs: 1-11, complementary sequences thereof, fragments and variants thereof. Such expression constructs can be prepared by any suitable method known in the art. Such expression constructs are suitable for viral nucleic acid and/or protein expression and purification.

In certain aspects, the invention is directed to interfering RNA (iRNA) molecules which target nucleic acids from TiLV, for example but not limited to any of SEQ ID NOs: 1-11, and variants thereof, and silence a target gene.

In certain aspects, the invention provides an iRNA comprising a sense strand having at least 15 contiguous nucleotides complementary to the anti-sense strand of a gene comprising a nucleic acid sequence selected from the group of sequences consisting of SEQ ID NOs: 1-11.

In certain aspects, the invention provides an iRNA comprising an anti-sense strand having at least 15 contiguous nucleotides complementary to the sense strand of a gene comprising a nucleic acid sequence selected from the group of sequences consisting of SEQ ID NOs: 1-11.

In certain aspects, the invention relates to iRNA comprising at least 15 contiguous nucleotides of an isolated (or non-isolated) nucleic acid having the sequence of any of SEQ ID NOs: 1-11; an isolated (or non-isolated) nucleic acid complementary to the sequence of any of SEQ ID NOs: 1-11; an isolated (or non-isolated) nucleic acid having at least about 60% sequence identity to any of SEQ ID NOs: 1-11; or an isolated (or non-isolated) nucleic acid having at least about 60% sequence identity to a nucleic acid complementary to the sequence of any of SEQ ID NOs: 1-11.

An "iRNA agent" (abbreviation for "interfering RNA agent") as used herein, is an RNA agent, which can downregulate the expression of a target gene, e.g. a TiLV gene. An iRNA agent may act by one or more of a number of mechanisms, including post-transcriptional cleavage of a target mRNA sometimes referred to in the art as RNAi, or pre-transcriptional or pre-translational mechanisms. An iRNA agent can be a double stranded (ds) iRNA agent.

A "ds iRNA agent" (abbreviation for "double stranded iRNA agent"), as used herein, is an iRNA agent which includes more than one, and in certain embodiments two, strands in which interchain hybridization can form a region of duplex structure. A "strand" herein refers to a contiguous sequence of nucleotides (including non-naturally occurring or modified nucleotides). The two or more strands may be, or each form a part of, separate molecules, or they may be covalently interconnected, e.g. by a linker, e.g. a polyethyleneglycol linker, to form but one molecule. At least one strand can include a region which is sufficiently complementary to a target RNA. Such strand is termed the "antisense strand". A second strand comprised in the dsRNA agent which comprises a region complementary to the antisense strand is termed the "sense strand". However, a ds iRNA agent can also be formed from a single RNA molecule which is, at least partly; self-complementary, forming, e.g., a hairpin or panhandle structure, including a duplex region. In such case, the term "strand" refers to one of the regions of the RNA molecule that is complementary to another region of the same RNA molecule.

iRNA agents as described herein, including ds iRNA agents and siRNA agents, can mediate silencing of a gene, e.g., by RNA degradation. For convenience, such RNA is also referred to herein as the RNA to be silenced. Such a gene is also referred to as a target gene. In certain embodiments, the RNA to be silenced is a gene product of a TiLV gene.

As used herein, the phrase "mediates RNAi" refers to the ability of an agent to silence, in a sequence specific manner, a target gene. "Silencing a target gene" means the process whereby a cell containing and/or secreting a certain product of the target gene when not in contact with the agent, will contain and/or secrete at least 10%, 20%, 30%, 40%, 50%, 60%, 70%, 80%, or 90% less of such gene product when contacted with the agent, as compared to a similar cell which has not been contacted with the agent. Such product of the target gene can, for example, be a messenger RNA (mRNA), a protein, or a regulatory element.

In the anti-viral uses of the present invention, silencing of a target gene can result in a reduction in "viral titer" in the cell or in the animal, wherein "reduction in viral titer" refers to a decrease in the number of viable virus produced by a cell or found in an organism undergoing the silencing of a viral target gene. Reduction in the cellular amount of virus produced can lead to a decrease in the amount of measurable virus produced in the tissues of an animal undergoing treatment and a reduction in the severity of the symptoms of the viral infection. iRNA agents of the present invention are also referred to as "antiviral iRNA agents".

In other aspects, the invention provides methods for reducing viral titer in an animal, by administering to an animal, at least one iRNA which inhibits the expression of a TiLV gene.

In certain aspects, the invention provides a methods for reducing the levels of a viral protein, viral mRNA, or viral titer in a cell in an animal comprising: administering an iRNA agent to an animal, wherein the iRNA agent comprises a sense strand having at least 15 contiguous nucleotides complementary to a gene or genome segment from TiLV comprising a nucleic acid sequence selected from the group of sequences consisting of SEQ ID NOs: 1-11 and an antisense strand having at least 15 contiguous nucleotides complementary to the sense strand. In one embodiment, the method further comprises co-administering a second iRNA agent to the animal, wherein the second iRNA agent comprises a sense strand having at least 15 or more contiguous nucleotides complementary to a second gene or genome segment from the TiLV comprising a nucleic acid sequence selected from the group of sequences consisting of SEQ ID NOs: 1-11 and an antisense strand having at least 15 contiguous nucleotides complementary to the sense strand.

In certain aspects, the invention provides a method for reducing the levels of a viral protein from at least one gene of TiLV in a cell in an animal comprising: administering an iRNA agent to an animal, wherein the iRNA agent comprises a sense strand having at least 15 contiguous nucleotides complementary to a gene from TiLV comprising a nucleic acid sequence selected from the group of sequences consisting of SEQ ID NOs: 1-11 and an antisense strand having at least 15 contiguous nucleotides complementary to the sense strand.

Isolated Polypeptides and Uses Thereof

The invention is also directed to isolated polypeptides and variants and derivatives thereof. These polypeptides may be useful for multiple applications, including, but not limited to, generation of antibodies and generation of immunogenic compositions. For example, the invention is directed to an isolated polypeptide of SEQ ID NO: 12. For example, the invention is also directed to any isolated polypeptide encoded by the nucleic sequence acid of any of SEQ ID NO: 1-11, fragments and variants thereof. A peptide of at least 8 amino acid residues in length can be recognized by an antibody MacKenzie et al. (1984) *Biochemistry* 23: 6544-6549). In certain embodiments, the invention is directed to fragments of the polypeptides described herein, which can, for example, be used to generate antibodies.

Thus, in certain aspects, the invention relates to an isolated polypeptide having at least about 80% sequence identity to the polypeptide of SEQ ID NO: 12. In certain aspects, the invention relates to an isolated polypeptide comprising at least 8 consecutive amino acids of the polypeptide of SEQ ID NO: 12. In certain aspects, the invention relates to an isolated polypeptide comprising at least 8 amino acids having at least about 80% identity to the sequence of the polypeptide of SEQ ID NO: 12.

In one aspect, the invention is directed to polypeptide variants of an isolated polypeptide of SEQ ID NO: 12. Variants the isolated polypeptides of SEQ ID NO: 12 include, but are not limited to, polypeptide sequences having at least from about 50% to about 55% identity to that of an isolated polypeptide of SEQ ID NO: 12. Variants of an isolated polypeptide of SEQ ID NO: 12 include, but are not limited to, polypeptide sequences having at least from about 55.1% to about 60% identity to that of an isolated polypeptide of SEQ ID NO: 12. Variants of an isolated polypeptide of SEQ ID NO: 12 include, but are not limited to, polypeptide sequences having at least from about 60.1% to about 65% identity to that of an isolated polypeptide of SEQ ID NO: 12. Variants of an isolated polypeptide of SEQ ID NO: 12 include, but are not limited to, polypeptide sequences having at least from about 65.1% to about 70% identity to that of an isolated polypeptide of SEQ ID NO: 12. Variants of an isolated polypeptide of SEQ ID NO: 12 include, but are not limited to, polypeptide having at least from about 70.1% to about 75% identity to that of an isolated polypeptide of SEQ ID NO: 12. Variants of an isolated polypeptide of SEQ ID NO: 12 include, but are not limited to, polypeptide sequences having at least from about 75.1% to about 80% identity to that of an isolated polypeptide of SEQ ID NO: 12. Variants of an isolated polypeptide of SEQ ID NO: 12 include, but are not limited to, polypeptide sequences having at least from about 80.1% to about 85% identity to that of an isolated polypeptide of SEQ ID NO: 12. Variants of an isolated polypeptide of SEQ ID NO: 12 include, but are not limited to, polypeptide sequences having at least from about 85.1% to about 90% identity to that of an isolated polypeptide of SEQ ID NO: 12. Variants of an isolated polypeptide of SEQ ID NO: 12 include, but are not limited to, polypeptide sequences having at least from about 90.1% to about 95% identity to that of an isolated polypeptide of SEQ ID NO: 12. Variants of an isolated polypeptide of SEQ ID NO: 12 include, but are not limited to, polypeptide sequences having at least from about 95.1%, about 95.5%, about 96%, about 96.5%, about 97%, about 97.5%, about 98%, about 98.5%, about 99%, about 99.5% or about 99.9% identity to that of an isolated polypeptide of SEQ ID NO: 12.

In one aspect, the invention is directed to polypeptide variants of any isolated polypeptide encoded by the nucleic acid sequence of any of SEQ ID NOs: 1-11. Variants of any one of the isolated polypeptides encoded by the nucleic acid sequence acid of any of SEQ ID NOs: 1-11 include, but are not limited to, polypeptide sequences having at least from about 50% to about 55% identity to that of any isolated polypeptide encoded by the nucleic acid sequence of any of SEQ ID NOs: 1-11. Variants of any isolated polypeptide encoded by the nucleic acid sequence of any of SEQ ID NOs: 1-11 include, but are not limited to, polypeptide sequences having at least from about 55.1% to about 60% identity to that of any isolated polypeptide encoded by the nucleic acid sequence of any of SEQ ID NOs: 1-11. Variants of any isolated polypeptide encoded by the nucleic acid sequence of any of SEQ ID NOs: 1-11 include, but are not limited to, polypeptide sequences having at least from about 60.1% to about 65% identity to that of any isolated polypeptide encoded by the nucleic acid sequence of any of SEQ ID NOs: 1-11. Variants of any isolated polypeptide encoded by the nucleic acid sequence of any of SEQ ID NOs: 1-11 include, but are not limited to, polypeptide sequences having at least from about 65.1% to about 70% identity to that of any isolated polypeptide encoded by the nucleic acid sequence of any of SEQ ID NOs: 1-11. Variants of any isolated polypeptide encoded by the nucleic acid sequence of any of SEQ ID NOs: 1-11 include, but are not limited to, polypeptide having at least from about 70.1% to about 75% identity to that of any isolated polypeptide encoded by the nucleic acid sequence of any of SEQ ID NOs: 1-11. Variants of any isolated polypeptide encoded by the nucleic acid sequence of any of SEQ ID NOs: 1-11 include, but are not limited to, polypeptide sequences having at least from about 75.1% to about 80% identity to that of any isolated polypeptide encoded by the nucleic acid sequence of any of SEQ ID NOs: 1-11. Variants of any isolated polypeptide encoded by the nucleic acid sequence of any of SEQ ID NOs: 1-11 include, but are not limited to, polypeptide sequences having at least from about 80.1% to about 85% identity to that of any isolated polypeptide encoded by the nucleic acid sequence of any of SEQ ID NOs: 1-11. Variants of any isolated polypeptide encoded by the nucleic acid sequence of any of SEQ ID NOs: 1-11 include, but are not limited to, polypeptide sequences having at least from about 85.1% to about 90% identity to that of any isolated polypeptide encoded by the nucleic acid sequence of any of SEQ ID NOs: 1-11. Variants of any isolated polypeptide encoded by the nucleic acid sequence of any of SEQ ID NOs: 1-11 include, but are not limited to, polypeptide sequences having at least from about 90.1% to about 95% identity to that of any isolated polypeptide encoded by the nucleic acid sequence of any of SEQ ID NOs: 1-11. Variants of any isolated polypeptide encoded by the nucleic acid sequence of any of SEQ ID NOs: 1-11 include, but are not limited to, polypeptide sequences having at least from about 95.1%, about 95.5%, about 96%, about 96.5%, about 97%, about 97.5%, about 98%, about 98.5%, about 99%, about 99.5% or about 99.9% identity to that of any of SEQ ID NOs: 1-11.

The invention is also directed to a polypeptide encoded by a nucleic acid that is complementary to a nucleic acid sequence of any of SEQ ID NOs: 1-11 or a fragment or variant thereof.

The invention is directed to a polypeptide comprising from about 10 to about 50 consecutive amino acids of SEQ ID NO: 12 or variants thereof. The invention is directed to a polypeptide comprising from about 10 to about 100 consecutive amino acids of SEQ ID NO: 12 or variants thereof. The invention is directed to a polypeptide comprising from about 10 to about 150 consecutive amino acids of SEQ ID NO: 12 or variants thereof. The invention is directed to a polypeptide comprising from about 10 to about 200 consecutive amino acids of SEQ ID NO: 12 or variants thereof. The invention is directed to a polypeptide comprising from about 10 to about 250 consecutive amino acids of SEQ ID NO: 12 or variants thereof. The invention is directed to a polypeptide comprising from about 10 to about 300 consecutive amino acids of SEQ ID NO: 12 or variants thereof. The invention is directed to a polypeptide comprising from about 10 to about 350 consecutive amino acids of SEQ ID NO: 12 or variants thereof. The invention is directed to a polypeptide comprising from about 10 to about 400 consecutive amino acids of SEQ ID NO: 12 or variants thereof. The invention is directed to a polypeptide comprising from about 10 to about 420 consecutive amino acids of SEQ ID NO: 12 or variants thereof. In certain embodiments, the invention is directed to isolated and purified peptides.

In certain embodiments, the polypeptides of the present invention can be suitable for use as antigens to detect antibodies against SEQ ID NO: 12, and variants thereof. In other embodiments, the polypeptides of the present invention which comprise antigenic determinants can be used in various immunoassays to identify animals exposed to and/or samples which comprise SEQ ID NO: 12, and variants thereof.

The invention is directed to a polypeptide comprising from about 10 to about 50 consecutive amino acids from any isolated polypeptide encoded by the nucleic acid sequence of any of SEQ ID NOs: 1-11 or complementary sequences or variants thereof. The invention is directed to a polypeptide comprising from about 10 to about 100 consecutive amino acids from any isolated polypeptide encoded by the nucleic acid sequence of any of SEQ ID NOs: 1-11 or complementary sequences or variants thereof. The invention is directed to a polypeptide comprising from about 10 to about 150 consecutive amino acids from any isolated polypeptide encoded by the nucleic acid sequence of any of SEQ ID NOs: 1-11 or complementary sequences or variants thereof. The invention is directed to a polypeptide comprising from about 10 to about 200 consecutive amino acids from any isolated polypeptide encoded by the nucleic acid sequence of any of SEQ ID NOs: 1-11 or complementary sequences or variants thereof. The invention is directed to a polypeptide comprising from about 10 to about 250 consecutive amino acids from any isolated polypeptide encoded by the nucleic acid sequence of any of SEQ ID NOs: 1-11 or complementary sequences or variants thereof. The invention is directed to a polypeptide comprising from about 10 to about 300 consecutive amino acids from any isolated polypeptide encoded by the nucleic acid sequence of any of SEQ ID NOs: 1-11 or complementary sequences or variants thereof. The invention is directed to a polypeptide comprising from about 10 to about 350 consecutive amino acids from any isolated polypeptide encoded by the nucleic acid sequence of any of SEQ ID NOs: 1-11 or complementary sequences or variants thereof. The invention is directed to a polypeptide comprising from about 10 to about 400 consecutive amino acids from any isolated polypeptide encoded by the nucleic acid sequence of any of SEQ ID NOs: 1-11 or complementary sequences or variants thereof. The invention is directed to a polypeptide comprising from about 10 to about 450 consecutive amino acids from any isolated polypeptide encoded by the nucleic acid sequence of any of SEQ ID NOs: 1-11 or complementary sequences or variants thereof. The invention is directed to a polypeptide comprising from about 10 to about 460 consecutive amino acids from any isolated polypeptide encoded by the nucleic acid sequence of any of SEQ ID NOs: 1-11 or complementary sequences or variants thereof. The invention is directed to a polypeptide comprising from about 10 to about 470 consecutive amino acids from any isolated polypeptide encoded by the nucleic acid sequence acid of any of SEQ ID NOs: 1-11 or complementary sequences or variants thereof. The invention is directed to a polypeptide comprising from about 10 to about 480 consecutive amino acids from any isolated polypeptide encoded by the nucleic acid sequence acid of any of SEQ ID NOs: 1-11 or complementary sequences or variants thereof. The invention is directed to a polypeptide comprising from about 10 to about 490 consecutive amino acids from any isolated polypeptide encoded by the nucleic acid sequence acid of any of SEQ ID NOs: 1-11 or complementary sequences or variants thereof. The invention is further directed a polypeptide comprising from about 10 to about 550 consecutive amino acids or more from any isolated polypeptide encoded by the nucleic acid sequence acid of any of SEQ ID NOs: 1-11 or complementary sequences or variants thereof. In certain embodiments, the invention is directed to isolated and purified peptides.

In certain embodiments, the polypeptides of the present invention can be suitable for use as antigens to detect antibodies against TiLV represented by any of SEQ ID NOs: 1-11, and variants thereof. In other embodiments, the polypeptides of the present invention which comprise antigenic determinants can be used in various immunoassays to identify animals exposed to and/or samples which comprise TiLV represented by any of SEQ ID NOs: 1-11, and variants thereof.

Antibodies, Methods of Making and Methods of Using

In another aspect, the invention is directed to an antibody which specifically binds to amino acids from the polypeptide of an isolated polypeptide of SEQ ID NO: 12, fragments and variants thereof, as described herein. In one embodiment the antibody is purified. The antibodies can be polyclonal or monoclonal. The antibodies can also be chimeric (i.e., a combination of sequences from more than one species, for example, a chimeric mouse-human immunoglobulin), humanized or fully-human. Species specific antibodies avoid certain of the problems associated with antibodies that possess variable and/or constant regions from other species. The presence of such protein sequences from other species can lead to the rapid clearance of the antibodies or can lead to the generation of an immune response against the antibody by an antibody.

In another aspect, the invention is directed to an antibody which specifically binds to amino acids from the polypeptide of any isolated polypeptide encoded by the nucleic sequence acid of any of SEQ ID NOs: 1-11, fragments and variants thereof, as described herein. In one embodiment the antibody is purified. The antibodies can be polyclonal or monoclonal. The antibodies can also be chimeric (i.e., a combination of sequences from more than one species, for example, a chimeric mouse-human immunoglobulin), humanized or fully-human Species specific antibodies avoid certain of the problems associated with antibodies that possess variable and/or constant regions from other species. The presence of such protein sequences from other species can lead to the rapid clearance of the antibodies or can lead to the generation of an immune response against the antibody by an antibody.

An antibody described in this application can include or be derived from any mammal, such as but not limited to, a bird, a dog, a human, a mouse, a rabbit, a rat, a rodent, a primate, or any combination thereof and includes isolated avian, human, primate, rodent, mammalian, chimeric, humanized and/or CDR-grafted or CDR-adapted antibodies, immunoglobulins, cleavage products and other portions and variants thereof.

Any method known in the art for producing antibodies can be used to generate the antibodies described herein. Exemplary methods include animal inoculation, phage display, transgenic mouse technology and hybridoma technology.

The antibodies of the present invention can be used to modulate the activity of any polypeptide encoded by the nucleic sequence acid of any of SEQ ID NOs: 1-11, variants or fragments thereof. In certain aspects, the invention is directed to a method for treating an animal, the method comprising administering to the animal an antibody which specifically binds to amino acids from the polypeptide of any polypeptide encoded by the nucleic sequence acid of any of SEQ ID NOs: 1-11, fragments and variants thereof, as described herein.

In certain embodiments, antibody binding to the polypeptide of any polypeptide encoded by the nucleic sequence acid of any of SEQ ID NOs: 1-11, fragments and variants thereof, as described herein, may interfere or inhibit the function of the polypeptide, thus providing a method to inhibit virus propagation and spreading. In other embodiments, the antibody binds to the polypeptide of any polypeptide encoded by the nucleic sequence acid of any of SEQ ID NOs: 1-11, fragments and variants thereof, as described herein, and does not interfere or inhibit the function of the polypeptide.

In other embodiments, the antibodies of the invention can be used to purify a polypeptide of SEQ ID NO: 12, variants or fragments thereof as described herein. In other embodiments, the antibodies of the invention can be used to identify expression and localization of the polypeptide of SEQ ID NO: 12, variants, fragments or domains thereof. Analysis of expression and localization of the polypeptide of SEQ ID NO: 12 can be useful in determining potential role of the polypeptide of SEQ ID NO: 12.

In other embodiments, the antibodies of the invention can be used to purify polypeptides of any polypeptide encoded by the nucleic acid sequence of any of SEQ ID NOs: 1-11, variants or fragments thereof as described herein. In other embodiments, the antibodies of the invention can be used to identify expression and localization of the polypeptide of any polypeptide encoded by the nucleic acid sequence of any of SEQ ID NOs: 1-11, variants, fragments or domains thereof. Analysis of expression and localization of the polypeptide of any polypeptide encoded by the nucleic acid sequence of any of SEQ ID NOs: 1-11 can be useful in determining potential role of the polypeptide of any polypeptide encoded by the nucleic acid sequence of any of SEQ ID NOs: 1-11 and fragments and variants thereof.

In other embodiments, the antibodies of the present invention can be used in various immunoassays to identify animals exposed to and/or samples which comprise antigens from TiLV represented by SEQ ID NO: 12, and fragments and variants thereof, as described herein.

In other embodiments, the antibodies of the present invention can be used in various immunoassays to identify animals exposed to and/or samples which comprise antigens from TiLV represented by any of SEQ ID NOs: 1-11, and fragments and variants thereof, as described herein.

Any suitable immunoassay which can lead to formation of antigen-antibody complex can also be used. Variations and different formats of immunoassays, for example but not limited to ELISA, lateral flow assays for detection of analytes in samples, immunoprecipitation, are known in the art. In various embodiments, the antigen and/or the antibody can be labeled by any suitable label or method known in the art. For example enzymatic immunoassays may use solid supports, or immunoprecipitation Immunoassays which amplify the signal from the antigen-antibody immune complex can also be used with the methods described herein.

In certain aspects the invention provides methods for assaying a sample to determine the presence or absence of a TiLV comprising SEQ ID NO: 12, and fragments and variants thereof, as described herein. In certain embodiments, methods for assaying a sample, include, but are not limited to, methods which can detect the presence of nucleic acids, methods which can detect the presence of antigens, methods which can detect the presence of antibodies against antigens from a polypeptide of SEQ ID NO: 12, or a polypeptide of SEQ ID NO: 12, fragments and variants thereof, as described herein.

In certain aspects the invention provides methods for assaying a sample to determine the presence or absence of a TiLV comprising any of SEQ ID NOs: 1-11, and fragments and variants thereof, as described herein. In certain embodiments, methods for assaying a sample, include, but are not limited to, methods which can detect the presence of nucleic acids, methods which can detect the presence of antigens, methods which can detect the presence of antibodies against antigens from polypeptides encoded by any of SEQ ID NOs: 1-11, or any polypeptide encoded by the nucleic sequence acid of any of SEQ ID NOs: 1-11, fragments and variants thereof, as described herein.

Kits

Also provided for are kits for practicing one or more of the above-described methods.

The subject reagents and kits thereof may vary greatly. Reagents of interest include reagents specifically designed for use in determining if an animal has TiLV.

One type of regent that is specifically tailored for the detection of the TiLV is at least one oligonucleotide primer specific SEQ ID NOs: 1-11 to amplify nucleic acid obtained from a biological sample, and, optionally, at least one primer suitable to enable sequencing of the amplified nucleic acid and determination of the presence of the mutation.

Examples of primers that can be included as reagents are:

ME1 (SEQ ID NO: 23) and clone 7450/150R (SEQ ID NO: 16);

Nested ext-1 (SEQ ID NO: 24) and nested ext-2 (SEQ ID NO: 25);

NM-CLU7-SF1 (SEQ ID NO: 28) and NM-CLU7-SRI (SEQ ID NO: 29);

TiLV-CLU5-cF1 (SEQ ID NO: 30) and TiLV-CLU5-cR1 (SEQ ID NO: 31); and

CLU5-mRNA-qF1 (SEQ ID NO: 34) and CLU5-mRNA-qR1 (SEQ ID NO: 35), with optional probe, CLU5-mRNA-Probe (SEQ ID NO: 36).

A further type of reagent is one or more nucleic acid probes comprising or complementary SEQ ID NOs: 1-11. In one embodiment, one or more probes are in an array formation. A variety of different array formats are known in the art with a wide variety of different probe structures, substrate compositions, and attachment technologies. In some embodiments, the arrays include at least 2 nucleic acid probes, in a more preferred embodiment, at least 5 nucleic acid probes, in a more preferred embodiment, at least 10 nucleic acid probes, in a more preferred embodiment, at least 15 nucleic acid probes, in a more preferred embodiment, at least 25 nucleic acid probes, and in a most preferred embodiment, at least 50 nucleic acid probes, said nucleic acid probes comprising or complementary SEQ ID NOs: 1-11.

A further type of reagent is one or more antibodies as described herein that specifically binds to amino acids from the polypeptide of an isolated polypeptide of SEQ ID NO: 12, fragments and variants thereof, or amino acids from the polypeptide of any isolated polypeptide encoded by the nucleic sequence acid of any of SEQ ID NOs: 1-11, fragments and variants thereof.

The kit of the invention may include the above-described primers, probes, arrays, and antibodies as well as additional reagents employed in the various methods, such as: labeling reagents; enzymes such as reverse transcriptase, DNA and RNA polymerases, and the like; various buffers, such as hybridization and washing buffers; signal generation and detection reagents; and reagents for isolation of nucleic acid from a sample. In addition, the kit may include instructions for practicing the methods of the present invention.

The invention also covers systems for practicing one or more of the above-described methods. The subject systems may vary greatly but typically include at least one element to detect TiLV, i.e., one or more reagents described above for detection of TiLV, including primers, probes, arrays, antibodies, and additional reagents for practicing the methods of the invention.

Immunogenic Compositions, Methods of Making and Methods of Using

As used herein, the term immunogenic composition refers to a composition capable of inducing an immunogenic response in an animal or a cell. As used herein, reference to an immunogenic composition can include a vaccine.

In certain aspects, the present invention provides immunogenic compositions capable of inducing an immune response against TiLV including TiLV of the invention comprising a nucleic acid of any of SEQ ID NOs: 1-11 or fragments or variants thereof, or comprising a cDNA sequence complementary to the sense or an anti-sense strand of any of SEQ ID NOs: 1-11 or fragments or variants thereof, or comprising a polypeptide encoded by any of SEQ ID NOs: 1-11, or a cDNA sequence complementary to the sense or an anti-sense strand of any of SEQ ID NOs: 1-11, or comprising a polypeptide comprising SEQ ID NO: 12 or fragments or variants thereof or comprising a killed or attenuated TiLV.

In certain aspects, the invention relates to an immunogenic composition comprising any TiLV nucleic acid or polypeptide described herein, including variants and fragments.

In one embodiment, the immunogenic compositions are capable of ameliorating the symptoms of a TiLV infection and/or of reducing the duration of a TiLV associated disease. In another embodiment, the immunogenic compositions are capable of inducing protective immunity against TiLV associated disease. The immunogenic compositions of the invention can be effective against the TiLV viruses disclosed herein, and may also be cross-reactive with, and effective against, multiple different clades and strains of TiLV, and against other orthomyxoviruses.

In another embodiment, the invention provides a method of inducing an immune response in an animal, the method comprising administering a TiLV nucleic acid, a TiLV polypeptide or a TiLV immunogenic composition to the animal Methods for administering polypeptides to animals and methods of generating immune responses in animals by administering immunogenic peptides in immunogenically effective amounts are known in the art.

The types of immunogenic composition encompassed by the invention include, but are not limited to, attenuated live viral immunogenic compositions, inactivated (killed) viral immunogenic compositions, and subunit immunogenic compositions.

The TiLV viruses of the invention may be attenuated by removal or disruption of those viral sequences whose products cause or contribute to the disease and symptoms associated with TiLV infection, and leaving intact those sequences required for viral replication. In this way an attenuated TiLV can be produced that replicates in animals, and induces an immune response in animals, but which does not induce the deleterious disease and symptoms usually associated with TiLV infection. One of skill in the art can determine which TiLV sequences can or should be removed or disrupted, and which sequences should be left intact, in order to generate an attenuated TiLV suitable for use as an immunogenic composition.

The novel TiLV of the invention may be also be inactivated, such as by chemical treatment, to "kill" the viruses such that they are no longer capable of replicating or causing disease in animals, but still induce an immune response in an animal. There are many suitable viral inactivation methods known in the art and one of skill in the art can readily select a suitable method and produce an inactivated "killed" TiLV suitable for use as an immunogenic composition.

The immunogenic compositions of the invention may comprise subunit immunogenic compositions. Subunit immunogenic compositions include nucleic acid immunogenic compositions such as DNA immunogenic compositions, which contain nucleic acids that encode one or more viral proteins or subunits, or portions of those proteins or subunits. When using such immunogenic compositions, the nucleic acid is administered to the animal, and the immunogenic proteins or peptides encoded by the nucleic acid are expressed in the animal, such that an immune response against the proteins or peptides is generated in the animal. Subunit immunogenic compositions may also be proteinaceous immunogenic compositions, which contain the viral proteins or subunits themselves, or portions of those proteins or subunits.

To make the nucleic acid and DNA immunogenic compositions of the invention TiLV sequences disclosed herein may be incorporated into a plasmid or expression vector containing the nucleic acid that encodes the viral protein or peptide. Any suitable plasmid or expression vector capable of driving expression of the protein or peptide in the animal may be used. Such plasmids and expression vectors should include a suitable promoter for directing transcription of the nucleic acid. The nucleic acid sequence(s) that encodes TiLV protein or peptide may also be incorporated into a suitable recombinant virus for administration to the animal Examples of suitable viruses include, but are not limited to, vaccinia viruses, retroviruses, adenoviruses and adeno-associated viruses. One of skill in the art could readily select a suitable plasmid, expression vector, or recombinant virus for delivery of TiLV nucleic acid sequences of the invention.

To produce the proteinaceous immunogenic compositions of the invention, TiLV nucleic acid sequences of the invention are delivered to cultured cells, for example by transfecting cultured cells with plasmids or expression vectors containing TiLV nucleic acid sequences, or by infecting cultured cells with recombinant viruses containing TiLV nucleic acid sequences. TiLV proteins or peptides may then be expressed in the cultured cells and purified. The purified proteins can then be incorporated into compositions suitable for administration to animals. Methods and techniques for expression and purification of recombinant proteins are well known in the art, and any such suitable methods may be used.

Subunit immunogenic compositions of the present invention may encode or contain any of TiLV proteins or peptides described herein, or any portions, fragments, derivatives or mutants thereof, that are immunogenic in an animal. One of skill in the art can readily test the immunogenicity of TiLV proteins and peptides described herein, and can select suitable proteins or peptides to use in subunit immunogenic compositions.

Production of the TiLV viruses and immunogenic compositions can also be performed using a recombinant expression system that expresses TiLV, a TiLV protein, a fragment of a TiLV protein or a variant of a TiLV viral protein. The expression system can comprise any suitable plasmid or a linear expression construct known in the art.

The TiLV viruses and immunogenic compositions described herein can be produced in cells. Production of the TiLV viruses and immunogenic compositions described herein may also be accomplished on any useful media and permissive cell or tissues, which may be derived from fish or other animal cell lines. As used herein, a cell or a tissue can include, but is not limited to individual cells, tissues, organs, insect cells, fish cells, mammalian cells, hybridoma cells, primary cells, continuous cell lines, and/or genetically engineered cells, such as recombinant cells expressing a virus. For example, production of the TiLV viruses and immunogenic compositions can be in any cell type, including but not limited to tilapia cells. Cell lines suitable for producing the TiLV viruses and immunogenic compositions described herein The cell culture system for producing the TiLV viruses and immunogenic compositions described herein can be a traditional adherent monolayer culture. Alternatively, suspension and microcarrier cell culture systems can also be utilized.

The immunogenic compositions described herein can comprise an inactivated or killed TiLV vaccine. Inactivated immunogenic composition can be made by methods well known in the art. For example, once TiLV is propagated to high titers, TiLV antigenic mass could be obtained by methods well known in the art. For example, the TiLV viral antigenic mass may be obtained by dilution, concentration, or extraction. All of these methods have been employed to obtain appropriate TiLV antigenic mass to produce immunogenic compositions. TiLV may be inactivated by treatment with formalin (e.g. 0.1-10%), betapropriolactone (BPL) (e.g. 0.01-10%), or with binary ethyleneimine (BEI) (e.g. 1-10 mM), or using other methods known to those skilled in the art.

In addition to killed TiLV production, various means of attenuation are also possible and are well known and described in the art. Attenuation leading to modified live immunogenic compositions can also be used in conjunction with the compositions and methods described herein. Methods of attenuation suitable for use with the viruses described herein include continuous passaging in cell culture, continuous passaging in animals, various methods for generating genetic modifications and ultraviolet or chemical mutagenesis.

Attenuation of TiLV may be achieved through cold-adaptation of an TiLV strain. Cold-adapted TiLV virus strains may be produced by methods which includes passaging a wild-type TiLV virus, followed by selection for TiLV that grows at a reduced temperature. Cold-adapted TiLV can be produced, for example, by sequentially passaging a wild-type TiLV in embryonated cells or chicken eggs at progressively lower temperatures, thereby selecting for certain members of TiLV mixture which stably replicate at the reduced temperature. A cold-adapted TiLV strain may exhibit a temperature sensitive phenotype. A temperature sensitive cold-adapted TiLV replicates at reduced temperatures, but no longer replicates at certain higher growth temperatures at which the wild-type TiLV will replicate. A temperature at which a temperature sensitive TiLV will grow is referred to herein as a "permissive" temperature for that temperature sensitive TiLV, and a higher temperature at which the temperature sensitive TiLV will not grow, but at which a corresponding wild-type TiLV will grow, is referred to herein as a "non-permissive" temperature for that temperature sensitive TiLV. A cold-adapted TiLV may also be produced through recombinant means. In this approach, one or more specific mutations, associated with identified cold-adaptation, attenuation, temperature sensitivity, or dominant interference phenotypes, can be identified and are introduced back into a wild-type TiLV strain using a reverse genetics approach. Reverse genetics entails can be performed using RNA polymerase complexes isolated from TiLV-infected cells to transcribe artificial TiLV genome segments containing the mutation(s), incorporating the synthesized RNA segment(s) into virus particles using a helper virus, and then selecting for viruses containing the desired changes.

Attenuation of a TiLV may be achieved by serial passaging of a wild-type TiLV strain in cell culture. TiLV strain can be passaged in a variety of cell systems until its ability to produce disease is lost whilst its immunogenic character is fully retained. Once inoculated into the host, TiLV may be capable of multiplication to some extent. For example, attenuated TiLV compositions can be prepared from cell line that has been attenuated by serial passage including serial passage at sub-optimal temperatures to a state where it is no longer capable of causing disease, but still capable of eliciting a protective immune response.

Suitable attenuated TiLV strains may also be obtained by serial passaging to obtain an over-attenuated strain. The "over-attenuation" means that the number of passages for attenuation has been substantially greater than what is normally necessary for the removal of pathogenicity. The attenuated TiLV retains its antigenicity after these numerous passages so that its immunogenic ability is not impaired. Such strains produce practically no symptoms or side effects when administered, and thus are safe and efficacious vaccines.

Methods of purification of inactivated virus are known in the art and may include one or more of, for instance gradient centrifugation, ultracentrifugation, continuous-flow ultracentrifugation and chromatography, such as ion exchange chromatography, size exclusion chromatography, and liquid affinity chromatography. Additional methods of purification include ultrafiltration and dialfiltration.

Other examples of purification methods suitable for use in the invention include polyethylene glycol or ammonium sulfate precipitation (see Trepanier et al. (1981) *Journal of Virological Methods* 3:201-711; Hagen et al. (1996) *Biotechnology Progress* 12:406-412; and Carlsson et al. (1994) *Journal of Virological Methods* 47:27-36) as well as ultrafiltration and microfiltration (see Pay et al. (1985) *Developments in Biological Standardization* 60:171-174; Tsurumi et al. (1990) *Polymer Journal* 22:1085-1100; and Makino et al. (1994) *Archives of Virology* 139:87-96).

Viruses can be purified using chromatography, such as ion exchange, chromatography. Chromatic purification allows for the production of large volumes of virus containing suspension. The viral product of interest can interact with the chromatic medium by a simple adsorption/desorption mechanism, and large volumes of sample can be processed in a single load. Contaminants which do not have affinity for the adsorbent pass through the column. The virus material can then be eluted in concentrated form.

Anion exchange resins that may be used include but are not limited to DEAE, and EMD TMAE. Cation exchange resins may comprise a sulfonic acid-modified surface. Viruses can be purified using ion exchange chromatography comprising a strong anion exchange resin (e.g. EMD TMAE) for the first step and EMD-503 (cation exchange resin) for the second step. A metal-binding affinity chromatography step can optionally be included for further purification. (See, e.g., WO 97/06243).

A resin such as Fractogel EMD can also be used This synthetic methacrylate based resin has long, linear polymer chains covalently attached and allows for a large amount of sterically accessible ligands for the binding of biomolecules without any steric hindrance.

Column-based liquid affinity chromatography is another purification method that can be used invention. One example of a resin for use in purification method is Matrex Cellufine Sulfate (MCS). MCS consists of a rigid spherical (approximately 45-105.mu.m diameter) cellulose matrix of 3,000 Dalton exclusion limit (its pore structure excludes macromolecules), with a low concentration of sulfate ester functionality on the 6-position of cellulose. As the functional ligand (sulfate ester) is relatively highly dispersed, it presents insufficient cationic charge density to allow for most soluble proteins to adsorb onto the bead surface. Therefore the bulk of the protein found in typical virus pools (cell culture supernatants, e.g. pyrogens and most contaminating proteins, as well as nucleic acids and endotoxins) are washed from the column and a degree of purification of the bound virus is achieved.

Inactivated viruses may be further purified by gradient centrifugation, or density gradient centrifugation. For commercial scale operation a continuous flow sucrose gradient centrifugation would be an option. This method is widely used to purify antiviral immunogenic compositions and is known to one skilled in the art.

Additional purification methods which may be used to purify viruses of the invention include the use of a nucleic acid degrading agent, a nucleic acid degrading enzyme, such as a nuclease having DNase and RNase activity, or an endonuclease, such as from *Serratia marcescens*, membrane adsorbers with anionic functional groups or additional chromatographic steps with anionic functional groups (e.g. DEAE or TMAE). An ultrafiltration/dialfiltration and final sterile filtration step could also be added to the purification method.

The purified viral preparation of the invention is substantially free of contaminating proteins derived from the cells or cell culture and can comprises less than about 1000, 500, 250, 150, 100, or 50 pg cellular nucleic acid/.mu.g virus antigen, and less than about 1000, 500, 250, 150, 100, or 50 pg cellular nucleic acid/dose. The purified viral preparation can also comprises less than about 20 pg or less than about 10 pg. Methods of measuring host cell nucleic acid levels in a viral sample are known in the art. Standardized methods approved or recommended by regulatory authorities such as the WHO or the FDA can be used.

The immunogenic compositions of the invention comprise at least one TiLV-derived immunogenic component, such as those described herein. The compositions may also comprise one or more additives including, but not limited to, one or more pharmaceutically acceptable carriers, buffers, stabilizers, diluents, preservatives, solubilizers, liposomes or immunomodulatory agents. Suitable immunomodulatory agents include, but are not limited to, adjuvants, cytokines, polynucleotide encoding cytokines, and agents that facilitate cellular uptake of TiLV-derived immunogenic component.

Immunogenic compositions for use in accordance with the present invention thus may be formulated in a conventional manner using one or more physiologically acceptable carriers comprising excipients and auxiliaries which facilitate processing of the active compounds into preparations which can be used to induce an immunogenic response. These immunogenic compositions may be manufactured in a manner that is itself known, e.g. by means of conventional mixing, dissolving, granulating, dragee-making, levigating, emulsifying, encapsulating, entrapping or lyophilizing processes. Proper formulation is dependent upon the route of administration chosen.

When a therapeutically effective amount of protein or other active ingredient of the present invention is administered by intravenous, cutaneous or subcutaneous injection, protein or other active ingredient of the present invention will be in the form of a pyrogen-free, parenterally acceptable aqueous solution. The preparation of such parenterally acceptable protein or other active ingredient solutions, having due regard to pH, isotonicity, stability, and the like, is within the skill in the art. An isotonic vehicle such as Sodium Chloride Injection, Ringer's Injection, Dextrose Injection, Dextrose and Sodium Chloride Injection, Lactated Ringer's Injection, Hanks's solution, physiological saline buffer, or other vehicle as known in the art can be used to formulate the solution. The immunogenic composition of the present invention may also contain stabilizers, preservatives, buffers, antioxidants, or other additives known to those of skill in the art. For transmucosal administration, penetrants appropriate to the barrier to be permeated are used in the formulation. Such penetrants are generally known in the art.

For oral administration, the compounds can be formulated readily by combining the active compounds with immunogenic acceptable carriers well known in the art. Such carriers enable the compounds of the invention to be formulated as powder, tablets, pills, dragees, capsules, liquids, gels, syrups, slurries, suspensions, solution, elixir, and the like, for oral ingestion by an animal to be treated Immunogenic preparations for oral use can be obtained solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. When administered in liquid form, a liquid carrier such as water, petroleum, oils of animal or plant origin such as peanut oil, mineral oil, soybean oil, or sesame oil, or synthetic oils may be added. The liquid form of the immunogenic composition may further contain physiological saline solution, dextrose or other saccharide solution, or glycols such as ethylene glycol, propylene glycol or polyethylene glycol. Dyestuffs or pigments may be added to the tablets or dragee coatings for identification or to characterize different combinations of active compound doses.

Immunogenic preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

All formulations for oral administration should be in dosages suitable for such administration. For buccal administration, the compositions may take the form of tablets or lozenges formulated in conventional manner Capsules and cartridges may be formulated containing a powder mix of the compound and a suitable powder base such as lactose or starch. The compounds may be formulated for parenteral administration by injection, e.g., by bolus injection or continuous infusion. Formulations for injection may be presented in unit dosage form, e.g., in ampules or in multi-dose containers, with an added preservative. The compositions may take such forms as suspensions, solutions or emulsions in oily or aqueous vehicles, and may contain formulatory agents such as suspending, stabilizing and/or dispersing agents.

Immunogenic formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions. Alternatively, the active ingredient maybe in powder form for constitution with a suitable vehicle, e.g., sterile pyrogen-free water, before use.

A carrier for hydrophobic compounds of the invention can be a co-solvent system comprising benzyl alcohol, a non-polar surfactant, a water-miscible organic polymer, and an aqueous phase. The co-solvent system may be the VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) consists of VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may substitute for dextrose.

Alternatively, other delivery systems for hydrophobic immunogenic compounds may be employed. Liposomes and emulsions are well known examples of delivery vehicles or carriers for hydrophobic drugs. Liposomes include amphipathic agents such as lipids which exist in aggregated form as micelles, insoluble monolayers, liquid crystals, or lamellar layers in aqueous solution. Suitable lipids for liposomal formulation include, without limitation, monoglycerides, diglycerides, sulfatides, lysolecithins, phospholipids, saponin, bile acids, and the like. Preparation of such liposomal formulations is within the level of skill in the art.

Additionally, the compounds may be delivered using a sustained-release system, such as semipermeable matrices of solid hydrophobic polymers containing the therapeutic agent. Various types of sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein or other active ingredient stabilization may be employed.

The immunogenic compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols. Many of the active ingredients of the invention may be provided as salts with immunogenically compatible counter ions. Such immunogenically acceptable base addition salts are those salts which retain the biological effectiveness and properties of the free acids and which are obtained by reaction with inorganic or organic bases such as sodium hydroxide, magnesium hydroxide, ammonia, trialkylamine, dialkylamine, monoalkylamine, dibasic amino acids, sodium acetate, potassium benzoate, triethanol amine and the like.

The immunogenic composition of the invention may be in the form of a complex of the protein(s) or other active ingredient of present invention along with protein or peptide antigens.

The immunogenic compositions and vaccines described herein can also be multivalent immunogenic compositions that further comprise additional polypeptides or nucleic acid sequences encoding additional polypeptides from other viruses.

The immunogenic compositions and vaccines described herein can also be multivalent immunogenic compositions that further comprise additional polypeptide fragments or nucleic acid sequences encoding additional polypeptide fragments from other viruses.

The immunogenic compositions and vaccines described herein can also be multivalent immunogenic compositions that further comprise additional viruses (e.g. viruses that are either attenuated, killed or otherwise deactivated) or nucleic acid sequences encoding additional viruses (e.g. viruses that are either attenuated, killed or otherwise deactivated).

The immunogenic compositions and vaccines described herein can also comprise fusions proteins, or nucleic acids encoding fusion proteins comprising a TiLV polypeptide, or a fragment or a variant thereof, and at least one polypeptide, or a polypeptide fragment or variant from another virus.

Other viral polypeptides and nucleic acid sequence suitable for use in the immunogenic compositions described herien are discussed in Tucker et al. (2000) "Assessment of DNA vaccine potential for juvenile Japanese flounder *Paralichthys olivaceus*, through the introduction of reporter genes by particle bombardment and histopathology" *Vaccine* 19(7-8):801; Corbeil et al. (1999) "Evaluation of the protective immunogenicity of the N, P, M, NV, G proteins of infectious hematopoietic necrosis virus in rainbow trout Oncorhynchus mykiss using DNA vaccines" *Dis. Aquat. Organ* 39(1):29; Nusbaum et al. (2002) "Protective immunity induced by DNA vaccination of channel catfish with early and late transcripts of the channel catfish herpes virus (IHV-1)" *Vet Immunol. Immunopathol.* 84:151; Clark et al. (1992) "Developmental expression of surface antigen genes in the parasitic cilate *Ichtyophthirius multifiliis*" *Proc. Natl. Acad. Sci.* 89(14):6363-6367; and Sato et al. (2000) "Expression of YAV proteins and vaccination against viral ascites among cultured juvenile yellowtail" *Biosci. Biotechnol. Biochem.* 64:1494. Numerous nucleic acid and amino acid sequences of fish pathogen antigens are known and accessible through the Genbank databases and other sources.

Other additives that are useful in immunogenic composition and vaccine formulations are known and will be apparent to those of skill in the art.

In one aspect, vaccination of animals may be performed by directly injecting the TiLV polypeptides, fragments or variants thereof into the animal to generate an immunogenic response. In certain embodiments, the TiLV polypeptide can be injected by themselves, or an immunogenic TiLV compositions comprising other components, including for example, excipients, additives and adjuvants.

Vaccination may also be performed by direct vaccination with a DNA encoding a TiLV polypeptide. When using such vaccines, the nucleic acid is administered to the animal, and the immunogenic polypeptide(s) encoded by the nucleic acid are expressed in the animal, such that an immune response against the proteins or peptides is generated in the animal. Subunit vaccines may also be proteinaceous vaccines, which contain the viral proteins or subunits themselves, or portions of those proteins or subunits. Any suitable plasmid or expression vector capable of driving expression of a polypeptide may be used. Plasmids and expression vectors include a promoter for directing transcription of the nucleic acid. The nucleic acid sequence encoding TiLV polypeptides may also be incorporated into a suitable recombinant virus for administration to the animal. Examples of suitable viruses include, but are not limited to, vaccinia viruses, retroviruses, adenoviruses and adeno-associated viruses. One of skill in the art will be able to select a suitable plasmid, expression vector, or recombinant virus for delivery of the TiLV nucleic acid sequences of the invention. Direct vaccination with DNA encoding proteins has been successful for many different proteins. (As reviewed in for example Donnelly et al. (1993) The Immunologist 2: 20-26 (1993)).

Vaccination with the TiLV nucleic acids and polypeptides described herein can also be performed using live recombinant carriers capable of expressing the polypeptides described herein. Live recombinant carriers are micro-organisms or viruses in which additional genetic information, e.g. a nucleic acid sequence encoding a TiLV polypeptide, or a fragment thereof has been cloned. Fish infected with such live recombinant carriers will produce an immunological response not only against the immunogens of the carrier, but also against the TiLV polypeptide or TiLV polypeptide fragment.

Alternatively, passive vaccination can be performed by raising TiLV antibodies in a first animal species (e.g. a rabbit), from antibody-producing cell lines, or from in vitro techniques before administering such antibodies (in purified or unpurified form) to second animal species. This type of passive vaccination can be used when the second animal is already infected with a TiLV. In some cases, passive vaccination can be useful where the infection in the second animal cannot, or has not had sufficient time to mount an immune response to the infection.

Many methods for the vaccination of fish are known in the art. For example, vaccination with the TiLV nucleic acids and polypeptides described herein can be performed in fish by injection, immersion, dipping or through oral administration. The administration protocol can be optimized in accordance with standard vaccination practice For oral vaccination of tilapia, the TiLV nucleic acids, polypeptides or immunogenic compositions described herein can be mixed with feed, coated on the feed or be administered in an encapsulated form. In certain embodiments, vaccination may be performed by incubating live feed in a TiLV vaccine suspension prior to feeding an animal (e.g. a tilapia) such that ingestion of the live feed will cause the TiLV vaccine to accumulate in the digestive tract of the animal undergoing vaccination. One skilled in the art will appreciate that these methods of administration may expose an antigen to potential breakdown or denaturation and thus the skilled artisan will ensure that the method of vaccination will be appropriate for a chosen antigen. In the case of oral vaccination, the vaccine may also be mixed with one or more carriers. Carriers suitable for use in oral vaccination include both metabolizable and non-metabolizable substances.

Vaccination of tilapia can also be performed by immersion protocols. Skin and gill epithelia in fish have mucosal surfaces that contribute to the recognition of pathogens by adsorbing antigens. Adsorption in turn results in the activation of antibody producing cells as part of the immune response. Thus in one embodiment, vaccination of fish with the polypeptides described herein can be performed by immersing fish in water containing a TiLV vaccine composition. At least two types of immersion vaccination can be used in conjunction with the polypeptides described herein. In dip vaccination, fish are immersed in water comprising for a short period of time (e.g. about 30 seconds) in a concentrated vaccine solution (e.g. 1 part vaccine, 9 parts water). In bath vaccination, immersion occurs for longer periods of time (e.g. several hours) in water containing lower vaccine concentrations. One skilled in the art will readily be able to determine the dilution of TiLV vaccine and the duration of immersion sufficient to induce an immune reaction in an immersion protocol.

Another method for vaccinating tilapia with the TiLV nucleic acids and polypeptides described herein is by injection vaccination. In injection vaccination, a vaccine is injected into the abdominal cavity of the fish. Although one skilled in the art can readily determine the proper injection point, a common site for needle insertion in tilapia is the midline of the abdomen, one pelvic fin length in front of the base of the pelvic fins. In certain embodiments, the TiLV nucleic acids, polypeptides or immunogenic compositions can be delivered into the body cavity of the fish in an oil emulsion, or other adjuvants or additives that enhance and/or prolong immune responses. In addition to intraperitoneal injection, injection vaccination can also be performed by intramuscular injection. One skilled in the art will appreciate that improper handling and needle insertion can cause mortality of fish and thus light anesthesia may be used during the vaccination process to reduce stress and mechanical injury to the animals. The skilled artisan will also appreciate that needles having the proper length and thickness can be important to ensure proper vaccination while avoiding secondary complications due to infection, inflammation or tissue damage.

The TiLV nucleic acids, polypeptides or immunogenic compositions described herein can also be delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges may be formulated containing a powder mix of the compound and a suitable powder base such as lactose or starch.

The TiLV nucleic acids, polypeptides or immunogenic compositions described herein can be administered in any immunologically effective amount sufficient to trigger an immune response in an animal. In certain instances, this amount can be between about 0.01 and about 1000 micrograms of the TiLV nucleic acid, polypeptide or immunogenic composition per animal.

An "immunologically effective amount" of the compositions of the invention may be administered to an animal or a human. As used herein, the term "immunologically effective amount" refers to an amount capable of inducing, or enhancing the induction of, the desired immune response in an animal or a human. The desired response may include, inter alia, inducing an antibody or cell-mediated immune response, or both. The desired response may also be induction of an immune response sufficient to ameliorate the symptoms of a TiLV associated disease and/or provide protective immunity in an animal or a human against subsequent challenge with a TiLV. An immunologically effective amount may be an amount that induces actual "protection" against TiLV associated diseases, meaning the prevention of any of the symptoms or conditions resulting from TiLV associated disease in animals or humans. An immunologically effective amount may also be an amount sufficient to delay the onset of symptoms and conditions associated with infection, reduce the degree or rate of infection, reduce in the severity of any disease or symptom resulting from infection, and reduce the viral load of an infected animal or a human One of skill in the art can readily determine what is an "immunologically effective amount" of the compositions of the invention without performing any undue experimentation. An effective amount can be determined by conventional means, starting with a low dose of and then increasing the dosage while monitoring the immunological effects. Numerous factors can be taken into consideration when determining an optimal amount to administer, including the size, age, and general condition of the animal, the presence of other drugs in the animal, the virulence of the particular TiLV against which the animal is being vaccinated, and the like. The actual dosage is can be chosen after consideration of the results from various animal studies.

The immunologically effective amount of the immunogenic composition may be administered in a single dose, in divided doses, or using a "prime-boost" regimen. The compositions may be administered by any suitable route, including, but not limited to parenteral, intradermal, transdermal, subcutaneous, intramuscular, intravenous, intraperitoneal, intranasal, oral, or intraocular routes, or by a combination of routes. The compositions may also be administered using a "gun" device which fires particles, such as gold particles, onto which compositions of the present invention have been coated, into the skin of an animal. The skilled artisan will be able to formulate the immunogenic composition according to the route chosen.

Dose sizes of the immunogenic compositions described herein can be in the range of about 0.1 to 2.0 ml depending on the route of administration, but dose sizes are not limited to this range. For inactivated TiLV compositions can contain suitable $TCID_{50}$ levels of virus prior to inactivation. The antigen content in TiLV preparation can have, but is not limited to, a titer of between 10 to 10,000 units/ml as the amount administered per dose. One of skill in the art will readily be capable of determining a suitable antigen content for the immunogenic compositions described herein.

For immunogenic compositions containing modified live TiLV or attenuated TiLV, a therapeutically effective dose can be determined by one of skill in the art. For immunogenic compositions containing TiLV subunit antigens, a therapeutically effective dose can be determined by one of skill in the art. While the amounts and concentrations of adjuvants and additives useful in the context of the present invention can readily be determined by the skilled artisan.

Cells Comprising TiLV and Uses Thereof

TiLV can be used to infect cells. Cells may be cultured in any useful media and any permissive cell or tissues, which may be, or may be derived from fish cell, including, but not limited to tilapia cells, CHSE-214 *Oncorhynchus tshawytscha* cells, BF-2 *Lepomis macrocturus* cells; BB *Ictalurus nebulosus* cells, EPC *Cyprinus carpio* cells, KF-1 *Cyprinus carpio* cells, RTG-2 *Salmo gairdneri* cells, FHM *Pimephales promelas* cells, and E-11 *Ophicephalus striatus* cells. As used herein, a cell or a tissue can include, but is not limited to individual cells, tissues, organs, insect cells, rodent cells, avian cells, mammalian cells, hybridoma cells, primary cells, continuous cell lines, and/or genetically engineered cells. Cell lines suitable for propagating, growing, or harboring TiLV nucleic acid sequence or for expressing a polypeptide produced by the TiLV nucleic acid sequence include, tilapia cells, CHSE-214 *Oncorhynchus tshawytscha* cells, BF-2 *Lepomis macrocturus* cells; BB *Ictalurus nebulosus* cells, EPC *Cyprinus carpio* cells, KF-1 *Cyprinus carpio* cells, RTG-2 *Salmo gairdneri* cells, FHM *Pimephales promelas* cells, and E-11 Ophicephalus *striatus* cells as well as non-fish cells but are not limited to dog kidney cells, BSC-1 cells, LLC-MK cells, CV-1 cells, CHO cells, COS cells, murine cells, human cells, HeLa cells, 293 cells, VERO cells, MDBK cells, MDCK cells, MDOK cells, CRFK cells, RAF cells, TCMK cells, LLC-PK cells, PK15 cells, WI-38 cells, MRC-5 cells, T-FLY cells, BHK cells, SP2/0 cells, NS0, PerC6 (human retina cells), chicken embryo cells or derivatives, embryonated egg cells, embryonated chicken eggs or derivatives thereof.

Cell culture media formulations to suitable for culturing cells infected with TiLV viruses described herein include, but are not limited to, Modified Eagle's media MEM, minimum essential media MEM, Dulbecco's modified Eagle's media D-MEM, D-MEM-F12 media, William's E media, RPMI media, HyClone cell culture medium (HyClone, Logan, Utah); and serum-free basal epithelial medium (CellnTech), and analogues and derivative thereof. These can also be specialty cell cultivation and virus growth media as VP-SFM, OptiPro™ SFM, AIM V.R media, HyQ SFM4 MegaVir, EX-CELL Vero SFM, EPISERF, ProVero, any 293 or CHO media and analogues and derivatives thereof. The culture media described herein can be supplemented by any additive known from prior art that is applicable for cell and virus cultivation as for example animal sera and fractions or analogues thereof, amino acids, growth factors, hormones, buffers, trace elements, trypsin, sodium pyruvate, vitamins, L-glutamine and biological buffers. One medium is OptiPRO SFM supplemented with L-glutamine and trypsin. In certain embodiments, the cell culture media can be supplemented with 0.1 to 10 units of trypsin. Alternatively, plant derived equivalents of trypsin (e.g. Accutase) ranging from 2-100 units can also be used in cell culture. Cell culture media can be used in the absence or presence of animal-derived components. An example of supplementation with an animal-derived component is gamma-irradiated serum ranging from 0.5-10% final concentration.

An expression vector can be introduced into cells in order to produce proteins (for example, SEQ ID NO: 12 and fragments and variants described thereof herein) encoded by nucleotide sequences of the invention (for example any of SEQ ID NOs: 1-11 and fragments and variants thereof described herein). Cells can harbor an expression vector via introducing the expression vector into an appropriate host cell via methods known in the art.

An expression vector can be introduced into cells in order to produce proteins encoded by nucleotide sequences of the invention (for example any of SEQ ID NOs: 1-11 or a sequence complementary to any of SEQ ID NOs: 1-11 and fragments and variants thereof described herein). Cells can harbor an expression vector via introducing the expression vector into an appropriate host cell via methods known in the art.

A eukaryotic expression vector can be used to transfect cells in order to produce proteins (for example, SEQ ID NO: 12 or proteins encoded by SEQ ID NOs: 1-11) and fragments and variants described herein encoded by nucleotide sequences of the vector.

An exogenous nucleic acid (for example any of SEQ ID NOs: 1-11, a cDNA of any of SEQ ID NOs: 1-11 or a cDNA complementary to any of SEQ ID NOs: 1-11, fragments, or variants thereof described herein) can be introduced into a cell via a variety of techniques known in the art.

A eukaryotic expression vector can be used to transfect cells in order to produce proteins encoded by nucleotide sequences (for example any of SEQ ID NOs: 1-11, a cDNA of any of SEQ ID NOs: 1-11 or a cDNA complementary to any of SEQ ID NOs: 1-11, fragments, or variants thereof described herein). Mammalian cells can harbor an expression vector via introducing the expression vector into an appropriate host cell via methods known in the art.

An exogenous nucleic acid can be introduced into a cell via a variety of techniques known in the art, such as lipofection, microinjection, calcium phosphate or calcium chloride precipitation, DEAE-dextrin-mediated transfection, or electroporation. Other methods used to transfect cells can also include calcium phosphate precipitation, modified calcium phosphate precipitation, polybrene precipitation, microinjection liposome fusion, and receptor-mediated gene delivery. The expression vectors can contain coding sequences, or portions thereof, encoding the proteins for expression and production. Expression vectors containing sequences encoding the produced proteins and polypeptides, as well as the appropriate transcriptional and translational control elements, can be generated using methods well known to and practiced by those skilled in the art. These methods include synthetic techniques, in vitro recombinant DNA techniques, and in vivo genetic recombination which are described in Sambrook et al., and Ausubel et al.

Cells to be infected with TiLV or nucleic acids thereof (for example any of SEQ ID NOs: 1-11, a cDNA of any of SEQ ID NOs: 1-11 or a cDNA complementary to any of SEQ ID NOs: 1-11, fragments, or variants thereof) can be primary and secondary cells, which can be obtained from various tissues and include cell types which can be maintained and propagated in culture.

Cells maintained in culture can be passaged by their transfer from a previous culture to a culture with fresh medium. In one embodiment, induced epithelial cells are stably maintained in cell culture for at least 3 passages, at least 4 passages, at least 5 passages, at least 6 passages, at least 7 passages, at least 8 passages, at least 9 passages, at least 10 passages, at least 11 passages, at least 12 passages, at least 13 passages, at least 14 passages, at least 15 passages, at least 20 passages, at least 25 passages, or at least 30 passages.

In one embodiment, cells that have been infected with TiLV or contain nucleic acids thereof (for example any of SEQ ID NOs: 1-11, a cDNA of any of SEQ ID NOs: 1-11 or a cDNA complementary to any of SEQ ID NOs: 1-11, fragments, or variants thereof described herein) can express a variety of markers that distinguish them from uninfected cells. Expression of markers can be evaluated by a variety of methods known in the art. The presence of markers can be determined at the DNA, RNA or polypeptide level.

In one embodiment, the method can comprise detecting the presence of a marker gene polypeptide expression. Polypeptide expression includes the presence of a marker gene polypeptide sequence, or the presence of an elevated quantity of marker gene polypeptide as compared to non-epithelial cells. These can be detected by various techniques known in the art, including by sequencing and/or binding to specific ligands (such as antibodies). For example, polypeptide expression maybe evaluated by methods including, but not limited to, immunostaining, FACS analysis, or Western blot. These methods are well known in the art In another embodiment, the method can comprise detecting the presence of nucleic acids (for example any of SEQ ID NOs: 1-11, a cDNA of any of SEQ ID NOs: 1-11 or a cDNA complementary to any of SEQ ID NOs: 1-11, fragments, or variants thereof). RNA expression includes the presence of an RNA sequence, the presence of an RNA splicing or processing, or the presence of a quantity of RNA. These can be detected by various techniques known in the art, including by sequencing all or part of the marker gene RNA, or by selective hybridization or selective amplification of all or part of the RNA. In one embodiment, in situ hybridization can be used to detect TiLV nucleic acids.

The resulting transformed cells can be used for basic research as well as testing for therapeutic and prophylactic agents. Specifically, for the latter, the host cells can be incubated and/or contacted with a potential therapeutic or prophylactic agent. The resulting expression of the gene construct can be detected and compared to the expression of the gene construct in the cell before contact with the agent.

These gene constructs as well as the host cells transformed with these gene constructs can also be the basis for transgenic animals for testing both as research tools and for therapeutic and prophylactic agents. Such animals would include but are not limited to, nude mice and fish. Phenotypes can be correlated to the genes and looked at in order to determine the genes effect on the animals as well as the change in phenotype after administration or contact with a potential therapeutic agent.

A further embodiment of the present invention is a method and/or assay for screening and/or identifying a test agent for the prevention and/or treatment of TiLV comprising contacting or incubating a test agent to a nucleotide comprising the nucleic acid sequence of SEQ ID NOs: 1-11 or fragments or variants thereof as described herein, and determining if the test agent binds to the nucleotide, wherein if the test agent binds to the nucleotide, the test agent is identified as a therapeutic and/or preventative agent for TiLV.

A further embodiment of the present invention is a method and/or assay for screening and/or identifying a test agent for the prevention and/or treatment of TiLV comprising contacting or incubating a test agent to a nucleotide comprising the nucleic acid sequence of SEQ ID NOs: 1-11 or fragments or variants thereof as described herein, and detecting the expression of the nucleotide before and after contact or incubation with the test agent, wherein if the expression of the nucleotide is decreased after the contact or incubation with the test agent, the test agent is identified as a therapeutic and/or preventative agent for TiLV.

A further embodiment of the present invention is a method and/or assay for screening and/or identifying a test agent for the prevention and/or treatment of TiLV comprising contacting or incubating a test agent to a gene construct comprising a nucleotide comprising the nucleic acid sequence of SEQ ID NOs: 1-11 or fragments or variants thereof as described herein, and detecting the expression of the nucleotide in the gene construct before and after contacting or incubating the test agent with the gene construct, wherein if the expression of the gene is reduced or decreased after contact with the test agent or compound, the test agent is identified as a therapeutic and/or preventative agent for TiLV.

A further embodiment of the present invention is a method and/or assay for screening and/or identifying a test agent for the prevention and/or treatment of TiLV comprising transforming a host cell with a gene construct comprising a nucleotide comprising the nucleic acid sequence of SEQ ID NOs: 1-11 or fragments or variants thereof as described herein, detecting the expression of the nucleotide in the host cell, contacting the test agent with the host cell, and detecting the expression of the nucleotide in the host cell after contact with the test agent or compound, wherein if the expression of the nucleotide is reduced or decreased after contact with the test agent or compound, the test agent is identified as a therapeutic and/or preventative agent for TiLV.

The expression of a nucleotide or gene can be determined using a measurable phenotype, either one that is native to the gene or one that is artificially linked, such as a reporter gene.

A further embodiment is a method and/or assay for screening and/or identifying a test agent for the prevention and/or treatment of TiLV, comprising contacting or incubating the test agent with a polypeptide encoded by a nucleotide sequence of SEQ ID NOs: 1-11, or a fragment or variant thereof, and detecting the presence of a complex between the test agent and the polypeptide, wherein if a complex between the test agent and the polypeptide is detected, the test agent is identified as a prevention and/or treatment for TiLV.

A further embodiment is a method and/or assay for screening and/or identifying a test agent for the prevention and/or treatment of TiLV, comprising contacting or incubating the test agent with a polypeptide encoded by a nucleotide sequence of SEQ ID NOs: 1-11, or a fragment or variant thereof and a known ligand of the polypeptide, and detecting the presence of a complex between the test agent and the ligand, wherein if a complex between the test agent and the ligand is detected, the test agent is identified as a prevention and/or treatment for TiLV.

Another embodiment of the present invention is a method and/or assay for screening and/or identifying a test agent for the prevention and/or treatment of TiLV, comprising contacting or incubating the test agent with a polypeptide encoded by a nucleotide sequence of SEQ ID NOs: 1-11, or a fragment or variant thereof and a known antibody of the polypeptide, and detecting the presence and quantity of unbound antibody, wherein the presence of the unbound antibody indicates that the test agent is binding to the polypeptide, and the test agent is identified as a prevention and/or treatment for TiLV.

High throughput screening can also be used to screen the test agents. Small peptides or molecules can be synthesized and bound to a surface and contacted with the polypeptides, and washed. The bound peptide is visualized and detected by methods known in the art.

The invention also provides for polypeptides to be used for rational drug design where structural analogs of biologically active polypeptides can be designed. Such analogs would interfere with the polypeptide in vivo, such as by non-productive binding to target. In this approach the three-dimensional structure of the protein is determined by any method known in the art including but not limited to x-ray crystallography, and computer modeling. Information can also be obtained using the structure of homologous proteins or target-specific antibodies.

Using these techniques, agents can be designed which act as inhibitors or antagonists of the polypeptides, or act as decoys, binding to target molecules non-productively and blocking binding of the active polypeptide.

The term "agent" as used herein means a substance that produces or is capable of producing an effect and would include, but is not limited to, chemicals, pharmaceuticals, biologics, small organic molecules, antibodies, nucleic acids, peptides, and proteins.

EXAMPLES

The present invention may be understood by reference to the following non-limiting examples, which are presented in order to more fully illustrate the preferred embodiments of the invention. They should in no way by construed to limit the broad scope of the invention.

Example 1—Materials and Methods Used for Examples 2-9

Cell Culture: Eight established fish cell lines were used in this study: (1) CHSE-214 (ATCC CRL 1681) from the Chinook salmon *Oncorhynchus tshawytscha*; (2) BF-2 (ATCC CCL 91), derived from the bluegill *Lepomis microptерus*; (3) BB (ATCC CCL 59), from the brown bullhead *Ictalurus nebulosus*; (4) and (5) EPC (ATCC CRL 2872 and KF-1), from the common carp *C. carpio*; (6) RTG-2 (ATCC CCL 55), from the rainbow trout *Salmo gairdneri*; (7) FHM (ATCC CCL 42), from the fat head minnow *Pimephales promelas*; and (8) E-11, from the striped snakehead *Ophicephalus striatus* (generously provided by M. Ucko, Israel Oceanographic and Limnological Research). In addition, a culture of primary tilapia brain cells was generated, developed as previously described in Hasegawa et al. 1997 and Hedrick et al. 2000. Briefly, commercial Nile tilapia (*O. niloticus*) (50 grams) were euthanized by anesthetic overdose (600 mg/liter tricaine methanesulfonate [MS-222]; Finquel, USA), and the brains were removed aseptically. The minced brains were manually homogenized and passed through a 100μ mesh grinders. The cells were then washed and seeded in 12.5-ml sealed flasks (Becton-Dickinson, San Francisco, Calif., USA) at 25° C. The initial culture medium contained 80% Leibovitz (L-15) medium (Gibco, USA), 10% inactivated fetal calf serum (FCS) (Gibco), and 10% inactivated tilapia serum medium, supplemented with L-glutamine (300 mg/liter), HEPES (1%), penicillin (100 □g/ml), streptomycin (100 □g/ml), and amphotericin B (0.25 □g/ml).

During the first 21 days of incubation, 50% of the media were changed every week. Thereafter, the monolayers were trypsinized and transferred into new 25-ml flasks (Cellstar; Greiner Bio-One, Germany) with a 1:1 mixture of conditioned medium (from old cultures) and fresh medium. The cultures of the primary cells were passaged every other week. After 35 passages, the tilapia serum and the condition media were omitted, and the cells were split (at a ratio of 1:2) every 2 to 3 weeks in regular medium (L-15 with 5% inactivated FCS).

Viruses and virus culture: A total of 25 tilapia lake virus (TiLV) isolates were collected from suspected outbreaks that occurred between May 2011 and June 2013. The isolations were obtained from all Israeli regions where fish are commercially cultured: the coastal shore (2 isolations); the Jordan Valley (comprising the Bet-Shean Valley and the Yizrael Valley; 9 isolations); and Upper and Lower Galilee (3 isolations). In addition, 11 isolations were obtained from various species of wild tilapines from the Sea of Galilee. An outbreak of farmed fish was defined as a sudden and unexplained rise in mortality (2% or more daily) for at least three consecutive days. If two wards were simultaneously affected on the same farm, these were classified as a single outbreak. Therefore, each isolate represents a distinct clinical outbreak. Viruses from wild fish displaying ocular lesions were isolated from commercially caught fish in the Sea of Galilee; each isolate represents a different catch. Fish weighing 20 to 200 grams or 40 to 350 grams (wild and farmed fish, respectively) were collected during the hot seasons (May to October; water temperature, between 22 and 32° C.). To minimize contamination risks, the brains and viscera (kidneys, livers, spleens, and hearts) of the suspected fish were removed aseptically, pooled, and manually homogenized with nine volumes of Hanks' balanced salt solution (HBSS), centrifuged at 3,000×g for 10 minutes, and the supernatants were filtered through 0.22µ filters (Sarstedt, Germany) The filtrates were stored at −80° C. until use. For infection, monolayers (about 90% confluence) were washed twice with HBSS and incubated with 500 µl of the virus filtrate at 25° C. for 1 hour, after which the cells were washed with HBSS, supplemented with L-15 medium (2% FCS), and incubated at 25° C. The cultures were observed daily for 21 days for cytopathic effects (CPE). In experiments where the tilapine disease was reproduced by virus injection, a virus named TiLVx2 was also used, which was purified by two successive rounds of endpoint dilution assays. This was performed with E-11 cultures, infected with serial dilutions of TiLV (isolate 4/2011; obtained from the brain of a diseased St. Peter's fish that was collected from the Kinneret Lake on June 2011).

Titration of virus: The original virus-containing culture supernatant (isolate 4/2011) was cultured in E-11 cells and serially diluted in 10-fold increments with HBSS and 50 µl from each dilution was inoculated onto E-11 monolayers in 96-well plates. Four wells were used for each diluted sample. The plates were incubated at 25° C. and observed daily for CPE. After 7 days, the 50% tissue culture infectious dose ($TCID_{50}$) ($ml^{-1}$) was calculated by the method of Reed and Muench 1938.

Electron microscopy analyses: For examinations of TiLV by transmission electron microscopy, E-11-infected cultures were scraped from the flask, centrifuged (2,000 rpm for 7 minutes), fixed with 1.5% glutaraldehyde in 0.1 M sodium cacodylate (pH 7.2) for 2 hours, and then rinsed five times in phosphate buffer (pH 7.2). The pellets, consisting of infected E-11 cells, were post-fixed in 1% $OsO_4$ in phosphate buffer and dehydrated with increasing concentrations of ethanol. The pellets were then washed twice with 100% propylene oxide and treated with propylene oxide-Epon (3:1) for 30 minutes, followed by propylene oxide-Epon (1:1) for 15 minutes. Finally, the pellets were embedded in 100% Epon and left overnight. Thin sections (70 to 90 nm) were placed on Formvar-coated copper grids and stained with uranyl acetate, followed by lead citrate, according to the Reynolds method (Reynolds 1963). All micrographs were taken with a JEOL 1200-EX electron microscope operating at 60 or 80 kV (Electron Microscopy [EM] Unit, Institute of Biotechnology, Bar-Ilan University, Israel). EM analysis of the negatively stained virion pellets was carried at the EM Unit, Tel Aviv University, exactly as described before in Oberpichler et al. 2008, with an A JEM 1200-EX transmitting electron microscope (JEOL-USA, Peabody, Mass., USA). The virions for this analysis were pelleted by ultracentrifugation through 25% sucrose cushions.

Purification of virus from culture supernatants using sucrose gradient fractionation: Cultured E-11 cells were infected with TiLV (isolate 4/2011), and the culture supernatant was cleared from the cell debris by centrifugation (10 minutes at 3,000 rpm). The supernatant was layered onto 2 ml of a 30% (wt/vol) sucrose-Tris-EDTA (TE) buffer cushion and centrifuged for 2 h in a T865 rotor at 65,000 rpm (Sorvall Discovery 90SE). The pellet was resuspended in TE buffer and layered onto a sucrose step gradient (Bacharach et al. 2000; Laham and Bacharach 2007; Melamed et al. 2004). The gradient consisted of 3-ml layers with sucrose concentrations of 70, 60, 50, 40, 30, 20, and 10% (wt/vol) in TE, from bottom to top. Ultracentrifugation was performed in a TST41.14 rotor for 2 hours at 40,000 rpm (Sorvall Discovery 90SE). One-milliliter fractions were taken from the top of the gradient, and the virions were pelleted from each fraction by ultracentrifugation (for 2 hours at 65,000 rpm; T865 rotor; Sorvall Discovery 90SE) and resuspended in 1 ml of TE buffer. 100 µl aliquots from each sample were incubated with naive E-11 cells to monitor for CPE. The incubation of cultures with negative controls, consisting of aliquots from fractions of an identical sucrose gradient but with no addition of culture supernatants, resulted in no CPE.

Isolation of nucleic acids from purified virions and cDNA synthesis: Nucleic acids were extracted from purified virion pellets using peqGOLD Trifast for RNA (Peqlab, Germany) or the High Pure PCR template preparation kit for DNA (Roche, Germany) Reverse transcription was performed with the Verso cDNA kit (Thermo, Lithuania), according to the manufacturer's instructions. To identify TiLV-specific sequences, the supernatants of TiLV (isolate 4/2011)-infected E-11 cultures were cleared from the cell debris by centrifugation (for 10 minutes at 3,000×g), and the purified supernatants were subjected to further purification by ultracentrifugation (for 2 hours in a T865 rotor at 65,000 rpm [Sorvall Discovery 905E]) through a 30% sucrose cushion. The pellet was resuspended in TE, and virions were further purified by sucrose cushions of 40 to 70% (wt/vol). After ultracentrifugation (TST41.14 rotor for 2 hours at 40,000 rpm; Sorvall Discovery 90SE), the 40% sucrose fraction was collected, and virions were pelleted by additional ultracentrifugation (TST41.1 rotor for 2 hours at 40,000 rpm; Sorvall Discovery 90SE). RNA was extracted from the pellets by guanidine thiocyanate (peqGOLD Trifast; Peqlab). cDNA was generated by reverse transcription and random priming, using the purified RNA as a template. The fragments of this cDNA were isolated by shotgun cloning (Nehls and Boehm 1995).

Shotgun cloning by random priming: Shotgun cloning was performed as described by Nehls and Boehm. The purified cDNA (approximately 10 ng) was double primed with MluI(N)6 primer (GGAACT-CAATGCACGCGTNNNNNN) (SEQ ID NO: 13) using ReddyMix PCR master mix (Thermo, Lithuania). The primed products were amplified by PCR with MluI primer (GGAACTCAATGCACGCGT) (SEQ ID NO: 14) and cloned into the pJET1.2/blunt vector (CloneJET; Fermentas/Thermo, Lithuania), which was transformed into *Escherichia coli* strain HIT-DH5α cells (Real Biotech, Taiwan). Ampicillin-resistant transformants, grown at 37° C. on LB agar plates containing 100 µg/ml ampicillin, were picked and grown overnight in 5 ml of LB supplemented with 100 µg/ml ampicillin. Plasmid DNA was isolated using the HiYield plasmid minikit (RBC, Taiwan). The inserts were amplified by PCR using the pJET1.2-derived primers, separated by electrophoresis in a 1.0% gel, placed in 1×Tris-acetate-EDTA (TAE) buffer at 80 V for 1.5 hours, stained with ethidium bromide, excised, and gel purified using the GeneJET gel extraction and DNA cleanup micro kit (Thermo, Lithuania). Single fragments were sequenced by Hy Laboratories (Israel) using ABI 3730. The sequences were analyzed for homologies to nucleotide sequences in the GenBank database using the nucleotide Basic Local Alignment Search Tool (BLASTn) and the Vector NTI 6 (InforMax, Inc.) software. Further searches of protein databases were done by BLASTx. The internal primers from each sequenced clone were tested for PCR amplification of the TiLV genome. The primers derived from clone 7450 specifically amplified the cognate sequence from TiLV-infected cultures, in reverse transcription-PCRs (RT-PCRs).

Rapid amplification of cDNA ends (RACE): To extend the sequence of clone 7450 obtained by shotgun cloning, 3' and 5' rapid amplification of cDNA ends (RACE) reactions were carried out as described before (Scotto-Lavino et al. 2006a; Scott-Lavino et al. 2006b), using total RNA that was extracted from TiLV-infected E11 cells by EZ-RNA reagent (Biological Industries). Briefly, for 3' RACE, cDNA was generated using primer $Q_T$ (CCAGTGAGCAGAGTGACGAGGACTCGAGCT-CAAGCTTTTTTTTTTTTTTTTTVN) (SEQ ID NO: 15) and the SuperScript III first-strand synthesis system for RT-PCR (catalog no. 18080-051; Invitrogen), according to the manufacturer's instructions. The cDNA was amplified with clone 7450/150R primer (TAT-CACGTGCGTACTCGTTCAGT) (SEQ ID NO: 16) that was derived from an internal sequence of the shotgun fragment, and with $Q_0$ primer (CCAGT-GAGCAGAGTGACG, (SEQ ID NO: 17) derived from $Q_T$ primer), using Ex-Taq enzyme (catalog no. RR001A; TaKaRa). The resulting PCR products were diluted 1:20 and were subjected to a second PCR with the nested primers $Q_1$ (GAGGACTCGAGCTCAAGC (SEQ ID NO: 18), derived from $Q_T$ primer) and E-11-inf-R (AAGTTCTCTTGCCTCTTGG (SEQ ID NO: 19), derived from the sequence of the shotgun fragment). For 5' RACE, cDNA was generated as above but with primer clone 7450/150F (CACCCAGACTTGCGGACATA) (SEQ ID NO: 20). Poly(A) tails were added to the cDNA using terminal transferase (catalog no. 3333566; Roche), according to the manufacturer's instructions. The tailed cDNA was amplified by PCR using primer E-11-inf-F (TCCAAGGAAACAGCT-GAGC (SEQ ID NO: 21), derived from the sequence of the shotgun fragment), together with a mixture of the Q0 and $Q_T$ primers. The resulting PCR products were diluted 1:20 and subjected to a second nested-PCR using the E11-inf-F-in (GAGGCAATATGGATTCTTCG) (SEQ ID NO: 22) and $Q_1$ primers.

RT-PCR: Samples from the brain, heart, head kidney, spleen, and liver were taken from clinical cases of suspected TiLV outbreaks, pooled, and directly frozen at −80° C. Total RNA was purified using peqGOLD Trifast (Peqlab, Germany), according to the manufacturer's instructions, followed by reverse transcription and amplification (Verso 1-step RT-PCR ReddyMix kit; Thermo, Lithuania). The random primers of the kit were substituted with the external specific primer ME1 (GTTGGGCACAAGGCATCCTA) (SEQ ID NO: 23) and clone 7450/150R (TAT-CACGTGCGTACTCGTTCAGT) (SEQ ID NO: 16). Cycling was performed at 50° C. for 15 minutes (reverse transcription), 95° C. for 2 minutes (enzyme inactivation), and 35 cycles at 95° C. for 30 seconds, 56° C. for 60 seconds, and 72° C. for 60 seconds; the reaction was terminated by 72° C. for 7 minutes. The PCR products were resolved in 1% agarose gels in 0.5×TAE buffer (40 mM Tris-acetate and 1 mM EDTA).

Nuclease sensitivity assays: The supernatant (9 ml) of a TiLV-infected E-11 culture was collected, and virions were purified and pelleted through a 25% (wt/vol) sucrose cushion, using ultracentrifugation (107,000×g at 4° C. for 2 hours). A supernatant of uninfected E-11 culture was used as a control. To digest free nucleic acids, the pellets were resuspended in 300 µl of 1×DNase buffer (10 mM Tris-HCl [pH 7.5], 2.5 mM $MgCl_2$, and 0.5 mM $CaCl_2$)) and were supplemented with 33 µg of RNaseA (Sigma R4642) and 1 U DNase (Baseline-ZERO DNase). The samples were incubated for 40 minutes at room temperature, after which each reaction mixture was diluted in 9 ml of Leibovitz (L-15) medium, supplemented with 5% FCS, and virions were pelleted as described above. To release nuclease protected nucleic acids from the virions and to digest possible leftovers of RNase A and DNase I, the pellets were resuspended in 150 µl of proteinase K buffer (50 mM Tris-HCl [pH 7.5], 100 mM NaCl, 10 mM EDTA, 1% SDS), supplemented with 100 µg/ml proteinase K (Roche), and the proteins were digested for 30 minutes at 37° C. The nucleic acids were extracted by phenol-chloroform-isoamyl alcohol (CIP) and were precipitated with ethanol, 0.3 M sodium acetate (pH 5.2), and glycogen as a carrier. The nucleic acids were resuspended in 20 µl of buffer (10 mM Tris-HCl [pH 8.3], 10 mM $MgCl_2$, 1 mM dithiothreitol [DTT], 60 mM NaCl), and 3 µl was added to 100 µl of RNase I buffer (100 mM NaCl, 50 mM Tris-HCl [pH 7.9], 10 mM $MgCl_2$, 1 mM DTT) with or without 50 units of RNase I (catalog no. M0243S; NEB). Digestion was carried out for 5 minutes at 37° C., and the nucleic acids were CIP extracted and precipitated as described above. The nucleic acids were resuspended in 20 µl of reverse transcription reaction mixture; a reaction without reverse transcriptase was also assembled to ensure the absence of protected DNA. The resulting cDNA was amplified with TiLV-specific primers (Nested ext-1 [TATGCAGTACTTTCCCTGCC] (SEQ ID NO: 24) and Nested ext-2 [TTGCTCTGAGCAAGAGTACC] (SEQ ID NO: 25)) or with snakehead retrovirus (SnRV)-specific primers (Snakehead gag-pol fw [CAGATCACTGATC-GATGC] (SEQ ID NO: 26) and Snakehead gag-pol rev [GTCTGAAAGGTAAGGTGG] (SEQ ID NO: 27)). The amplified products (491 and 284 bp for TiLV and SnRV, respectively) were separated by electrophoresis in 1% agarose gels.

Ether and chloroform sensitivity assays: TiLV sensitivity assays for ether and chloroform were performed as described before (Crandell et al. 1975; Hutoran et al. 2005).

Experimental reproduction of the disease and ethical issues: The tilapine species used in this study, O. niloticus (strain Chitralada), was grown at a specific-pathogen-free (SPF) facility (UV-treated pathogen free environment) at a constant temperature of 28° C. The fish were fed a daily regimen of 2% (wt/wt); the water parameters ($O_2$>5 ppm, NH4+<1 ppm, NaCl <1 ppt) were kept constant. All experimentally induced infections were carried out with the field isolate of TiLV (isolate 4/2011, passage 2), which was aliquoted and kept frozen at −80° C. Before use, the virus was thawed and cultured once more (passage 3). For artificial reproduction of the disease, $2.6×10^5$ $TCID_{50}$ was injected intraperitoneally (i.p.) (group 1) into each fish (30 to 35 grams). All experiments were carried out in triplicate with groups of 30 fish. To prevent waterborne infection, each group of fish was kept in a separate 100-liter aquarium. During the cohabitation trials (group 2), groups of 30 fish were kept in 200-liter aquariums that were divided into three compartments by water-permeable grids, which allowed water (but not fish) circulation throughout the aquarium; a control group was kept in the middle. The fish surviving primary i.p. infection were pooled and 3 weeks after were divided into two groups (each with 15 fish) and infected once again by i.p. injection. The control groups were injected with uninfected (naive) E-11 cultures.

When in vivo/ex vivo experiments were conducted, the brains of individual TiLV-injected fish were collected (5 to 7 days post-injection) and minced as above. The homogenates (500 µl) were incubated with confluent E-11 cultures. Upon CPE appearance, the supernatants were collected and injected (200 µl) i.p. into naive fish.

The health conditions of the fish were carefully monitored throughout the growing and experiment periods; external signs and mortality rates were monitored twice daily for a total of 21 days. The animal care, experimental handling, and safety regulations conformed to the guidelines established by the Committee on Laboratory Animal Care at the Israeli Veterinary Services and were conducted under permit 020_b5471_6, issued by the Israeli Committee for Animal Welfare.

Histological analysis: Tissue samples were collected from euthanized naturally infected fish by abdominal incision and were fixed in 10% neutral buffered formalin. The specimens were embedded in paraffin (Paraplast Plus; Diapath), cut by microtome (Reichert-Jung 2050) into serial 5 µm sections, stained with hematoxylin and eosin (H&E) 277 (Roberts et al. 2012), and examined under a light microscope (Leica DMRB). Images were acquired by a Nikon digital light system.

Statistical analysis: The results of the in vivo experiments were presented as percentages of the mean mortality rates from three (or two, in case of surviving fish) independent experiments. Each experiment included three experimental groups (three independent repeats) of 30 fish.

The experiments with the surviving fish were performed in duplicate (two independent repeats), in which each group was composed of 20 fish. Variability between the experiments (infection by direct intraperitoneal injection, infection by cohabitation, and control fish) was determined by chi square tests, in which a P value of greater than 0.05 was considered significant.

Culture deposition: TiLV (CNCM accession no. 1-4817) was deposited at the Collection Nationale de Cultures de Microorganismes (CNCM) at the Institut Pasteur, Paris, France.

Nucleotide sequence accession number: The GenBank accession number for the extended sequence of clone 7450 is KJ605629 (SEQ ID NO: 1).

Figure 1B:
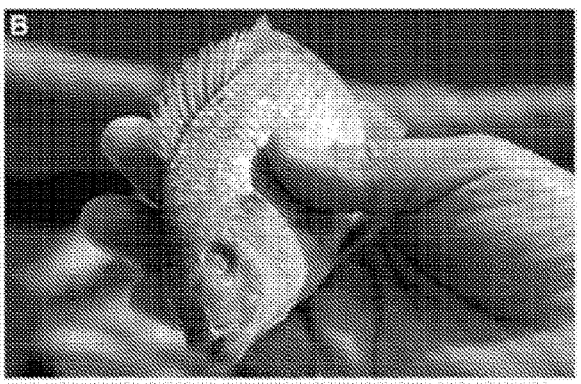
FIG. 1B is a photograph of a diseased tilapia demonstrating shrinkage of the eye and loss of ocular functioning (phthisis bulbi).

Example 2—Geographical Distribution and Characteristics of Diseased Tilapines from the Sea of Galilee and Commercial Ponds Disease outbreaks in wild and commercial tilapines were detected in the Sea of Galilee and in commercial ponds in Israel, located in the Northern coastal shore, Bet-Shean, Yizrael, the Jordan Valley, and Upper and Lower Galilee. In commercial ponds, this disease resulted in massive mortality (FIG. 1A). The sampling of fish from commercial catches at the Sea of Galilee revealed that all tilapine species are susceptible to the disease, although mass mortalities were not observed. In this case, the diseased fish presented with pronounced ocular lesions (FIG. 1B).

Figure 1C:
FIG. 1C shows the gross pathology of skin includes multifocal to coalescing dermal erosions and ulcers denoted by arrows.
Figure 1D:
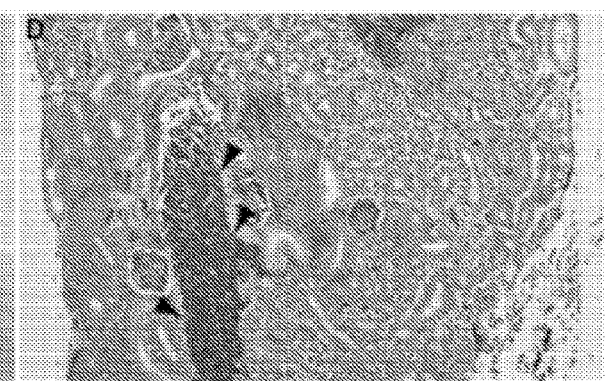
FIG. 1D shows hematoxylin and eosin stain of kidney and interstitium. The arrows mark a dilated vein packed with large numbers of red blood cells (congestion). Hematoxylin and eosin (H&E) stain×10.

Pathological findings included gross lesions characterized mainly by ocular alterations, including opacity of the lens (cataract). In advanced cases, the lesions included ruptured lenses with phacoclastic induced uveitis or endophthalmitis accompanied by the formation of a cyclitic membrane, followed by swelling of the eyeball (buphthalmia), loss of globe integrity with occasional perforated cornea and poring of inspissated content or shrinkage, and loss of ocular functioning (phthisis bulbi) (FIG. 1B). Other lesions included skin erosions (observed in diseased pond-raised tilapines; FIG. 1C), hemorrhages in the leptomeninges, and moderate congestion of the spleen and kidney (FIG. 1D).

The histologic lesions of the brain included edema, focal hemorrhages in the leptomeninges, and capillary congestion in both the white and gray matter (FIG. 1E). Foci of gliosis and occasional perivascular cuffs of lymphocytes were detected (FIG. 1F). Some neurons within the telencephalon and particularly in the optic lobes displayed various levels of neuronal degeneration, including cytoplasmic rarefaction and vacuolation and peripherally displaced nuclei (central chromatolysis).

Ocular lesions included an undulated, thin, and frequently coiled and ruptured lenticular capsule, surrounded by circular fibroplasia and fibrosis with multiple synechiae to the iris and ciliary body (posterior synechia) and moderate numbers of eosinophilic granulocytic cells and melano-macrophage centers or MMCs. The infiltrate extended into the anterior chamber, iris, vitreous humor, and choroid (endophthalmitis). There were cataractous changes within the lens characterized by eosinophilic homogenous spherical structures (morgagnian globules), markedly enlarged lens epithelial cells with abundant eosinophilic microvacuolated cytoplasm (bladder cells), large lakes of proteinaceous fluid (liquefied lens fibers), mineralization, and flattened elongated cells (fibrous metaplasia) (FIG. 1Ga, compared to normal lens in FIG. 1Gb). The squamous epithelium of the cornea was frequently eroded and ulcerated and infiltrated by moderate numbers of lymphocytes, macrophages, and eosinophilic granulocytic cells, and it was underlined by stromal neovascularization and edema (FIG. 1H).

The hepatic parenchyma displayed occasional randomly distributed foci of hepatocellular swelling and clearing, with cytoplasmic accumulation of granular yellow to brown pigment. The spleen was hyperplastic, with proliferating lymphocytes surrounding the ellipsoids. MMCs were increased in size and number in both the liver and the spleen. MMCs are distinctive clusters of pigment-laden cells, commonly seen within the reticuloendothelial supporting matrix of hematopoietic tissues. MMC proliferation is associated with late stages of chronic infection as a response to severe tissue injury in a variety of infections (especially viruses) or poor environmental conditions. Therefore, they are considered indicators of fish population health (Agius and Roberts 2003).

Example 3—Isolation of the Etiological Agent from Infected Specimens

To culture potential pathogens from diseased tilapines, the organs of fish with the characteristics described above were pooled, homogenized, and incubated with eight different cell lines as described in Example 1. No known pathogen was identified, and only the established E-11 cell line and the primary tilapia brain cells consistently showed CPE upon incubation with the above-mentioned homogenates. In E-11 cells, CPE became visible 5 to 7 days postinoculation, with the appearance of cytoplasmic vacuoles and plaque formation (FIG. 2A), which rapidly progressed to an almost-complete disintegration of the cell monolayer (at 9 to 10 days postinoculation). The CPE in primary tilapia brain cells was characterized by conversion of the typical elongated cells into swollen, rounded, and granulated cells, which were clearly observed at 10 to 12 days postinoculation (FIG. 2B), leading to vast monolayer detachment (days 14 to 19) but without plaque formation. The control mock-infected E-11 and primary tilapia brain cultures did not show any CPE (FIGS. 2C and 2D, respectively). Similar results were obtained when the supernatants of the cultures with CPE were used to inoculate naive cultures (tested for up to 18 passages) and when the supernatants, or the above-mentioned homogenates, were filtered through 0.22 □m filters. In addition, the number of plaques induced by the agent was directly related to its dilution, yielding a one-hit curve. A single infectious unit was therefore sufficient to produce a plaque. These results indicated that the described CPE was due to the presence of an infectious agent, likely a virus. The CPE-causing agent was recovered from 25 samples, collected from all Israeli regions where fish were cultured.

Example 4—Morphological Features of Virus-Like Particles

Further support for viral infection in E-11 cultures showing CPE came from EM examination of thin sections of these cells as described in Example 1. This analysis revealed the presence of sparse electron-dense particles (diameter, 55 to 75 nm), enclosed in the intracytoplasmic membrane (FIG. 2E) or within the cytoplasm (FIG. 2F). No such particles were found in the healthy control cell cultures. Of note, these particles do not originate from the snakehead retrovirus (SnRV) that is expressed in E-11, since assemblies of this C-type retrovirus are larger and are generated only at the plasma membrane; moreover, SnRV nascent virions were not visualized by EM in this specific cell line (although SnRV sequences could be amplified by PCR).

Pellets, purified from the supernatants of infected E-11 cultures by ultracentrifugation through 25% sucrose cushions, were negatively stained and examined by EM. This analysis revealed virion-like structures (approximately 75 to 80 nm) surrounded by a readily detected thick coat (FIG. 2G). Such virions were abundant and were not detected in the control pellets prepared from naive E-11 cells.

Example 5—Sensitivity of the Infectious Agent to Ether or Chloroform

The EM analyses from Example 4 indicated that the infectious agent, isolated from diseased tilapia, is an enveloped virus. To test this, virions in the supernatants of E-11-infected cells were exposed to either ether or chloroform and the effect of these treatments on infectivity was measured as described in Example 1.

Table 1 summarizes the results of two and three repeats of the ether and chloroform sensitivity assays, respectively. A reduction in the infectivity of approximately three (chloroform) to five (ether) orders of magnitude was observed, demonstrating the sensitivity of the agent to these solvents. This indicated that the infectious agent is indeed enveloped by a lipid membrane.

TABLE 1

Ether and chloroform sensitivity assays

| Treatment | Expt no. | $TCID_{50}/ml$ without treatment | $TCID_{50}/ml$ plus treatment | Fold reduction | Average fold reduction |
|---|---|---|---|---|---|
| Ether | 1 | $10^{4.49}$ | $10^{-1}$ | $10^{5.49}$ | $1.58 \times 10^5$ |
|  | 1 | $10^{4.83}$ | 10 | $10^{3.83}$ |  |
| Chloroform | 1 | $10^{4.63}$ | $10^{1.5}$ | $10^{3.13}$ | $0.93 \times 10^3$ |
|  | 2 | $10^{3.5}$ | $10^{1.5}$ | $10^{2}$ |  |
|  | 3 | $10^{4.63}$ | $10^{1.5}$ | $10^{3.13}$ |  |

Example 6—Initial Molecular Characterization of Tilapine Virus

Having demonstrated that an infectious agent can be isolated from diseased fish and can be propagated in specific cell culture (Examples 3), this disease-causing agent was named tilapia lake virus (TiLV), as a reference to the site from which it was initially isolated.

To purify TiLV, TiLV-infected culture supernatants were fractionated through velocity sucrose step gradients ranging from 10 to 70% sucrose. The CPE-inducing activity was mainly localized to the 30 to 40% sucrose fractions.

To further identify TiLV-specific sequences, RNA was extracted from TiLV virions (purified by ultracentrifugation through sucrose cushions) and used as a template in a reverse transcription reaction. The fragments of the resulting cDNA were cloned using a shotgun approach as described in Example 1. This approach allows the cloning of cDNAs that are present at small amounts, without prior knowledge of their sequences. One of these fragments (clone 7450) was subjected to 5' and 3' RACE reactions, resulting in the identification of 1,326 bases of a TiLV sequence (SEQ ID NO: 1) (GenBank accession no. KJ605629), which contained an open reading frame (ORF) of 420 amino acids (SEQ ID NO: 12). SEQ ID NO: 1 was later identified to be part of SEQ ID NO: 9.

No significant homologies were found in both the nucleic acids and protein sequences of this clone using BLAST searches (Altschul et al 1997; Johnson et al. 2008) in the GenBank databases.

Example 7—PCR for TiLV Detection

Figure 3A:
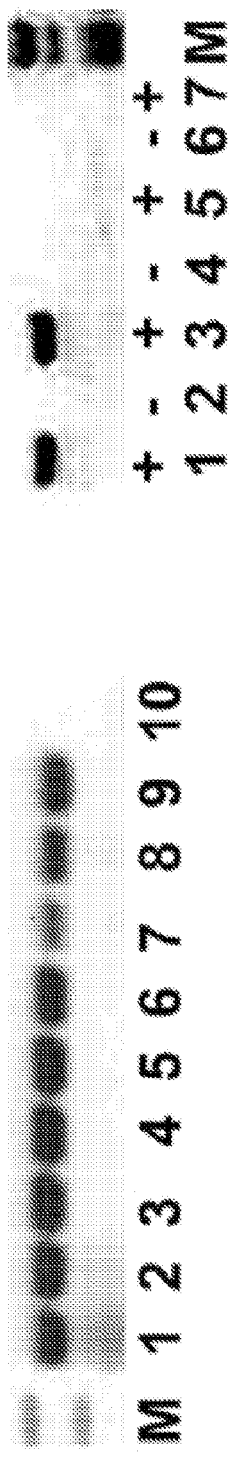
FIG. 3A show the detection of TiLV by PCR. Total RNA was extracted from brains of TiLV infected fish (lanes 1 to 7) and a healthy fish (lane 10), as well as from E-11 and primary tilapia brain infected cell cultures (lanes 8 and 9, respectively), and was used as a template for cDNA generation. A 250-bp fragment was amplified with ME1 (SEQ ID NO: 23) and clone 7450/150R (SEQ ID NO: 16) primers.

As described in Example 1, PCR was performed to detect TiLV. To establish a PCR assay for detecting TiLV, total RNA was extracted from the brains, kidneys, hearts, livers, and spleens of moribund fish. In addition, RNA was extracted from TiLV-infected primary tilapia brain or E-11 cultures and was used as a template for cDNA generation. These samples were subject to RT-PCR with primers that were derived from clone 7450 (SEQ ID NO: 1). A 250-bp fragment was amplified with ME1 (GTTGGGCACAAGG-CATCCTA) (SEQ ID NO: 23) and clone 7450/150R (TAT-CACGTGCGTACTCGTTCAGT) (SEQ ID NO: 16) primers. The PCR assays resulted in the amplification of the expected 250-bp fragment from the brains of TiLV-infected fish (FIG. 3A).

Figure 3B:
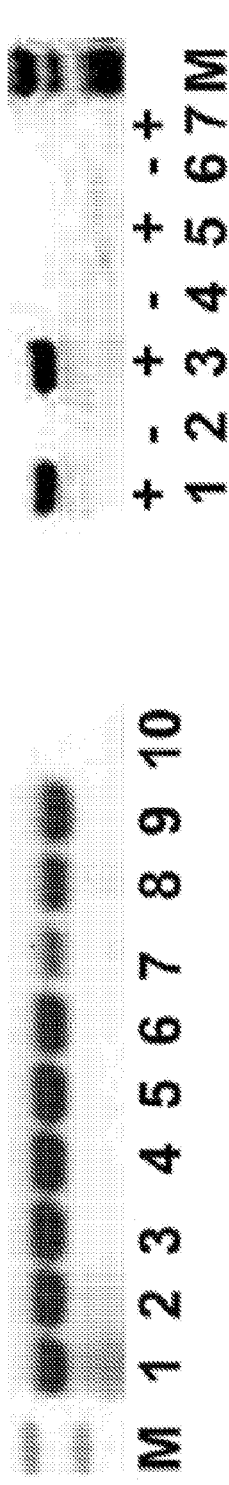
FIG. 3B shows that reverse transcription was required for PCR amplification of TiLV. Total RNA was extracted from the supernatant (lanes 1 and 2) or from cell extracts (lanes 3 and 4) of TiLV-infected E-11 culture, or from naive E-11 culture (lanes 5 and 6). The samples were not treated with DNase, and reverse transcription was carried out (+) or not (−) prior to the PCR step. A "no RNA" negative control (lane 7) was also included. A 491-bp fragment was amplified with the primers Nested ext-1 (SEQ ID NO: 24) and Nested ext-2 (SEQ ID NO: 25).

The amplification of TiLV was achieved only after a reverse transcription step, even under conditions in which the samples were not treated with DNase (FIG. 3B). Total RNA was extracted from the supernatant or from cell extracts of TiLV-infected E-11 culture, or from naive E-11 culture. The samples were not treated with DNase, and reverse transcription was carried out (+) or not (−) prior to the PCR step. A "no RNA" negative control (lane 7) was also included. A 491-bp fragment was amplified with the primers Nested ext-1 (TATGCAGTACTTTCCCTGCC) (SEQ ID NO: 25) and Nested ext-2 (TTGCTCTGAGCAAGAGTACC) (SEQ ID NO: 26), only when reverse transcriptase was carried out. This is highly indicative of an RNA genome for TiLV. Consistent amplification in the samples of brain tissues was observed compared to the other organs. Amplification was also observed in TiLV-infected primary tilapia brain and E-11 cultures but not in a negative control that included cDNA prepared from the brain of a healthy (naive) fish (FIG. 3B).

No amplification was observed in additional negative controls, which included mock-infected primary tilapia brain and E-11 cultures, or E-11 cultures infected with the viral nervous necrosis (VNN) betanodavirus. Of note, the absence of amplification in the sample of VNN-infected cells further indicates that clone 7450 represents a sequence derived from TiLV rather than a fish gene that is upregulated upon infection. In all cases, sequencing of the amplified fragments revealed full identity with the expected sequence.

The above PCR assay was also exploited to further test the RNA nature of the TiLV genome. For this, the virions in the supernatants of TiLV-infected E-11 cultures were exposed to DNase I and RNaseA to digest nucleic acids that are not protected by virions. The particles were then pelleted through sucrose cushions and digested with proteinase K, and the protected deproteinized nucleic acids were purified. These nucleic acids were exposed to RNase I, an enzyme with a preference for single-stranded RNA. The resulting products were reverse transcribed or not, and subjected to PCR amplification using TiLV-specific primers. (Nested ext-1 [TATGCAGTACTTTCCCTGCC] (SEQ ID NO: 25) and Nested ext-2 [TTGCTCTGAGCAAGAGTACC] (SEQ ID NO: 26); or SnRV-specific primers (Snakehead gag-pol fw [CAGATCACTGATCGATGC] (SEQ ID NO: 27) and Snakehead gag-pol rev [GTCTGAAAGGTAAGGTGG] (SEQ ID NO: 28).

Figure 3C:
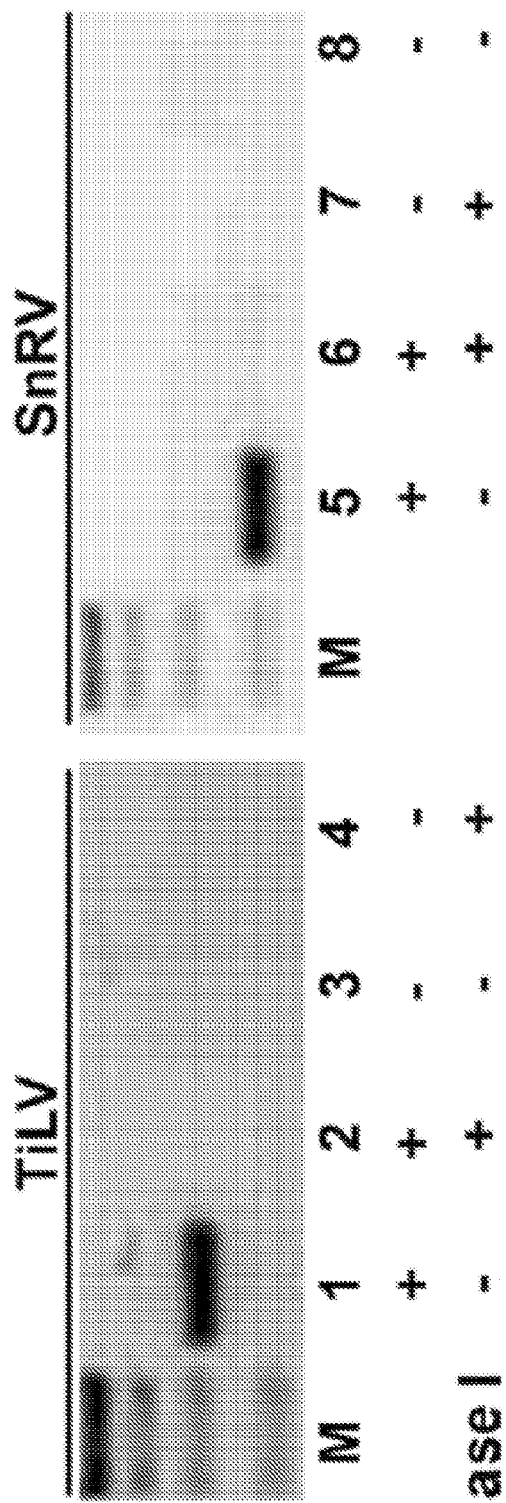
FIG. 3C shows the results of nuclease sensitivity assays. Nuclease-protected nucleic acids were extracted from purified virions and were treated (+) or not (−) with reverse transcriptase and/or RNase I prior to PCR amplification with TiLV-specific primers (Nested ext-1 (SEQ ID NO: 24) and Nested ext-2 (SEQ ID NO: 25) resulting in amplified product, 491 bp) or SnRV-specific primers (Snakehead gag-pol fw (SEQ ID NO: 26) and Snakehead gag-pol rev (SEQ ID NO: 27), resulting in amplified product, 284 bp). M is the DNA size marker.

The amplification of TiLV sequences was observed only after a reverse transcription step (FIG. 3C, lanes 1 and 3, similar to the result in FIG. 3B), and only if RNase I was avoided (FIG. 3C, lanes 1 and 2). The single-stranded genomic RNA of SnRV, which was copurified along the TiLV genome, was used as an internal positive control for this assay (FIG. 3C, lanes 5 to 8). These results further indicated that the TiLV genome, encapsidated in the virion, is composed of RNA in single stranded form.

Example 8—Reproduction of Tilapine Disease by Intraperitoneal Injection

Figure 4:
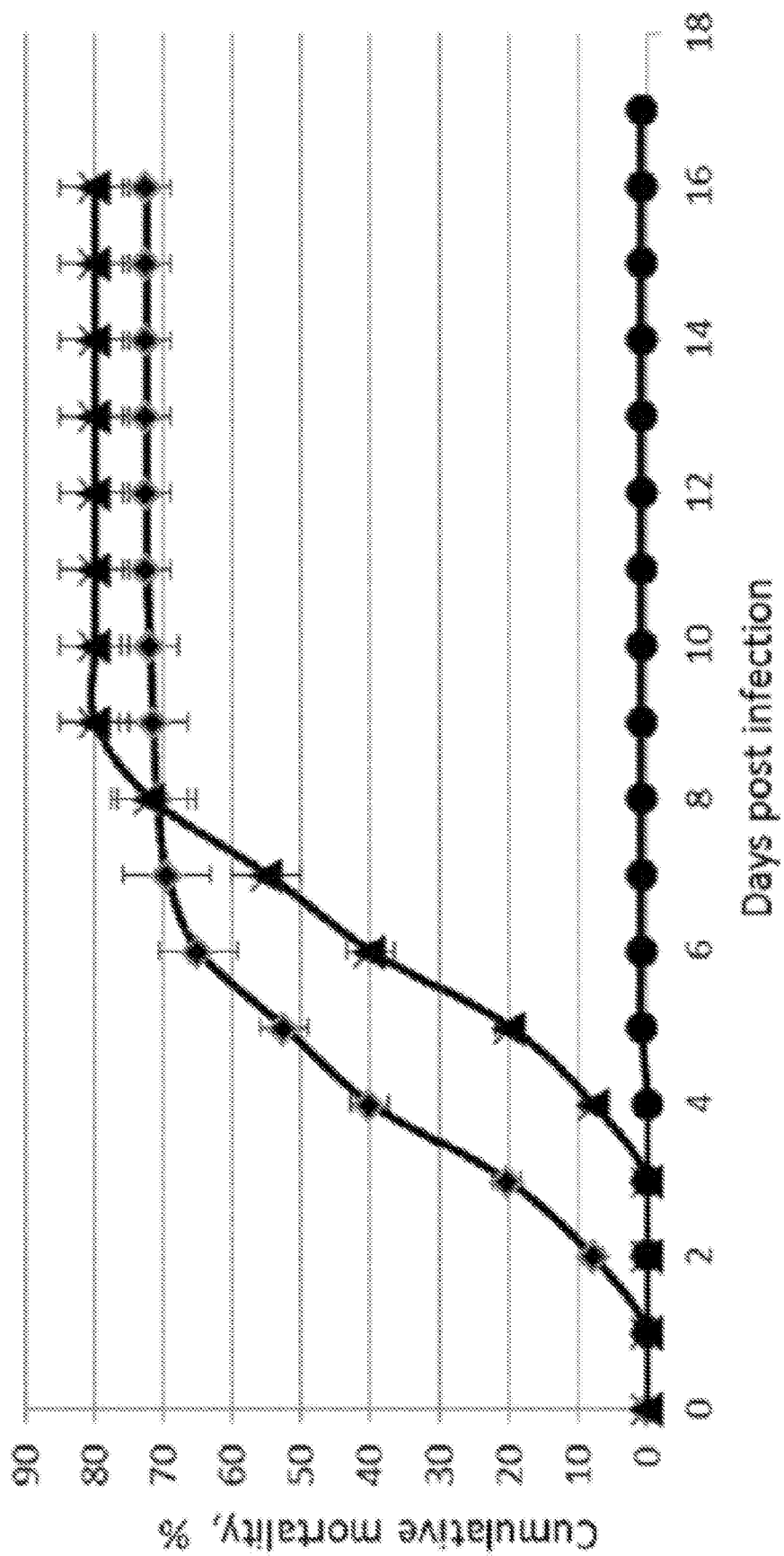
FIG. 4 shows kinetics of TiLV-induced mortality. Fish were divided into groups of 30 specific pathogen-free (SPF) fish. Groups 1 (solid diamond) and 2 (solid triangle) were infected by intraperitoneally (i.p.) injection or cohabitation, respectively. The control group (solid circle) was composed of an identical number of fish inoculated with the supernatants of naive E-11 cultures. Variability between the three experimental groups was determined by chi-square tests, in which a P value of 0.05 was considered significant. Bars represent standard errors.

To test if TiLV can cause disease in tilapines, the supernatants from naive or TiLV-infected E-11 or primary tilapia brain cultures were filtered (0.22 □m), and 200 □l was injected i.p. into naive *Tilapia nilotica* (groups of 30 fish as described in Example 1). All of the naive fish that were inoculated with the control supernatants (of naive E-11 cultures) remained asymptomatic. However, 74 to 85% of the fish that were injected with the supernatants of TiLV-infected E-11 or TiLV-infected primary tilapia brain cultures developed clinical disease (lethargy, discoloration, ocular alterations, skin patches, and ulcerations) and died within 10 days (FIG. 4). The same mortality rate was also observed for fish injected with TiLV that was purified by endpoint dilution assay (TiLVx2). Furthermore, the brains from experimentally infected fish were harvested and co-incubated with naive E-11 cells. Such cultures developed a characteristic CPE. The supernatants of these cultures were then harvested and injected into naive fish, resulting in the appearance of the disease in fish. Overall, this in vivo/ex vivo passage experiment was serially repeated three times, with a consistent mortality rate of 75 to 85% in each round within 10 days post-injection.

This clearly confirmed that TiLV, isolated from infected fish and propagated in E-11 cells, was indeed the etiologic agent of the disease. Importantly, fish that survived the experimentally induced disease (35 fish) were completely immune to disease development upon a challenge consisting of a second i.p. injection (3 to 4 weeks after the first injection). This indicates that fish can mount a protective immune response to TiLV.

Example 9—Reproduction of Tilapine Disease by Cohabitation

To determine if TiLV is transmissible in a setting resembling natural conditions, a cohabitation experiment was performed in which naive fish were cohabitated with fish experimentally infected with TiLV as described in Example 1.

These experiments clearly demonstrated that the naïve fish developed a lethal disease, with a mortality rate similar to the one obtained by the i.p. route but with slower kinetics (2 to 3 days delay in reaching 50% mortality, $P<0.05$ (FIG. 4)). These experiments provide proof of the ability of TiLV to spread through a waterborne route.

Example 10—Bioinformatic Data Analysis

Ion Torrent data were generated using as a template brain RNA of sick tilapia after depletion of ribosomal RNA (two libraries). Illumina data were generated for nuclease treated and sucrose gradient purified particles obtained from infected E11 culture cells (two libraries). Ion Torrent libraries were preprocessed with cutadapt (Martin 2011) to remove low quality ends, trimmed to 150 bp maximum length, and stripped of adapter sequences.

Reads from all four libraries (2 brain and 2 cell culture) were taxonomically classified using taxMaps by mapping against the National Center for Biotechnology Information's (NCBI) nt database, the NCBI RefSeq database (Pruitt et al. 2012), the tilapia reference genome sequence (Oreni11.1) and corresponding annotated tilapine mRNA sequences (Brawand et al. 2014). Unclassified reads (not mapping to any known sequence) were then independently assembled using the VICUNA assembler (Yang et al. 2012). Contigs from each library were aligned with BLAST (Camacho et al. 2009) against all contigs from the other 3 libraries, retaining hits with an e-value of 1e-10 or lower. Single linkage clustering was used to group together all the contigs that showed any similarity. On the assumption that the infectious agent should be present in all 4 libraries, 10 contig clusters were identified that contained at least one contig from each of the 4 libraries.

Within each cluster, contigs were aligned to each other and manually assembled to generate maximum length sequence after inverted tandem duplications at the ends of contigs, likely resulting from amplification artifacts, were removed. Overlapping predicted ORFs in contigs from different assemblies were used to correct for frameshift errors (mostly occurring due to indels in the Ion Torrent reads) and to infer the longest possible ORF.

Based on a model wherein the genomic segments are anticipated to contain conserved termini, a combination of k-mer analysis, read depth analysis, and manual curation was used to build 5' and 3' terminal sequence motifs to refine terminal sequences. Mapping of the 10 final consensus sequences against the initial raw read data with BWA-MEM (Li 2013) demonstrated that 99% of the unidentified reads from the Illumina libraries and 87% of unidentified reads from the Ion Torrent libraries mapped to the consensus sequences.

Example 11—Complete Characterization of TiLV Genome

Based on the bioinformatics consensus sequences PCR primers were designed and contiguous sequences of all 10 clusters amplified from infected Tilapia specimens. Terminal sequences of each of the genome segments were revised by 5'- and 3'-Rapid Amplification of cDNA Ends (RACE) (Table 2). Analogous analyses by high throughput sequencing and PCR amplification was performed on samples from diseased Tilapia from Israel, and then performed on samples from Tilapia with a similar disease syndrome from Ecuador. Sequences for all 10 segments were obtained that showed a greater than 94% nucleotide sequence identity to the corresponding sequences from Israeli Tilapia.

Fragments of each segment were cloned into plasmid vectors to generate probes for Northern blotting. Three mixes of probes were used representing segments 1, 4, 7, and 10 (Combo 1); 3, 6, and 9 (Combo 2); or 2, 5, and 8 (Combo 3) to prevent signal overlap from similar sized segments. Total RNA was extracted from the livers of diseased Ecuadorian tilapia and from the culture cells infected with brain derived TiLV from Israeli tilapia or cell culture supernatant. Northern blot demonstrated the presence of all 10 sequences in nucleic acid extracts from infected Israeli and Ecuadorian Tilapia (FIG. 5).

Homology searches in the NCBI sequence database yielded only a single hit for segment 1 that indicated very distant homology to orthomyxoviral RNA-dependent RNA polymerase motifs (Table 2).

TABLE 2

TiLV genome segments

| Segment | Cluster # | Size [nt] | Homology to known sequences | SEQ ID NO |
|---|---|---|---|---|
| 1 | 5 | 1640 | orthomyxoviral PB1 polymerase domains | 7 |
| 2 | 0 | 1471 | none | 2 |
| 3 | 7 | 1371 | none | 9 |
| 4 | 4 | 1249 | none | 6 |
| 5 | 1 | 1098 | none | 3 |
| 6 | 2 | 1044 | none | 4 |
| 7 | 3 | 777 | none | 5 |
| 8 | 9 | 657 | none | 11 |
| 9 | 8 | 549 | none | 10 |
| 10 | 6 | 465 | none | 8 |

Example 12—Diagnostic PCR

Figure 6:
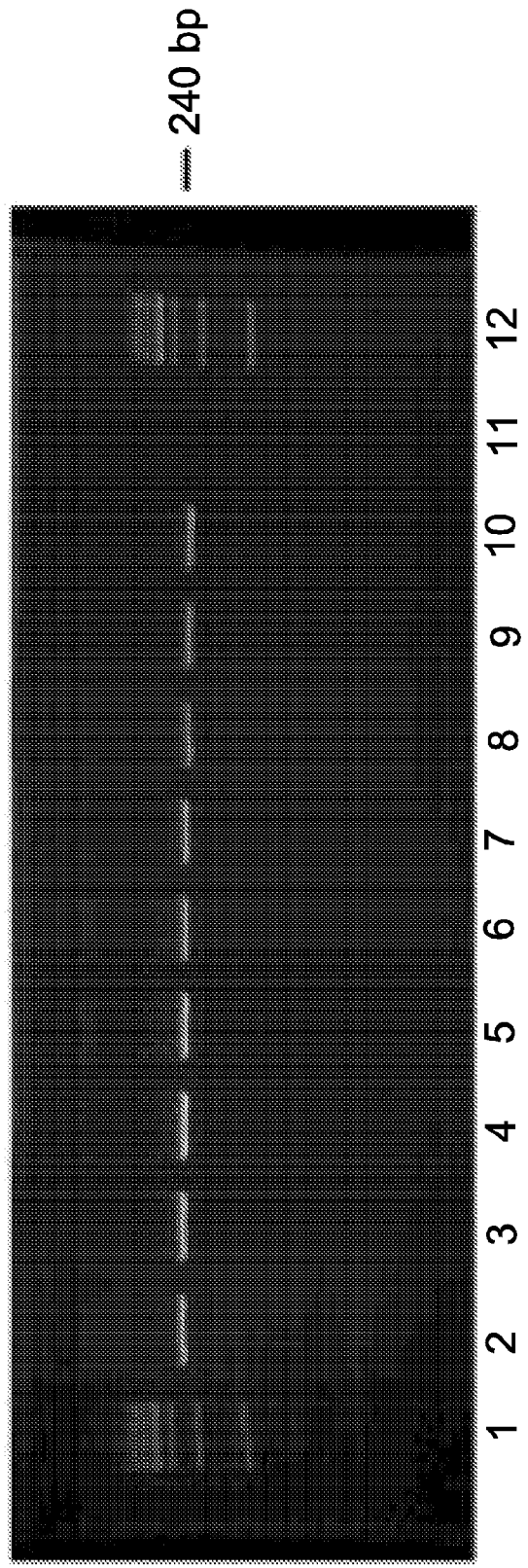
FIG. 6 shows the results of conventional diagnostic PCR using primers designed to amplify segment 3 of the TiLV genome. The figure is an image of an agarose gel electrophoresis of amplification products obtained from nucleic acid extracts of TiLV-infected cell culture supernatant. Lane 1 and 12 are size markers. Lanes 2-10 are serial 2-fold dilutions of nucleic acid extract. Lane 11 is a negative control of non-infected cell culture supernatant.

Conventional PCR: Primers NM-CLU7-SF1, 5'-AGT TGC TTC TCA YAA GCC TGC TA (SEQ ID NO: 28) and NM-CLU7-SR1, 5'-TCG TGT TCA CAR CCA GGT TTA CTT (SEQ ID NO: 29) were designed to amplify an approximately 245-nt region of TiLV segment 3 (cluster 7, Accession no. KJ605629). cDNA from TRI-reagent (Invitrogen) extracted RNA was synthesized with Superscript III (Life Technologies) and random hexamers according to vendor's protocol. PCR was performed with Amplitaq Gold (Life Technologies) and PCR products visualized on agarose gels, purified with Purelink Gel Extraction kit (Invitrogen), and confirmed for target specificity by Sanger sequencing on both strands (GeneWiz, NJ). (FIG. 6)

Figure 7A:
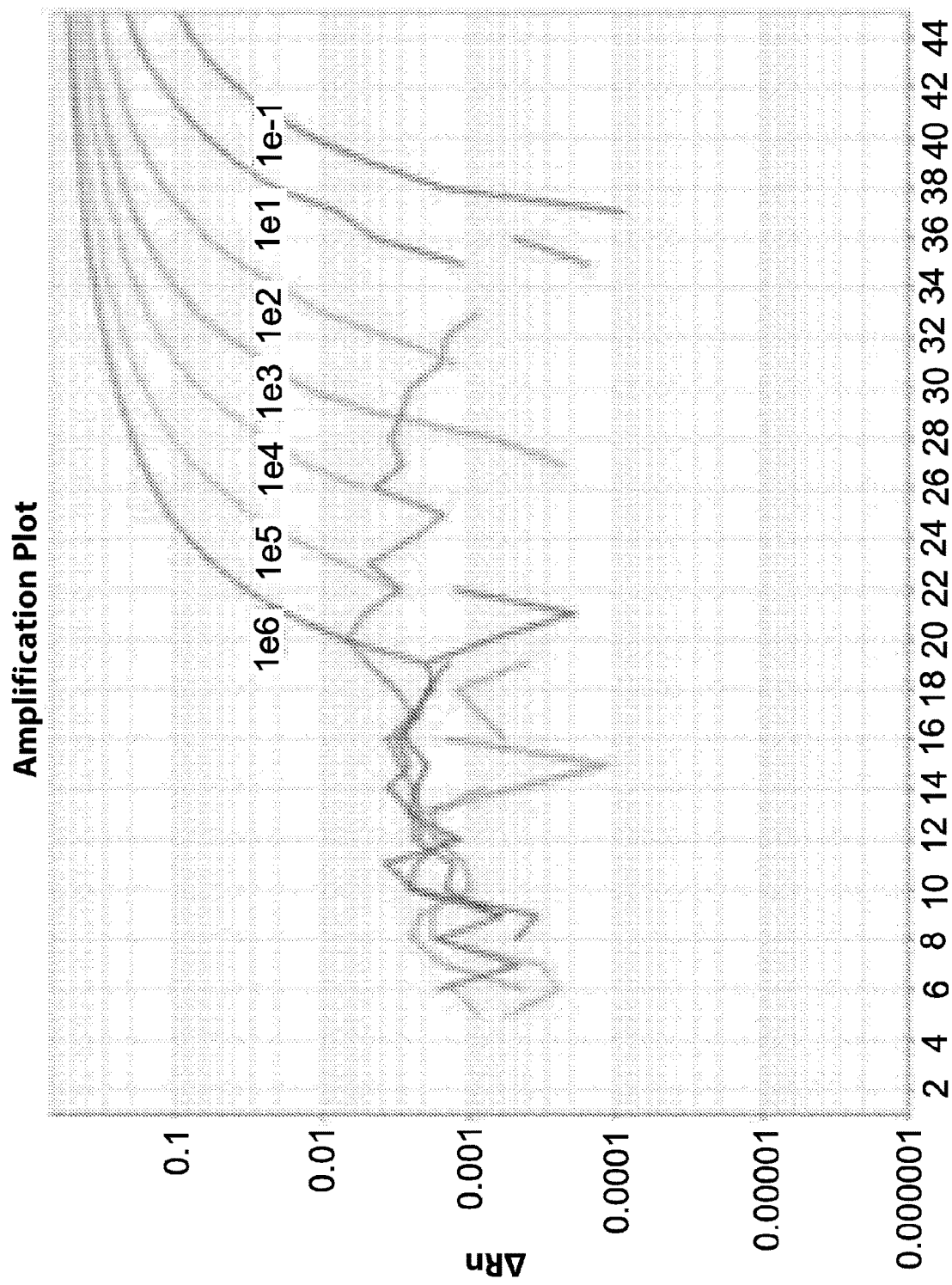
FIG. 7A is a calibration curve using quantitated plasmid standards representing TiLV segment 1 target sequence, ranging from $1 \times 10^6$ to $1 \times 10^1$ molecules per assay.
Figure 7A:
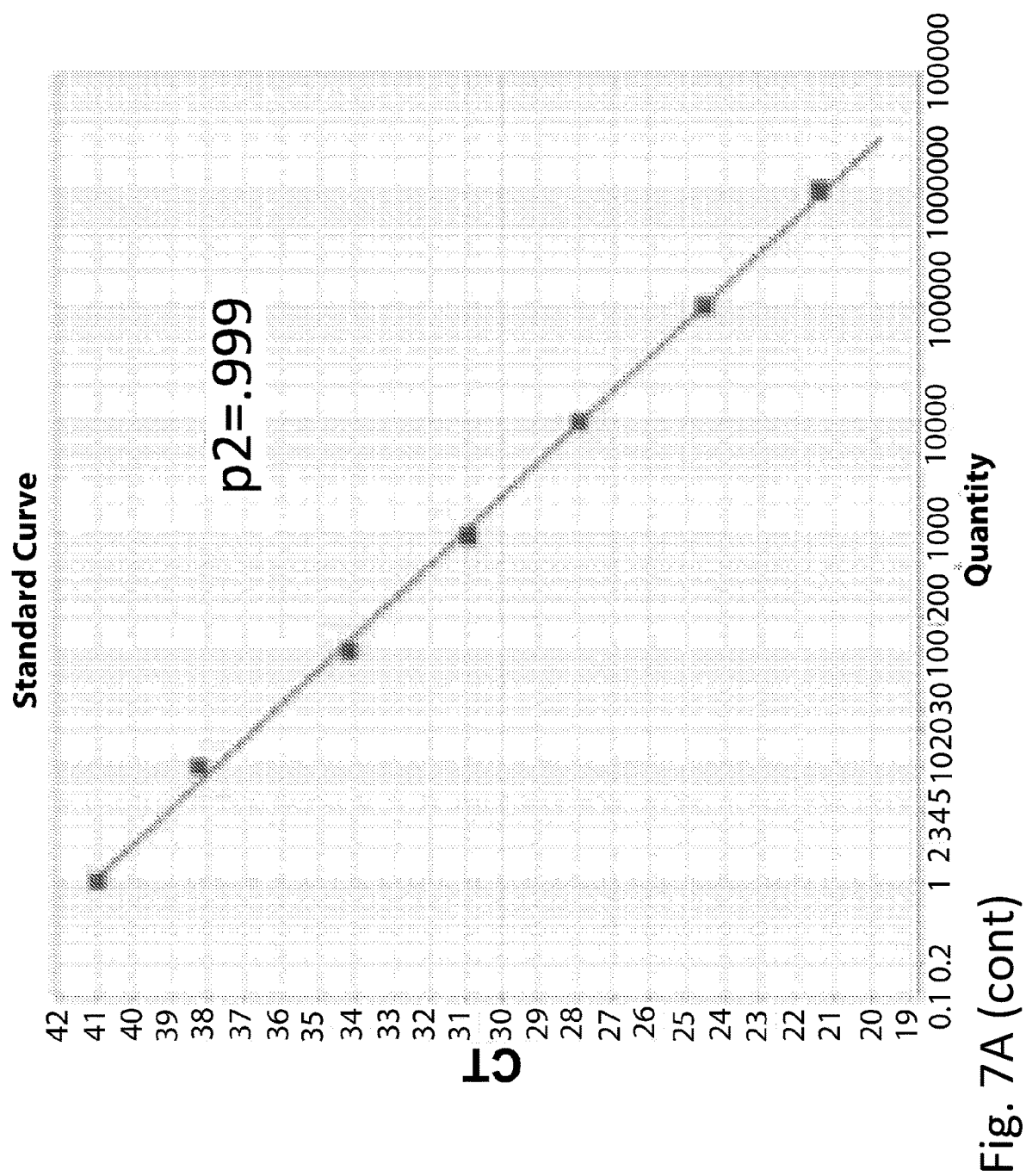
Figure 7B:
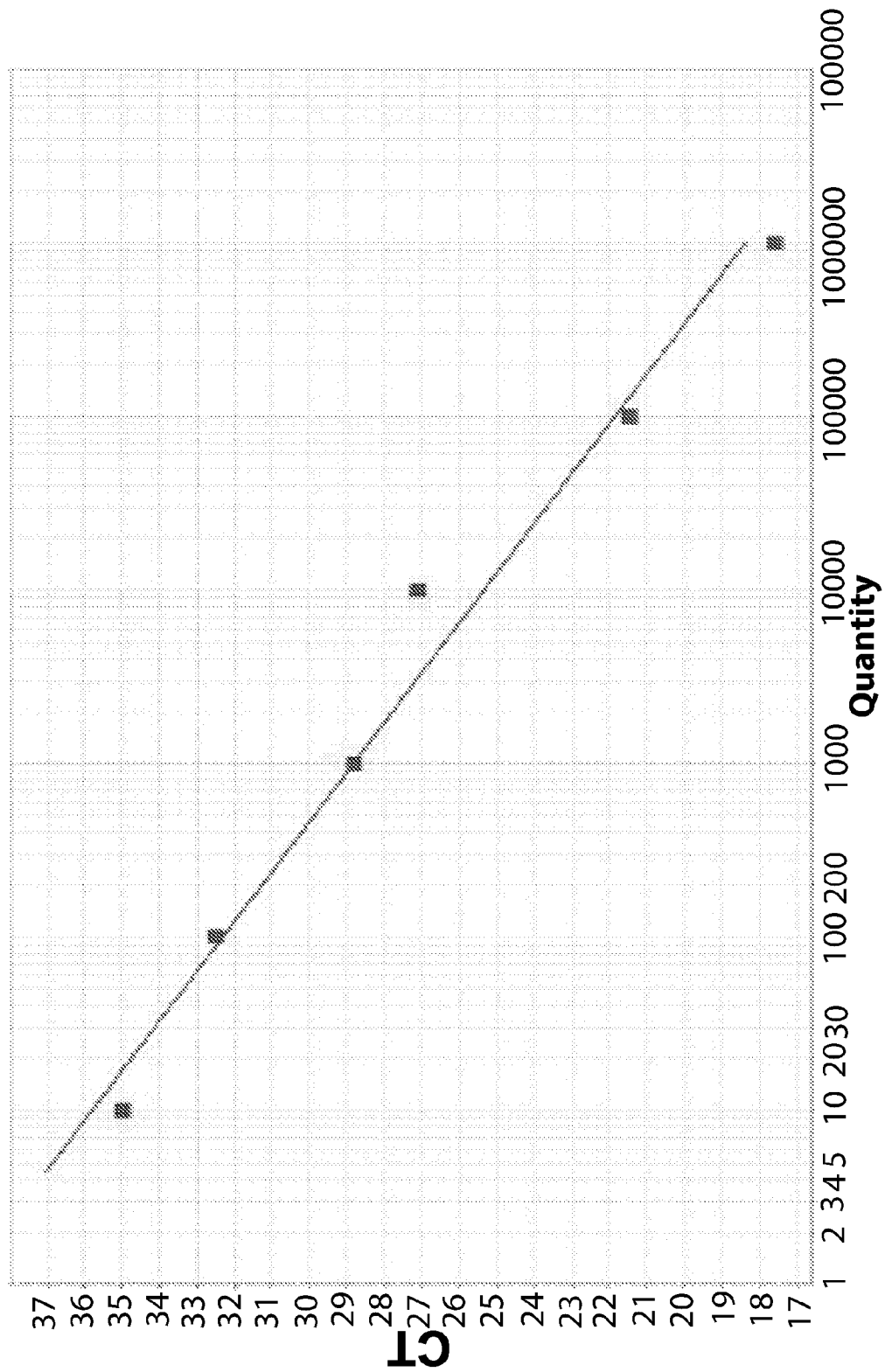
FIG. 7B is a calibration curve using quantitated plasmid standards representing tilapia beta-actin target sequence, ranging from $1 \times 10^6$ to $1 \times 10^1$ molecules per assay.

Quantitative real-time PCR: A quantitative real-time PCR assay for TiLV was established targeting TiLV segment 1 and beta-actin as a house-keeping gene control (Oreochromis niloticus beta-actin mRNA, XM_003443127) (FIG. 7). For both assays the respective target regions were cloned into plasmid vectors using primers TiLV-CLU5-cF1, 5'-GGT CAA TTC GAG TCA TGC TCG (SEQ ID NO: 30)/TiLV-CLU5-cR1, 5'-GCT GGA CTG CTT TAT AAA TAG CAT AG (SEQ ID NO: 31), or TIL-Actin-cF1, 5'-ATC CTG CGT CTG GAC CTG GCT (SEQ ID NO: 32)/TIL-Actin-cR1, 5'-TGC CAA TGG TGA TGA CCT GTC (SEQ ID NO: 33) to generate quantitative calibration standards (FIGS. 7A and 7B).

Targeted real-time PCR were performed using the following specific oligonucleotides:
TiLV Segment 1 (Cluster 5)
CLU5-mRNA-qF1, 5'-AGC TAT GTT ATC TGG CGC T (SEQ ID NO: 34)
CLU5-mRNA-qR1, 5'-GTT GTT ATA CCT ATA GGC ACA T (SEQ ID NO: 35)
CLU5-mRNA-Probe, FAM-5'-GCC ATT CCA CTC AGC AGA ACG TCT G-TAMRA (SEQ ID NO: 36)
Tilapia Beta-Actin
TIL-Actin-qF1, 5'-GCG TGA CAT CAA RGA GAA GCT G (SEQ ID NO: 37)
TIL-Actin-qR1, 5'-CCA ATG GTG ATG ACC TGT C (SEQ ID NO: 38)
TIL-Actin-Probe, FAM-5'-CCC TGG AGA AGA GTT ACG AGC TGC-TAMRA (SEQ ID NO: 39)

Figure 7C:
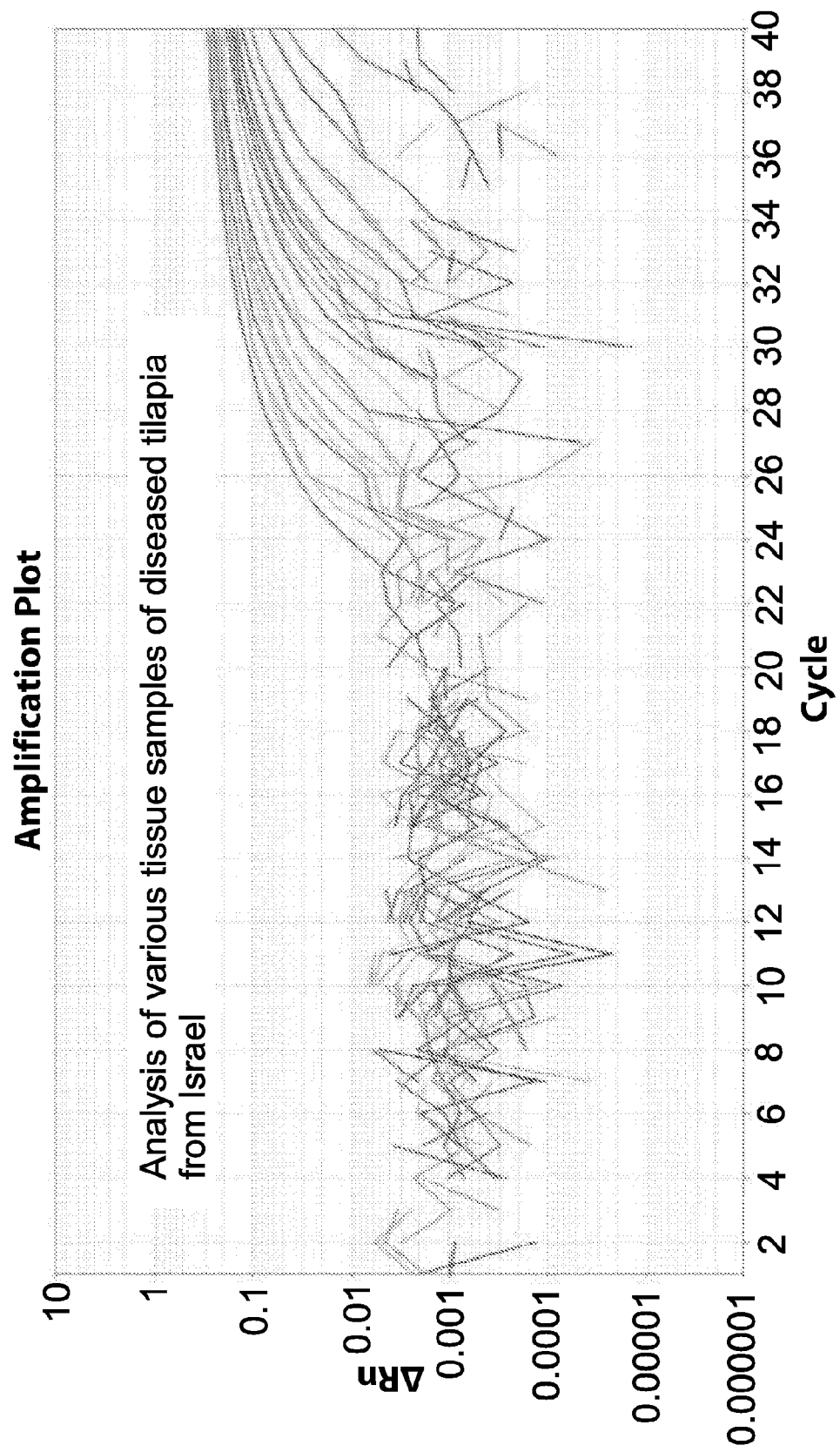
FIG. 7C shows the detection of authentic TiLV in various tissue specimens of diseased tilapia from Israel using primers designed from and specific for TiLV nucleic acid sequences.

As shown in FIG. 7C, detection of authentic TiLV was found in various tissue samples of diseased tilapia from Israel using real-time PCR with primers specific for TiLV.

REFERENCES

Agius and Roberts 2003. *J. Fish Dis.* 26:499-509.
Altschul et al. 1997. *Nucleic Acids Res.* 25:3389-3402.
Bacharach et al. 2000. *J. Virol.* 74:11027-11039.
Bigarré et al. 2010. *J. Fish Dis.* 32:667-673.
Brawand et al. 2014. *Nature* 513:375-81.
Camacho et al. 2009. *BMC Bioinformatics* 10:421.
Crandell et al. 1975. *J. Clin. Microbiol.* 2:465-468.
Food and Agriculture Organization of the United Nations (FAO). 2010. Cultured aquatic species information programme, *Oreochromis niloticus* (Linnaeus, 1758). Food and Agriculture Organization of the United Nations, Rome, Italy.
Food and Agriculture Organization of the United Nations (FAO). 2010. Fisheries and Aquaculture Department. Species fact sheets: *Oreochromis niloticus* (Linnaeus, 1758). Food and Agriculture Organization of the United Nations, Rome, Italy.
Hasegawa et al. 1997. *Fish Pathol.* 32:127-128.
Hedrick et al. 2000. *J. Aquat. Anim. Health* 12:44-57.
Hutoran et al. 2005. *J. Virol.* 79:1983-1991.
Johnson et al. 2008. *Nucleic Acids Res.* 36(Suppl 2):W5-W9.
Laham and Bacharach 2007 *J. Virol.* 81:10687-10698.
Li 2013. arXiv:1303.3997.
Martin 2011 *EMBnet.journal* 17:10-12.

Melamed et al. 2004. *J. Virol.* 78:9675-9688.
Nehls and Boehm 1995. *Trends Genet.* 11:39-40.
Oberpichler et al. 2008. *Environ. Microbiol.* 10:2020-2029.
Pruitt et al. 2012 *Nucleic Acids Res.* 40:D130-D135.
Reed and Muench 1938. *Am. J. Hyg.* 27:493-497.
Reynolds 1963. *J. Cell. Biol.* 17:208-212.

Roberts et al. 2012 *Laboratory Methods in Fish Pathology*, Fourth Edition, John Wiley & Sons, Inc.
Scotto-Lavino et al. 2006a. *Nat. Protoc.* 1:2742-2745.
Scotto-Lavino et al. 2006b. *Nat. Protoc.* 1:2555-2562.
Shlapobersky et al. 2010. *Virology* 399:239-247.
Yang et al. 2012. *BMC Genomics* 13:475.

The invention claimed is:

1. An engineered nucleic acid expression construct capable of driving expression of heterologous genes, wherein said expression construct is not based upon Tilapia Lake Virus (TiLV), and wherein said expression construct comprises at least the following heterologous gene: a) a nucleic acid sequence chosen from the group consisting of SEQ ID NOs: 2-8 and 10-11, operably linked to a promoter for directing its expression.

2. The expression construct of claim 1, wherein the expression construct is a recombinant virus.

3. An engineered nucleic acid expression construct capable of driving expression of heterologous genes, wherein said expression construct is not based upon Tilapia Lake Virus (TiLV), and wherein said expression construct comprises at least the following heterologous gene: a) a nucleic acid sequence chosen from the group consisting of a variant of any one of SEQ ID NOs: 2-8 and 10-11, and a promoter for directing its expression, wherein the variant has at least 60% sequence identity to any one of SEQ ID NOs: 2-8 and 10-11.

4. The expression construct of claim 3 wherein the variant has at least 75%, 80%, 85%, 90%, 95%, 96%, 97%, 98%, 99%, or 99.5% identity to any of SEQ ID NOs: 2-8 and 10-11.

5. An immunogenic composition comprising the expression construct of claim 1.

6. The immunogenic composition of claim 5, further comprising at least one excipient, additive or adjuvant.

7. A method of inducing an immune response in an animal, the method comprising administering the immunogenic composition of claim 5.

8. A method of inducing an immune response in an animal, the method comprising administering the immunogenic composition of claim 6.

9. The method of claim 7, wherein the immunogenic composition is administered orally, by immersion or by injection.

10. The method of claim 8, wherein the immunogenic composition is administered orally, by immersion or by injection.

11. An immunogenic composition comprising the expression construct of claim 3.

12. The immunogenic composition of claim 11, further comprising at least one excipient, additive or adjuvant.

13. A method of inducing an immune response in an animal, the method comprising administering the immunogenic composition of claim 11.

14. A method of inducing an immune response in an animal, the method comprising administering the immunogenic composition of claim 12.

15. The method of claim 13, wherein the immunogenic composition is administered orally, by immersion or by injection.

16. The method of claim 14, wherein the immunogenic composition is administered orally, by immersion or by injection.

* * * * *

SEQUENCE LISTING

```
<160> NUMBER OF SEQ ID NOS: 39

<210> SEQ ID NO 1
<211> LENGTH: 1326
<212> TYPE: DNA
<213> ORGANISM: Tilapia Lake RNA Virus

<400> SEQUENCE: 1
gaaatggact cgcggtttgc acagctaact ggggttttct gtgacgattt cacttatagc      60
gaagggagcc gaaggttcct aagttcttac agtacagtag agagacgtcc aggagtcccc     120
gtagagggtg actgttatga ctgtttgaag aataagtgga ttgcctttga gctggaaggc     180
cagccgcgga aatttccaaa ggcaacagtt cgttgcattt tgaacaatga tgctacatac     240
gtttgctctg agcaagagta ccagcagatt tgtaaggtac aattcaagga ttatttggag     300
atcgacgggg ttgttaaagt tgggcacaag gcatcctacg atgctgagct aagggaacgg     360
ctattggaac taccacatcc aaagagtggc ccgaagcctc gtattgagtg ggtggcacca     420
cccagacttg cggacatatc caaggaaaca gctgagctaa agaggcaata tggattcttc     480
gagtgctcaa agttcctcgc ctgcggtgag gagtgtggtc ttgaccaaga ggcaagagaa     540
cttatactga acgagtacgc acgtgataga gaatttgagt tccgcaatgg agggtggata     600
caaaggtata cagttgcttc tcacaagcct gctacacaga agatattacc tctaccggct     660
agtgctccac ttgctcgtga gcttttgatg ttgattgcta gaagcacaac tcaggcaggg     720
aaagtactgc atagcgataa taccagcata ctagctgtac cggtcatgcg cgactctgga     780
aagcacagta aaaggagacc aaccgcctcc actcaccact tagttgtagg tctaagtaaa     840
cctggctgtg aacacgattt tgagtttgac gggtacaggg cagctgtgca tgtgatgcac     900
ctagatccca agcaatcggc taatataggg gagcaagact ttgtgagtac ccgagaaatt     960
tacaagctgg atatgttgga actacctccc ataagtagga agggtgatct ggacagagct    1020
agtggtcttg agacaagatg ggacgtcatc ttacttctgg aatgcctcga ctctacaagg    1080
gttagccaag cagtggctca acattttaat aggcaccggc tagcacttag cgtctgtaag    1140
gacgagttca ggaaaggcta ccagctggct tctgagataa ggggtacaat acccttaagc    1200
tcactttatt attcactttg tgcagtaaga ttgcggatga cagtacaccc atttgcgaga    1260
tgatcgcttt cgacgccttc gctaaaggtt acgacgttct aatagaggat tatgggaaaa    1320
atttgc                                                               1326

<210> SEQ ID NO 2
<211> LENGTH: 1471
<212> TYPE: DNA
<213> ORGANISM: Tilapia Lake RNA Virus

<400> SEQUENCE: 2
ccaaatttta ctctctatta ccaaatacat ttacttctga aaaatgagtc agtttgggaa      60
atcattcaag ggcagaactg aggtcacaat aaccgaatat cgctctcata ctgtcaaaga     120
tgtgcacaga agcttactta cggctgacaa gtctctaagg aagtcattct gttttaggaa     180
cgccctaaac cagttcttgg ataaagattt gcctcttttg cccattcggc caaaattaga     240
```

-continued

```
gtccagggtt gctgtgaaaa agtctaagct gaggagtcag ctgtcgttca gacccggttt      300
gactcaggag gaagcaattg atctttacaa caagggctat gatggtgaca gcgtctcagg      360
tgccttgcaa gacagggtag tcaatgagcc tgtagcttac tcgagtgcag ataatgacaa      420
atttcacagg ggcttagcgg ctctagggta cactttggct gatagagcat ttgatacatg      480
cgaatccggc ttcgtgagag caattcctac cactccatgc gggttcatat gttgtgggcc      540
aggttctttc aaagattcac ttggatttgt gataaaaatc ggcgaattct ggcacatgta      600
tgacgggttc caacacttcg tcgctgtcga ggatgctaag ttcctagcaa gtaagtctcc      660
ttcgttttgg ttggcaaaac gtcttgcaaa gaggctgaat ctggtcccaa agaggatcc      720 atctatagca gcagctgagt gcccttgtag aaagtgtgg gaagctagtt ttgctagggc      780
acctactgca ctagatccat ttggaggcag ggccttctgc gaccagggtt gggtgtacca      840
cagggacgta gggtatgcaa cagctaacca catatcacag gaaacacttt tcaacaagc      900 gctttcagtg aggaaccttg gaccgcaagg tagtgcaaat gtctcaggct caatacatac      960
cgccctggac aggctcagag cagcgtacag tagggggacg cccgcctcta gatctatact     1020
gcaagggctt gcaaatctca tcacacctgt aggtgaaaac tttgaatgcg atctcgacaa     1080
gaggaagctc aatataaagg cattacgttc tcccgagagg tacattacga tagagggcct     1140
ggttgtaaac ctggacgatg tggttagagg gttctacctt gacaaggcga aggtcactgt     1200
tctctcgaga tcaaagtgga tgggttacga ggaccttcct cagaaacctc cgaacggtac     1260
attttactgt agaagagga aggcaatgct tctcatctca tgtagtccag gcacgtacgc     1320
aaagaagcga aaagtggcag tgcaggagga tcgctttaaa gatatgaggg ttgagaattt     1380
ccgggaggta gcggaaaata tggatctaaa tcagtagggt ttccttggcaa aagccttcac     1440 tatatatatg gtaataatga gaaagatttg c                                    1471
```

<210> SEQ ID NO 3
<211> LENGTH: 1098
<212> TYPE: DNA
<213> ORGANISM: Tilapia Lake RNA Virus

<400> SEQUENCE: 3

```
ccaaatgttt ctcttagctc agactccaat agctatgcag gcgctggtcc tgacaagctg       60
cctagtttgc gcactagcaa gtgatgaaag tttaaggata aaacgactac aatcatacct      120
aaacaatacc taccaaagta gggagataga agtgaaata aggcgtggat ttgcatccaa      180
gttcaggatg gagagttgct cctgcactat ggggtgcac tacattgtaa ccccatcctc      240
gggtgggtcg ttctgcactg ggttacatgc agtacctaac agcttccag ccctcgggta      300 caaacttccc aaagcagggg gaagaggtga ttggaaagct actgaagtta ggattgacga      360
agatagtggg gttgttctat acaacgtttc caggtgcagc cacagtagcg agtgcagaga      420
tttggaggtg tattccaccg tactgccagg tcagtgtgac tgtaccagac ccactgtgga      480
cgactacaag accatgctgg cctcaaggca gccgaagtcg tttgtagtag caggcctcat      540
tatactgtgt ttacttgcta gctcagtagc aattggcatg ggtgtttaca attatgctgg      600
ggtcatcggc ctagcggacg cagctcaagc agatgtttct gagatttggg agtacttaga      660
agctttgaca cggaagtca ccggtatgac gctaggagag ttttgctcga ttaaatccct      720
cgtctgtaaa tctgataaca taggcaaatt caaagagcaa tttgcagcct tggggaagc      780 tattcttgca atagtgtttg ggatgctaga gaaatataag tttgtctatt acctggtgct      840
```

```
ttcgctgatg gttctctcgc tactcagtaa acttgtttct ctgttgaagc aggtgccctt     900
ctatgggagt atcaaagttt tagtattccg gaggctaaga gttgtgtgtt tcaagacctt     960
tttctatatt aagaagcggc ttaagaagaa aagcccgctt gaggatgacg aagtccctct    1020
gcttccatta tcttgatcct taagcttcta ttcctggtag gtcataaagt ggtaaactga    1080
gaaaagagta aaatttgc                                                  1098

<210> SEQ ID NO 4
<211> LENGTH: 1044
<212> TYPE: DNA
<213> ORGANISM: Tilapia Lake RNA Virus

<400> SEQUENCE: 4
ccaaatttta cctctcgcat gcatttttat ctacaggatt gtccaatgag ttggcttagg      60
gtgataagaa cccttacttt gttttcaaca ctctttaacg gaagcgatca atgcgtggac     120
aacatgtggc ggttttacgg gagatcaaac tacacgtcaa gcgtagtcat tgacggggac     180
aaatattctg ttgaaggttc atattcgagt agtgattatc tggatccagc agtacagaag     240
gtggttctgg gacttgatgg tagcaacgaa gtcatagact caggtgggtc tccatactac     300
atgtatgatt tggagggatc aaaagggaa ctccatcatc tgaactgcaa cttttgtcgag    360
aaacgatgta atccgacgct aaactttatg cttggaggat tgttttgtg cccaggaata     420
tcgagaaaag aactggagcc tgtaaccgac aagatattgg agagccgggg aataccgggc    480
cgaggtaaaa tacgtactat aaaaataagc tctaaactgt ttgagacatc gctgtgcctt    540
tcgaagagga ggcccatctt tagcacctgt atgctaatgt cgcgtggtct ttgtacaaac    600
tgtaagcgta ctatagatag aacatatatg acgccaaacg gcttcagaac tgaatacaag    660
tggagctgca gagacaatag cacaaaacag tgttgggtat tagttgagtc actggaggag    720
aatcactccc catacaaatg ccacttttcc gcagtggaag tcctactacc agccgaaata    780
aagcgtcacc agctcatcag cgagtggtcc gcgatgcagg atgaagttgc ttataagaag    840
tcaaatgctt atcttcttgc tcgtactttt cttagctata caaaaatgcg tagattaaat    900
cctgtaattg atctttcgat atcaccacca gtgacagtaa gatcctgctg taaaattaat    960
aaatacatgt gacactatat gtcctatcat gtgggcgaaa tgcccaggta cagttttaag   1020
tgcttgattg agagaaatat ttgc                                          1044

<210> SEQ ID NO 5
<211> LENGTH: 777
<212> TYPE: DNA
<213> ORGANISM: Tilapia Lake RNA Virus

<400> SEQUENCE: 5
ccaaatttta ctctctttgc attgcatacc gtatagtaat agacacaatg tcctacaaga      60
ttggtgagct tgagagaatt atcacgcgca aaaacaccct ccccaaggac agcggaagtc     120
agactgggct gttccatcga ctgctcctag agcattactc tggtgcctcg aacgtatggt    180
tcttttgtgc aactgggttt acacccaata caaatggcac aacctggatt gtattgacga    240
gtcacccaac cgatggtgga gaaaaggtac ctttgaaatg gaagtatgaa gtgagccccg    300
gattgccagt cagaagggta cttgcccagg agggtacagc agtaagaggc ccgaaaggag    360
cctatttagt caaaggggac atgcatctct gttcaactac cttctacact agaagggaag    420
cgaagtactg gctctgtgcg ccatcccaa agtttccaca ttggaccaag agatcagcgt     480
tggtgaccag cactcgacca ctgactgagt tgagcagggt tgccacatac ctagaggcta    540
```

```
taagtaaggg tgcaactgat gtcaatgaat cgtggtgttc ctaccacaga gttgggttag    600
tgccaatccc taaaggaatc acgtttgaac tctaattacc cagctgtttc gttgtcttat    660
tggggaggcc tttctaagtt aactaattac ttttgaaagc agggataatt ggtctgagag    720
cttcttatgg tactcagtac cgttcactaa ggatggtagc atgagagaaa gatttgc      777
```

<210> SEQ ID NO 6
<211> LENGTH: 1249
<212> TYPE: DNA
<213> ORGANISM: Tilapia Lake RNA Virus

<400> SEQUENCE: 6

```
ccaaagttta ctcctattac ccagaatagc taacttaata aactgaaaat ggtgagaact    60
acaaagacta gtatggcagc tgccagcact gttgcaccag aggtagcaat ggatgaaagt    120
tcacccagca cttcgcaggt acaagctgaa ctcccaagaa accttgaggt tttcaacgaa    180
gcttgtggtc atgtgtttgg aagttccttt aacaggagg acaacagtgt gatatctgat    240
gctgctgcat ttctctttaa aatgcacact cactccctcg atggtcagga ggctaaggtt    300
ctgagagcca gtgaaaagaa gagagagagg gagaacgcta agaaatcaag gaaggcacca    360
gaagcaggga tgagggtcgg aaggagcctt atattaacca gcagatggac tgaatactgc    420
gcaacctgtg tgcctgcact gggctcaaag atgaaggtga taaaagcctc aggggacgca    480
gctatgattc agatgatgaa ggaccataac tctctattaa gagtgtgtgt tcgcattgag    540
gtctggaagg ctaggtacgt cagtttggtt gctctcgacg agaggattca gactttggag    600
gacgcccaat ggttcccata tctgagtggg gattcctatc gtgcttgccc agggctggtt    660
ggtggctact ttgcaaagaa agcagcagca ggagaaagag gaaagaacta caaaaagttg    720
aatcagactg ctataatccc gcctccgaga tttctgatca ttggccacag gctgcagata    780
ggcgaccagg tcaccctcag ggagctgctt gcctcaattg cttggggcct ttgcgacggt    840
gtccttgctg agtgttggag cccctcgcag ggggacggga gtattggtgt tgttgttggt    900
ctacctctgc aagctacagg aagctgcttc ctggtggtag ctagccacgg gctctcagca    960
attgccgact ctaggattga gggaacaggg aacacgaatc tgctggaaga atgcattgcc    1020
attcagaaac aggacggtgt cataaaaatgt aagagaagtg ggaagagtct gtatcactgc    1080
ctcaaggaga cagcaggggc tgttgggaga taggcaacga agtaggccac ccatgcgcgg    1140
aaagctgcac aggctgccaa gggcccctct tagcccaagt tttctatata ttctttaaca    1200
agtcatctaa aactggtaaa ttcttagacg gtaattggag aaagatttg               1249
```

<210> SEQ ID NO 7
<211> LENGTH: 1640
<212> TYPE: DNA
<213> ORGANISM: Tilapia Lake RNA Virus

<400> SEQUENCE: 7

```
ccaaacgtta tctcttaatt acgcactatt actgtactac cataaggtat gtgggcattt    60
caagaaggag tttgcaaagg taacctgtta tcaggcccga cctcaatgaa ggcaccggat    120
tcagcagcga gggagtcatt agacagagcg tctgaaatca tgcacaggaaa atcgtacaat    180 gctgtccaca ctggggactt aagcaagctg cctaatcagg gagaaagtcc actgaggata    240
gtcgattccg acctttattc agaaaggagt tgctgtgggg ttatagagaa ggagggcaga    300
gttgtatgca aaagtaccac gctcacccgc ggtatgacgg gcctgttgaa cacaacaagg    360
```

```
tgtagttctc catctgagct catatgtaag gttttgacag tagaatccct atctgaaaag    420
ataggtgaca cgagcgtcga ggagttactt tctcatggca ggtactttaa gtgcgcactt    480
cgcgaccagg agaggggtaa acccaagagc agagctatct ttctgtcaca tccattcttc    540
agattgcttt cctctgtagt agagacgcac gctagatctg tgctgtcaaa ggtctcagca    600
gtgtacaccg ctactgctag tgcagaacaa cgggctatga tggccgcaca ggttgtagag    660
tcaagaaaac atgttcttaa tggcgactgt actaagtata atgaggcaat cgacgcagac    720
acactgctaa aagtgtggga tgcaataggc atggggtcaa tcggagtcat gctcgcttac    780
atggtgcgca ggaaatgcgt tctcattaaa gacactctag tagagtgtcc aggaggtatg    840
ttgatgggaa tgtttaacgc aactgccacc ttggcattgc aggggacgac tgacagattc    900
ctgtctttca gcgacgactt tataacatcg tttaactcgc ctgctgaatt acgcgagata    960
gaggacctgc ttttcgcaag ctgtcataac ttgtcgctaa agaagagtta catttcagtt   1020
gcctcactgg aaataaactc gtgtaccctc actagggacg gtgacctagc cacagggttg   1080
ggttgtactg ctggtgtccc tttcagggga ccacttgtga ctctgaaaca gactgcagct   1140
atgttatctg gcgctgttga ctcaggagtt atgccattcc actcagcaga acgtctgttc   1200
cagataaagc agcaggaatg tgcctatagg tataacaacc ccacttacac aacgaggaat   1260
gaggacttcc tccccacatg cctgggaggg aagactgtaa ttagctttca atctctactg   1320
acttgggatt gccacccatt ttggtaccag gtgcaccccg atggcccaga cactatagat   1380
cagaaagtcc tgtctgtcct tgcttcaaag actcgcagaa ggagaacccg actggaggct   1440
ctctcagact tggaccccct ggtccctcat aggctcctcg tatcagagtc agacgttagc   1500
aagatcagag cagctaggca ggctcacttg aagtccttag gcttggaaca acccacaaac   1560
tttaactatg ctatttataa agcagtccag cccaccgctg ggtgctaagt aactatatag   1620
gcgaatgaga gaaatatttg                                               1640

<210> SEQ ID NO 8
<211> LENGTH: 465
<212> TYPE: DNA
<213> ORGANISM: Tilapia Lake RNA Virus

<400> SEQUENCE: 8
ccaaatttta accctactaa caccaaatat agctataagc caggatgagt gtggcagatt     60
atttgtcaag tgacagtgac tcgggggctg agagctcagg atgtttagta ctaagaagtc    120
ggaagatcaa gaagggcaag aaagctgctt caaagaagcg aagttggaag aatgaaaggt    180
atggtgctga cgagagcggt gaagataata tagagtgggg tgacgaagtc gacctcgaga    240
tggacgactg tgattctgca atcccagagt gggctagggt tgatttcaat cccaaaaaca    300
gaagggacag agaggatgat gggcagagtg acctatctcg attttccgaa gatttcggaa    360
agaagtctct tgacgtgcag tcttagcacc ttaatatcgg ttctgatttc gttcgtatcc    420
acaggccaac gctaactata cagggtgtca gagggaaaga tttgc                    465

<210> SEQ ID NO 9
<211> LENGTH: 1371
<212> TYPE: DNA
<213> ORGANISM: Tilapia Lake RNA Virus

<400> SEQUENCE: 9
ccaaatatta ccccttaatc cttaatagac cgttaacttt cttttgaaat ggactcgcgg     60
tttgcacagc taactggggt tttctgtgac gatttcactt atagcgaagg gagccgaagg    120
```

-continued

```
ttcctaagtt cttacagtac agtagagaga cgtccaggag tccccgtaga gggtgactgt     180
tatgactgtt tgaagaataa gtggattgcc tttgagctgg aaggccagcc gcggaaattt     240
ccaaaggcaa cagttcgttg cattttgaac aatgatgcta catacgtttg ctctgagcaa     300
gagtaccagc agatttgtaa ggtacaattc aaggattatt ggagatcga cggggttgtt     360 aaagttgggc acaaggcatc ctacgatgct gagctaaggg aacggctatt ggaactacca     420
catccaaaga gtgccccgaa gcctcgtatt gagtgggtgg caccacccag acttgcggac     480
atatccaagg aaacagctga gctaaagagg caatatggat tcttcgagtg ctcaaagttc     540
ctcgcctgcg gtgaggagtg tggtcttgac caagaggcaa gagaacttat actgaacgag     600
tacgcacgtg atagagaatt tgagttccgc aatggagggt ggatacaaag gtatacagtt     660
gcttctcaca agcctgctac acagaagata ttacctctac cggctagtgc tccacttgct     720
cgtgagcttt tgatgttgat tgctagaagc acaactcagg cagggaaagt actgcatagc     780
gataatacca gcatactagc tgtaccggtc atgcgcgact ctggaaagca cagtaaaagg     840
agaccaaccg cctccactca ccacttagtt gtaggtctaa gtaaacctgg ctgtgaacac     900
gattttgagt ttgacgggta cagggcagct gtgcatgtga tgcacctaga tcccaagcaa     960
tcggctaata taggggagca agactttgtg agtacccgag aaatttacaa gctggatatg    1020
ttggaactac ctcccataag taggaagggg gatctggaca gagctagtgg tcttgagaca    1080
agatgggacg tcatcttact tctggaatgc ctcgactcta caagggttag ccaagcagtg    1140
gctcaacatt ttaataggca ccggctagca cttagcgtct gtaaggacga gttcaggaaa    1200
ggctaccagc tggcttctga gataagggt acaatacct taagctcact ttattattca    1260
ctttgtgcag taagattgcg gatgacagta cacccatttg cgagatgatc gctttcgacg    1320
ccttcgctaa aggttacgac gttctaatag aggattatgg gaaaaatttg c             1371
```

<210> SEQ ID NO 10
<211> LENGTH: 548
<212> TYPE: DNA
<213> ORGANISM: Tilapia Lake RNA Virus

<400> SEQUENCE: 10

```
ccaaattta ctcacaagtc cgattacttt ttccgcttgg tgatgtcacg atggatagaa      60
aatacagatt ctgtgtcagt aatcttgaca gagatgagtc ggtcgtacgt cactttgtgc    120
cattaccccc cttggagctt gtgctgcggc ggcaagacat cacaacctgg tcaagtctgg    180
atcctggatc gaaaacattg tctagaatgt tcagagatct cagagttaat gacactgagt    240
cagccaactt ggcaggagag tgcaatggtg atagggagct gggtccaagt agtaacggag    300
cacggaattt tgcacacttc aacatcggaa aggcaggcac caagaagggt catgtggagg    360
atatctgaca tggctggcga tagaacttta tgagggcggt ccaggggcaa ttgaagctcc    420
gcgaacctac tgattcctca gctagaacat tgtagtgaac catgtgacat taataattta    480
gctttagtaa aaatggataa gcttcagctc tggcaaagta tgactttaag gacgtgagaa    540
agatttgc                                                              548
```

<210> SEQ ID NO 11
<211> LENGTH: 657
<212> TYPE: DNA
<213> ORGANISM: Tilapia Lake RNA Virus
<220> FEATURE:
<221> NAME/KEY: misc_feature
<222> LOCATION: (1)..(1)

<223> OTHER INFORMATION: n is a, c, g, or t

<400> SEQUENCE: 11

```
ncaaatatta cctcatctac actaacattt ccaattggac agcatatcca ggaataagta      60
tggctcaaat cccaacacta agagagggcc aagggaagct ctacgatttc acgctcaacg     120
gcatgacagt gactagagac acagtcaaca ctgtagttgc tctggagttt cttgtcaatg     180
caggtccgga tttgctttcc ctaacaattg gcgaaggcct ctcagaagaa acaaagttta     240
aacacctgct tgttaagcac gccggcatga cccgaaagcg gatagaggaa aggctgggac     300
gaatctcgag gcgagtcagt gtgacagtcg acgcaattat aataacaaac cgcaagggtc     360
aaagatttga attcaatcgg aagcagtacc tggatattgc caaacaagct atgaagctta     420
agctccctgg gattaactgt gtcgacatac ccactgcgct cgcttttctc gaggaggtcc     480
tggcaactgc tttgaaggac actgaaggtt cacaagatga caggatggcc cttaaggcag     540
acacttctgc tgctatcaat catttccgtg aaatgcttaa ataaaaagtg agtcttcagt     600
gtcattttcc ccagggaggt aagctactcc atttgtgtaa tgatgagaaa aatttgc       657
```

<210> SEQ ID NO 12
<211> LENGTH: 420
<212> TYPE: PRT
<213> ORGANISM: Tilapia Lake RNA Virus

<400> SEQUENCE: 12

```
Glu Met Asp Ser Arg Phe Ala Gln Leu Thr Gly Val Phe Cys Asp Asp
1               5                   10                  15

Phe Thr Tyr Ser Glu Gly Ser Arg Arg Phe Leu Ser Ser Tyr Ser Thr
                20                  25                  30

Val Glu Arg Arg Pro Gly Val Pro Val Glu Gly Asp Cys Tyr Asp Cys
            35                  40                  45

Leu Lys Asn Lys Trp Ile Ala Phe Glu Leu Glu Gly Gln Pro Arg Lys
        50                  55                  60

Phe Pro Lys Ala Thr Val Arg Cys Ile Leu Asn Asn Asp Ala Thr Tyr
65                  70                  75                  80

Val Cys Ser Glu Gln Glu Tyr Gln Gln Ile Cys Lys Val Gln Phe Lys
                85                  90                  95

Asp Tyr Leu Glu Ile Asp Gly Val Val Lys Val Gly His Lys Ala Ser
            100                 105                 110

Tyr Asp Ala Glu Leu Arg Glu Arg Leu Leu Glu Leu Pro His Pro Lys
        115                 120                 125

Ser Gly Pro Lys Pro Arg Ile Glu Trp Val Ala Pro Arg Leu Ala
    130                 135                 140

Asp Ile Ser Lys Glu Thr Ala Glu Leu Lys Arg Gln Tyr Gly Phe Phe
145                 150                 155                 160

Glu Cys Ser Lys Phe Leu Ala Cys Gly Glu Glu Cys Gly Leu Asp Gln
                165                 170                 175

Glu Ala Arg Glu Leu Ile Leu Asn Glu Tyr Ala Arg Asp Arg Glu Phe
            180                 185                 190

Glu Phe Arg Asn Gly Gly Trp Ile Gln Arg Tyr Thr Val Ala Ser His
        195                 200                 205

Lys Pro Ala Thr Gln Lys Ile Leu Pro Leu Pro Ala Ser Ala Pro Leu
    210                 215                 220

Ala Arg Glu Leu Leu Met Leu Ile Ala Arg Ser Thr Thr Gln Ala Gly
225                 230                 235                 240
```

```
Lys Val Leu His Ser Asp Asn Thr Ser Ile Leu Ala Val Pro Val Met
            245                 250                 255

Arg Asp Ser Gly Lys His Ser Lys Arg Pro Thr Ala Ser Thr His
    260                 265                 270

His Leu Val Val Gly Leu Ser Lys Pro Gly Cys Glu His Asp Phe Glu
    275                 280                 285

Phe Asp Gly Tyr Arg Ala Ala Val His Val Met His Leu Asp Pro Lys
    290                 295                 300

Gln Ser Ala Asn Ile Gly Glu Gln Asp Phe Val Ser Thr Arg Glu Ile
305                 310                 315                 320

Tyr Lys Leu Asp Met Leu Glu Leu Pro Pro Ile Ser Arg Lys Gly Asp
                325                 330                 335

Leu Asp Arg Ala Ser Gly Leu Glu Thr Arg Trp Asp Val Ile Leu Leu
                340                 345                 350

Leu Glu Cys Leu Asp Ser Thr Arg Val Ser Gln Ala Val Ala Gln His
                355                 360                 365

Phe Asn Arg His Arg Leu Ala Leu Ser Val Cys Lys Asp Glu Phe Arg
        370                 375                 380

Lys Gly Tyr Gln Leu Ala Ser Glu Ile Arg Gly Thr Ile Pro Leu Ser
385                 390                 395                 400

Ser Leu Tyr Tyr Ser Leu Cys Ala Val Arg Leu Arg Met Thr Val His
                405                 410                 415

Pro Phe Ala Arg
            420

<210> SEQ ID NO 13
<211> LENGTH: 24
<212> TYPE: DNA
<213> ORGANISM: Artificial Sequence
<220> FEATURE:
<223> OTHER INFORMATION: synthetic primre
<220> FEATURE:
<221> NAME/KEY: misc_feature
<222> LOCATION: (19)..(24)
<223> OTHER INFORMATION: n is a, c, g, or t

<400> SEQUENCE: 13
ggaactcaat gcacgcgtnn nnnn                                          24

<210> SEQ ID NO 14
<211> LENGTH: 18
<212> TYPE: DNA
<213> ORGANISM: Artificial Sequence
<220> FEATURE:
<223> OTHER INFORMATION: synthetic primer

<400> SEQUENCE: 14
ggaactcaat gcacgcgt                                                 18

<210> SEQ ID NO 15
<211> LENGTH: 54
<212> TYPE: DNA
<213> ORGANISM: Artificial Sequence
<220> FEATURE:
<223> OTHER INFORMATION: synthetic primer
<220> FEATURE:
<221> NAME/KEY: misc_feature
<222> LOCATION: (54)..(54)
<223> OTHER INFORMATION: n is a, c, g, or t

<400> SEQUENCE: 15
ccagtgagca gagtgacgag gactcgagct caagctttttt tttttttttt ttvn        54
```

<210> SEQ ID NO 16
<211> LENGTH: 23
<212> TYPE: DNA
<213> ORGANISM: Artificial Sequence
<220> FEATURE:
<223> OTHER INFORMATION: synthetic primer

<400> SEQUENCE: 16
tatcacgtgc gtactcgttc agt                                           23

<210> SEQ ID NO 17
<211> LENGTH: 18
<212> TYPE: DNA
<213> ORGANISM: Artificial Sequence
<220> FEATURE:
<223> OTHER INFORMATION: synthetic primer

<400> SEQUENCE: 17
ccagtgagca gagtgacg                                                 18

<210> SEQ ID NO 18
<211> LENGTH: 18
<212> TYPE: DNA
<213> ORGANISM: Artificial Sequence
<220> FEATURE:
<223> OTHER INFORMATION: synthetic primer

<400> SEQUENCE: 18
gaggactcga gctcaagc                                                 18

<210> SEQ ID NO 19
<211> LENGTH: 19
<212> TYPE: DNA
<213> ORGANISM: Artificial Sequence
<220> FEATURE:
<223> OTHER INFORMATION: synthetic primer

<400> SEQUENCE: 19
aagttctctt gcctcttgg                                                19

<210> SEQ ID NO 20
<211> LENGTH: 20
<212> TYPE: DNA
<213> ORGANISM: Artificial Sequence
<220> FEATURE:
<223> OTHER INFORMATION: synthetic primer

<400> SEQUENCE: 20
cacccagact tgcggacata                                               20

<210> SEQ ID NO 21
<211> LENGTH: 19
<212> TYPE: DNA
<213> ORGANISM: Artificial Sequence
<220> FEATURE:
<223> OTHER INFORMATION: synthetic primer

<400> SEQUENCE: 21
tccaaggaaa cagctgagc                                                19

<210> SEQ ID NO 22
<211> LENGTH: 20
<212> TYPE: DNA
<213> ORGANISM: Artificial Sequence
<220> FEATURE:

<223> OTHER INFORMATION: synthetic primer

<400> SEQUENCE: 22
gaggcaatat ggattcttcg                                                   20

<210> SEQ ID NO 23
<211> LENGTH: 20
<212> TYPE: DNA
<213> ORGANISM: Artificial Sequence
<220> FEATURE:
<223> OTHER INFORMATION: synthetic primer

<400> SEQUENCE: 23
gttgggcaca aggcatccta                                                   20

<210> SEQ ID NO 24
<211> LENGTH: 20
<212> TYPE: DNA
<213> ORGANISM: Artificial Sequence
<220> FEATURE:
<223> OTHER INFORMATION: synthetic primer

<400> SEQUENCE: 24
tatgcagtac tttccctgcc                                                   20

<210> SEQ ID NO 25
<211> LENGTH: 20
<212> TYPE: DNA
<213> ORGANISM: Artificial Sequence
<220> FEATURE:
<223> OTHER INFORMATION: synthetic primer

<400> SEQUENCE: 25
ttgctctgag caagagtacc                                                   20

<210> SEQ ID NO 26
<211> LENGTH: 18
<212> TYPE: DNA
<213> ORGANISM: Artificial Sequence
<220> FEATURE:
<223> OTHER INFORMATION: synthetic primer

<400> SEQUENCE: 26
cagatcactg atcgatgc                                                     18

<210> SEQ ID NO 27
<211> LENGTH: 18
<212> TYPE: DNA
<213> ORGANISM: Artificial Sequence
<220> FEATURE:
<223> OTHER INFORMATION: synthetic primer

<400> SEQUENCE: 27
gtctgaaagg taaggtgg                                                     18

<210> SEQ ID NO 28
<211> LENGTH: 23
<212> TYPE: DNA
<213> ORGANISM: Artificial Sequence
<220> FEATURE:
<223> OTHER INFORMATION: synthetic primer

<400> SEQUENCE: 28
agttgcttct cayaagcctg cta                                               23

```
<210> SEQ ID NO 29
<211> LENGTH: 24
<212> TYPE: DNA
<213> ORGANISM: Artificial Sequence
<220> FEATURE:
<223> OTHER INFORMATION: synthetic primer

<400> SEQUENCE: 29
tcgtgttcac arccaggttt actt                                          24

<210> SEQ ID NO 30
<211> LENGTH: 21
<212> TYPE: DNA
<213> ORGANISM: Artificial Sequence
<220> FEATURE:
<223> OTHER INFORMATION: synthetic primer

<400> SEQUENCE: 30
ggtcaattcg agtcatgctc g                                             21

<210> SEQ ID NO 31
<211> LENGTH: 26
<212> TYPE: DNA
<213> ORGANISM: Artificial Sequence
<220> FEATURE:
<223> OTHER INFORMATION: synthetic primer

<400> SEQUENCE: 31
gctggactgc tttataaata gcatag                                        26

<210> SEQ ID NO 32
<211> LENGTH: 21
<212> TYPE: DNA
<213> ORGANISM: Artificial Sequence
<220> FEATURE:
<223> OTHER INFORMATION: synthetic primer

<400> SEQUENCE: 32
atcctgcgtc tggacctggc t                                             21

<210> SEQ ID NO 33
<211> LENGTH: 21
<212> TYPE: DNA
<213> ORGANISM: Artificial Sequence
<220> FEATURE:
<223> OTHER INFORMATION: synthetic primer

<400> SEQUENCE: 33
tgccaatggt gatgacctgt c                                             21

<210> SEQ ID NO 34
<211> LENGTH: 19
<212> TYPE: DNA
<213> ORGANISM: Artificial Sequence
<220> FEATURE:
<223> OTHER INFORMATION: synthetic primer

<400> SEQUENCE: 34
agctatgtta tctggcgct                                                19

<210> SEQ ID NO 35
<211> LENGTH: 22
<212> TYPE: DNA
<213> ORGANISM: Artificial Sequence
<220> FEATURE:
<223> OTHER INFORMATION: synthetic primer
```

```
<400> SEQUENCE: 35
gttgttatac ctataggcac at                                              22

<210> SEQ ID NO 36
<211> LENGTH: 25
<212> TYPE: DNA
<213> ORGANISM: Artificial Sequence
<220> FEATURE:
<223> OTHER INFORMATION: synthetic probe

<400> SEQUENCE: 36
gccattccac tcagcagaac gtctg                                           25

<210> SEQ ID NO 37
<211> LENGTH: 22
<212> TYPE: DNA
<213> ORGANISM: Artificial Sequence
<220> FEATURE:
<223> OTHER INFORMATION: synthetic primer

<400> SEQUENCE: 37
gcgtgacatc aargagaagc tg                                              22

<210> SEQ ID NO 38
<211> LENGTH: 19
<212> TYPE: DNA
<213> ORGANISM: Artificial Sequence
<220> FEATURE:
<223> OTHER INFORMATION: synthetic primer

<400> SEQUENCE: 38
ccaatggtga tgacctgtc                                                  19

<210> SEQ ID NO 39
<211> LENGTH: 24
<212> TYPE: DNA
<213> ORGANISM: Artificial Sequence
<220> FEATURE:
<223> OTHER INFORMATION: synthetic probe

<400> SEQUENCE: 39
ccctggagaa gagttacgag ctgc                                            24
```